US012649746B2

(12) United States Patent
Ye et al.

(10) Patent No.: US 12,649,746 B2
(45) Date of Patent: Jun. 9, 2026

(54) KETOROLACO DERIVATIVE, PHARMACEUTICAL COMPOSITION AND PREPARATION METHOD THEREFOR AND USE THEREOF

(71) Applicant: NANJING HERON PHARMACEUTICAL SCIENCE AND TECHNOLOGY CO., LTD., Nanjing (CN)

(72) Inventors: Hai Ye, Nanjing (CN); Tao Min, Nanjing (CN); Tian Lv, Nanjing (CN); Wenliang Zhou, Nanjing (CN); Xingran Chen, Nanjing (CN); Yunqing Feng, Nanjing (CN); Meiling Mo, Nanjing (CN); Jialin Wang, Nanjing (CN)

(73) Assignee: NANJING HERON PHARMACEUTICAL SCIENCE AND TECHNOLOGY CO., LTD., Nanjing (CN)

( * ) Notice: Subject to any disclaimer, the term of this patent is extended or adjusted under 35 U.S.C. 154(b) by 648 days.

(21) Appl. No.: 18/145,901

(22) Filed: Dec. 23, 2022

(65) Prior Publication Data

US 2023/0134672 A1 May 4, 2023

Related U.S. Application Data

(63) Continuation-in-part of application No. PCT/CN2021/099033, filed on Jun. 9, 2021.

(30) Foreign Application Priority Data

Jun. 24, 2020 (CN) ........................ 202010591411.8

(51) Int. Cl.

| | |
|---|---|
| ***C07D 487/04*** | (2006.01) |
| ***A61P 19/02*** | (2006.01) |
| ***A61P 29/00*** | (2006.01) |
| ***C07D 519/00*** | (2006.01) |

(52) U.S. Cl.
CPC ............ *C07D 487/04* (2013.01); *A61P 19/02* (2018.01); *A61P 29/00* (2018.01); *C07D 519/00* (2013.01)

(58) Field of Classification Search
CPC ............................ C07D 487/04; C07D 519/00
See application file for complete search history.

(56) References Cited

FOREIGN PATENT DOCUMENTS

| | | | |
|---|---|---|---|
| EP | 1231209 | A1 | 8/2002 |
| WO | 2014138343 | A1 | 9/2014 |
| WO | 2017041142 | A1 | 3/2017 |

OTHER PUBLICATIONS

Stella (J. Pharmaceutical Sciences, 2010, 99(12), pp. 4755-4765).*
Niu, Bixi et al.; "Effective management of acute postoperative pain using intravenous emulsions of novel ketorolac prodrugs: in vitro and in vivo evaluations", European Journal of Pharmaceutical Sciences, vol. 149, Apr. 18, 2020; pp. 1-11.

* cited by examiner

*Primary Examiner* — Susanna Moore
(74) *Attorney, Agent, or Firm* — NKL Law; Allen Xue

(57) ABSTRACT

A ketorolaco derivative as shown in formula (I) has a better half-life and stability, has good pharmacokinetic properties, and has a higher stability in vitro; and as a preparation, the ketorolaco derivative can enhance efficacy and reduce toxicity. The present invention well improves the defects of frequent administration, gastrointestinal side effects, poor compliance and the like in traditional ketorolaco preparations.

(I)

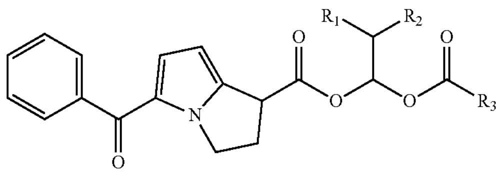

16 Claims, 14 Drawing Sheets

KETOROLACO DERIVATIVE, PHARMACEUTICAL COMPOSITION AND PREPARATION METHOD THEREFOR AND USE THEREOF

CROSS-REFERENCE TO RELATED APPLICATIONS

This application is a continuation-in-part of PCT International Application No. PCT/CN2021/099033, filed on Jun. 9, 2021, which claims priority to Chinese Patent Application No. 202010591411.8 filed with China National Intellectual Property Administration on Jun. 24, 2020 and entitled "KETOROLAC DERIVATIVE, PHARMACEUTICAL COMPOSITION AND PREPARATION METHOD THEREFOR AND USE THEREOF", the content of each is incorporated herein by reference in its entirety.

TECHNICAL FIELD

The present disclosure relates to a ketorolac derivative, a pharmaceutical composition, and a preparation method therefor and use thereof, and belongs to the field of pharmaceutical chemistry.

BACKGROUND

Ketorolac is a pyrrolidine carboxylic acid derivative, has a chemical structure and a pharmacological action similar to those of tolmetin, zomepirac and indomethacin, and belongs to a non-steroidal anti-inflammatory drug. Anti-inflammatory effects are produced primarily by inhibition of cyclooxygenase (COX) to reduce synthesis and release of prostaglandin. The reduction of prostaglandin can reduce the sensitivity of nerve fibers to noxious stimulation, thereby achieving the effects of analgesia, anti-inflammation and defervescence. Ketorolac has relatively strong analgesic activity which is 0.4 times that of morphine, 800 times that of aspirin and 60 times that of indomethacin. Compared with opioid analgesics, ketorolac has the advantages of rapid onset of drug action, no addiction, no central nervous system damage, no respiratory depression or adverse effect such as constipation, and long acting time. Ketorolac can be used together with morphine to reduce morphine dosage and thus reduce adverse effect and addiction caused by morphine.

Ketorolac is rapidly absorbed by oral administration and intramuscular injection, with the effective treatment plasma concentration being 0.3-5 μg/L, the peak concentration time of the plasma concentration being 20-60 min, and the bioavailability being 80%-100%; the binding rate of the reagent to plasma protein is more than 99%, the distribution volume is 0.1-0.3 L/kg, and the total clearance rate is 0.03 $L \cdot kg^{-1} \cdot h^{-1}$; the blood-cerebrospinal fluid barrier is not easy to permeate; it mainly binds to hepatic glucuronic acid and is subjected to hydroxylation metabolism, the elimination half-life being 4-6 h, wherein the elimination half-life in elderly patients is 6-7 h, and the elimination half-life in renal insufficiency patients is 9-10 h; about 90% of the original drug and metabolites are excreted with the urine. It shows that the ketorolac has the advantages of low effective concentration and high analgesic activity. However, the traditional injection and the route of oral administration have the defects of too high elimination rate, short analgesia time and the like. Ketorolac has poor water solubility, and in order to improve the water solubility of ketorolac, meet the requirements of injection and oral administration and ensure that the ketorolac can quickly take effect in body fluid and gastrointestinal tracts, ketorolac is usually formulated into ketorolac tromethamine salt. Ketorolac tromethamine is developed and listed by the Syntex company in the United States, and mainly comprises formulations for oral administration (10 mg/time) and injection (30 mg/time), such as capsules, injections and the like. Traditional formulations of ketorolac tromethamine for oral administration and injection have the defects of frequent administration, gastrointestinal side effects shared by non-steroidal drugs, poor compliance and the like.

SUMMARY

The objectives of the present disclosure are to provide a ketorolac derivative, a pharmaceutical composition, and a preparation method therefor and use thereof.

The present disclosure is mainly implemented by the following technical solutions:

One objective of the present disclosure is to provide a ketorolac derivative, namely a compound represented by formula (I), and a racemate, a stereoisomer, a pharmaceutically acceptable salt or a solvate thereof, (I)

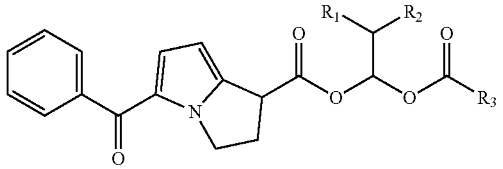

wherein $R_1$, $R_2$ and $R_3$ are identical or different and are each independently selected from hydrogen, $C_{1-40}$ alkyl, $C_{2-40}$ alkenyl, $C_{2-40}$ alkynyl, $C_{1-40}$ alkoxy, $C_{3-40}$ cycloalkyl, $C_{3-40}$ cycloalkyloxy, 3-20 membered heterocyclyl, $C_{6-20}$ aryl unsubstituted or substituted with Ra, 5-20 membered heteroaryl unsubstituted or substituted with Ra, and 3-20 membered heterocyclyl substituted with one, two or more Ra; each Ra is identical or different and is each independently selected from halogen, $C_{1-40}$ alkyl, $C_{1-40}$ alkoxy, and $C_{6-20}$ arylacyl;

wherein $R_1$, $R_2$ and $R_3$ are identical or different and are each independently selected from hydrogen, $C_{1-40}$ alkyl, $C_{2-40}$ alkenyl, $C_{2-40}$ alkynyl, $C_{1-40}$ alkoxy, $C_{3-40}$ cycloalkyl, $C_{3-40}$ cycloalkyloxy, 3-20 membered heterocyclyl, $C_{6-20}$ aryl, 5-20 membered heteroaryl, and 3-20 membered heterocyclyl substituted with one, two or more Ra; each Ra is identical or different and is each independently selected from halogen, $C_{1-40}$ alkyl, $C_{1-40}$ alkoxy, and $C_{6-20}$ arylacyl.

According to an embodiment of the present disclosure, $R_1$, $R_2$ and $R_3$ are identical or different and are each independently selected from hydrogen, $C_{1-20}$ alkyl, $C_{2-20}$ alkenyl, $C_{2-20}$ alkynyl, CI-20 alkoxy, $C_{3-20}$ cycloalkyl, $C_{3-20}$ cycloalkyloxy, 5-10 membered heterocyclyl, $C_{6-14}$ aryl unsubstituted or substituted with Ra, 5-14 membered heteroaryl unsubstituted or substituted with Ra, and 5-14 membered heterocyclyl substituted with one, two or more Ra; each Ra is identical or different and is each independently selected from halogen, $C_{1-20}$ alkyl, $C_{1-20}$ alkoxy, and $C_{6-20}$ arylacyl. According to an embodiment of the present disclosure. $R_1$, $R_2$ and $R_3$ are identical or different and are each independently selected from hydrogen, $C_{1-20}$ alkyl, $C_{2-20}$ alkenyl, $C_{2-20}$ alkynyl, $C_{1-20}$ alkoxy, $C_{3-20}$ cycloalkyl, $C_{3-20}$ cycloalkyloxy, 5-10 membered heterocyclyl, $C_{6-14}$ aryl, 5-14 membered heteroaryl, and 5-14 membered heterocyclyl substituted with one, two or more Ra; each Ra is identical or different and is each independently selected from halogen, $C_{1-20}$ alkyl, $C_{1-20}$ alkoxy, and $C_{6-20}$ arylacyl.

According to an embodiment of the present disclosure, $R_1$, $R_2$ and $R_3$ are identical or different and are each independently selected from hydrogen, $C_{1-8}$ alkyl, $C_{2-8}$ alkenyl, $C_{2-8}$ alkynyl, alkoxy, $C_{3-8}$ cycloalkyl, $C_{3-8}$ cycloalkyloxy, 5-10 membered heterocyclyl, $C_{6-10}$ aryl unsubstituted or substituted with Ra. 5-10 membered heteroaryl unsubstituted or substituted with Ra, and 5-10 membered heterocyclyl substituted with one, two or more Ra; each Ra is identical or different and is each independently selected from $C_{6-10}$ arylacyl.

According to an embodiment of the present disclosure, $R_1$, $R_2$ and $R_3$ are identical or different and are each independently selected from hydrogen, $C_{1-8}$ alkyl, $C_{2-8}$ alkenyl, $C_{2-8}$ alkynyl, $C_{1-8}$ alkoxy, $C_{3-8}$ cycloalkyl, $C_{3-8}$ cycloalkyloxy, 5-10 membered heterocyclyl, $C_{6-10}$ aryl, 5-10 membered heteroaryl, and 5-10 membered heterocyclyl substituted with one, two or more Ra; each Ra is identical or different and is each independently selected from $C_{6-10}$ arylacyl.

According to an embodiment of the present disclosure, $R_1$, $R_2$ and $R_3$ are identical or different and are each independently selected from hydrogen, $C_{1-6}$ alkyl, $C_{2-6}$ alkenyl, $C_{2-6}$ alkynyl, $C_{1-6}$ alkoxy, $C_{3-6}$ cycloalkyl, $C_{3-6}$ cycloalkyloxy, 5-8 membered heterocyclyl, $C_{6-8}$ aryl unsubstituted or substituted with Ra, 5-8 membered heteroaryl unsubstituted or substituted with Ra, and 5-8 membered heterocyclyl substituted with one, two or more Ra; each Ra is identical or different and is each independently selected from $C_{6-10}$ arylacyl, such as benzoyl.

According to an embodiment of the present disclosure, $R_1$, $R_2$ and $R_3$ are identical or different and are each independently selected from hydrogen, $C_{1-6}$ alkyl, $C_{2-6}$ alkenyl, $C_{2-6}$ alkynyl, alkoxy, $C_{3-6}$ cycloalkyl, $C_{3-6}$ cycloalkyloxy, 5-8 membered heterocyclyl, $C_{6-8}$ aryl, 5-8 membered heteroaryl, and 5-8 membered heterocyclyl substituted with one, two or more Ra; each Ra is identical or different and is each independently selected from $C_{6-10}$ arylacyl, such as benzoyl.

According to an embodiment of the present disclosure, $R_1$ is selected from hydrogen, methyl, ethyl, isopropyl, isobutyl, tart-butyl, cyclopropyl, cyclobutyl, cyclopentyl and cyclohexyl; $R_2$ is selected from hydrogen, methyl, ethyl, isopropyl, isobutyl, tert-butyl, cyclopropyl, cyclobutyl, cyclopentyl and cyclohexyl; $R_3$ is selected from methyl, ethyl, isopropyl, Cert-butyl, isobutyl, n-butyl, n-pentyl, n-hexyl, cyclopropyl, cyclobutyl, cyclopentyl, cyclohexyl, methoxy, ethoxy, isopropoxy, tert-butoxy, isobutoxy, n-octyloxy, cyclopropyloxy, cyclobutoxy, cyclopentyloxy, cyclohexyloxy, and

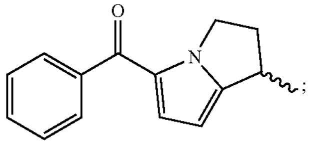 [SMILES: CC1CCn2c(C(=O)c3ccccc3)ccc21]

;

∿ indicates a connection site.

According to an embodiment of the present disclosure, the compound represented by formula (I) is preferably selected from the following structures:

N2

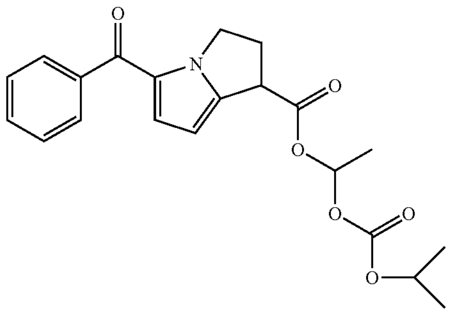

N3

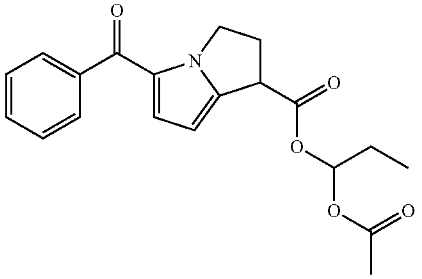

N4

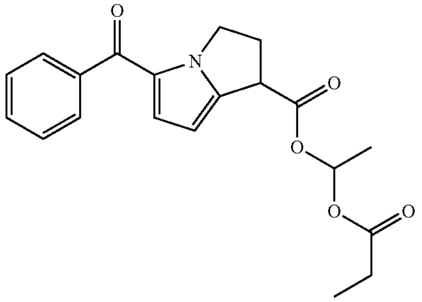

N5

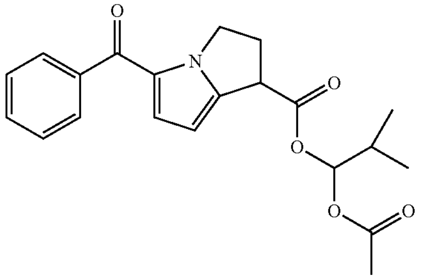

N6

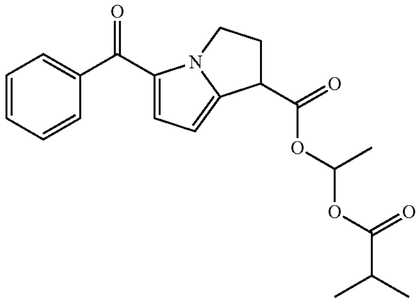

-continued
N7
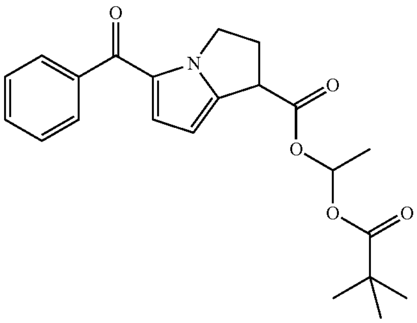
N8
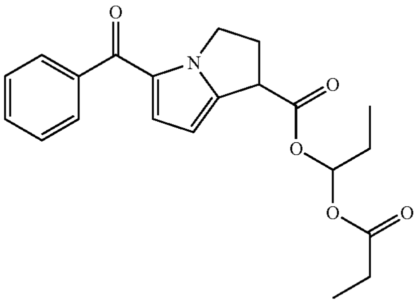
N9
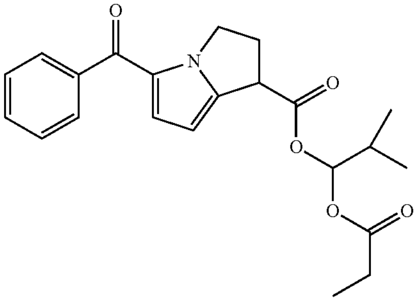
N10
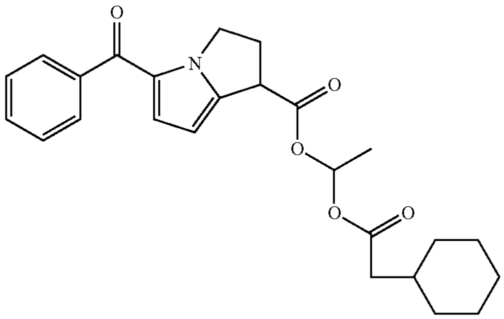
N12
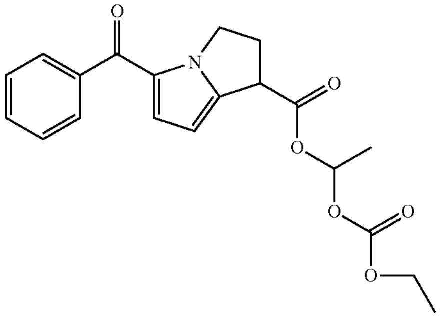
-continued
N13
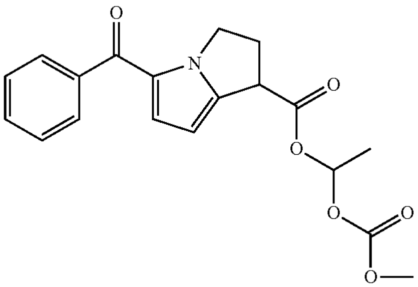
N14
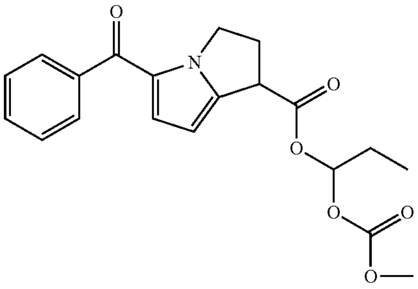
N15
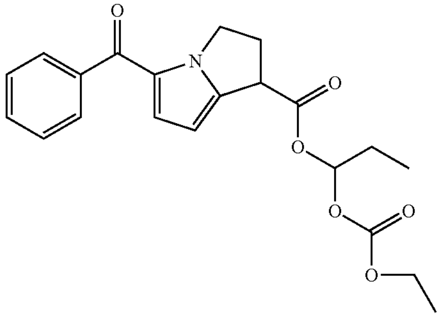
N16
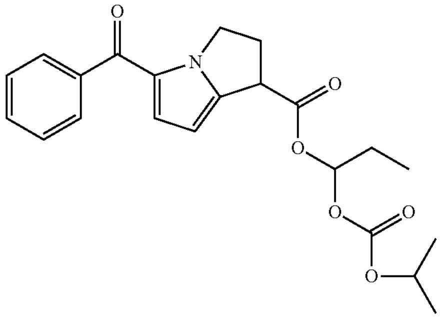
N17
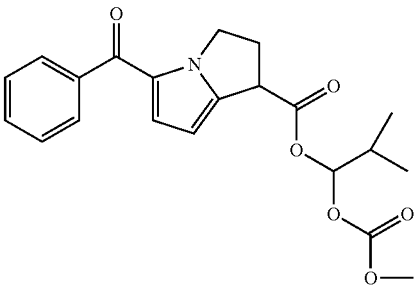

-continued
N18
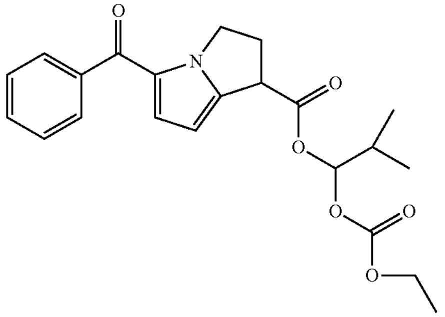
N19
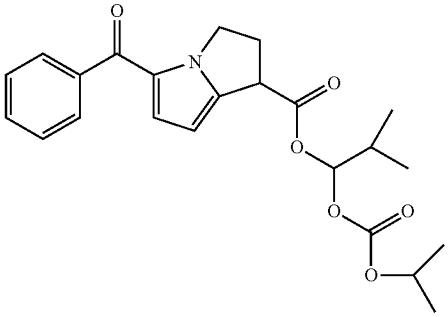
N20
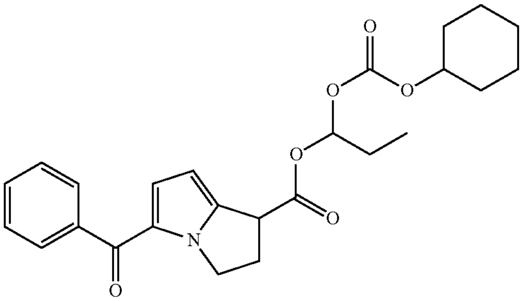
N21
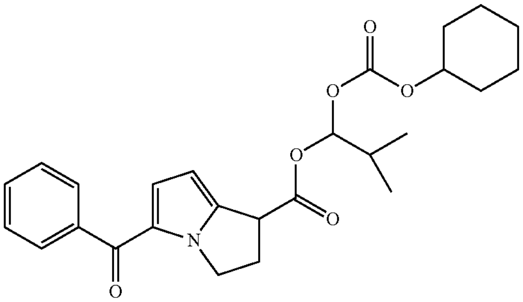
N22
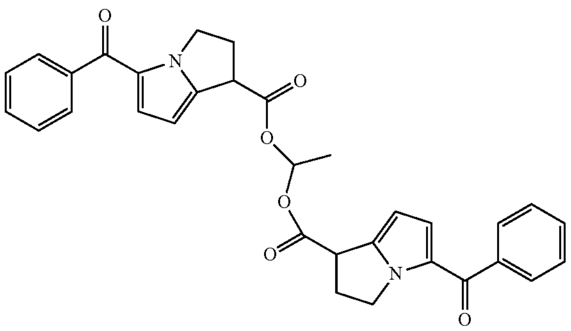
-continued
N26
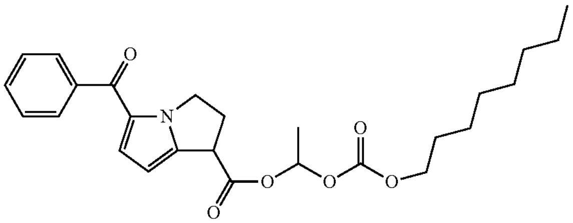
N27
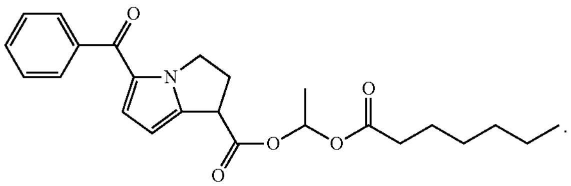
According to an embodiment of the present disclosure, the compound represented by formula (I) is more preferably selected from compounds N2, N3, N4, N8, N10, N12, N15, N16, N20, N21 and N22, and a levorotatory enantiomer selected from the following structures, i.e., an isomer with the carbon atom at position 1 being an S configuration:
N2(S)
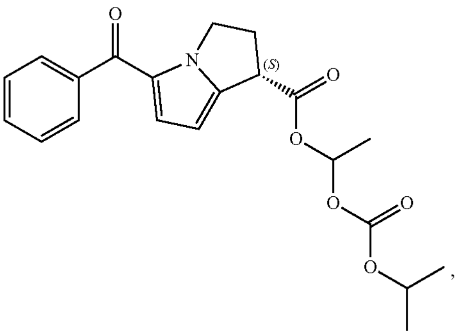
N8(S)
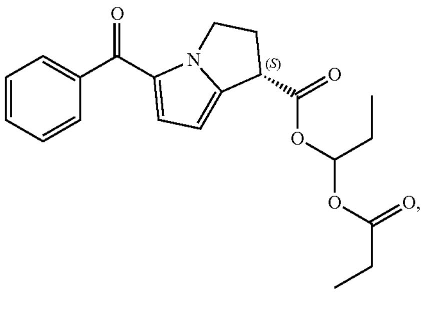

-continued

N12(S)

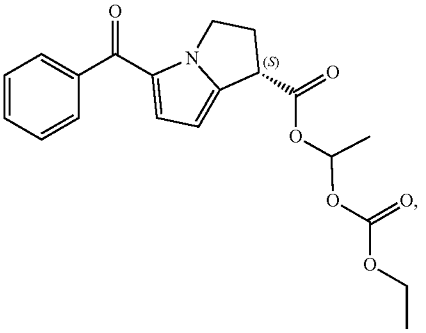

N15(S)

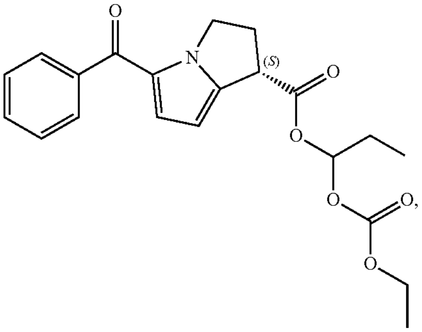

N16(S)

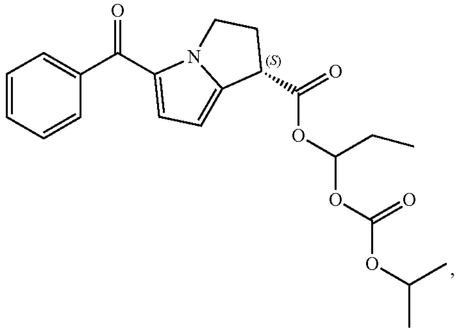

N10(S)

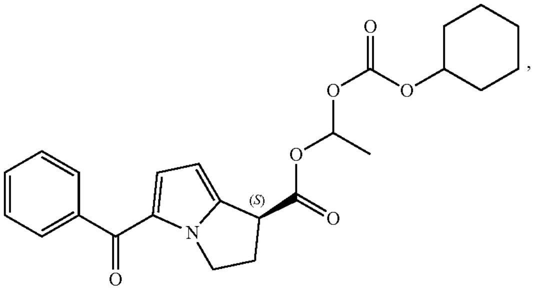

N20(S)

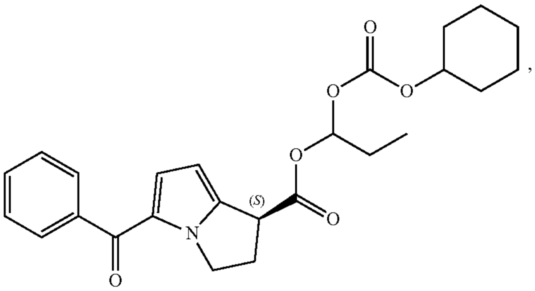

-continued

N21(S)

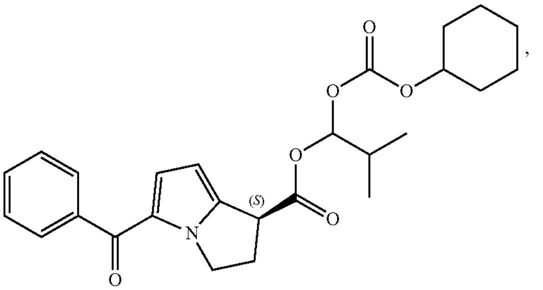

N22(S)

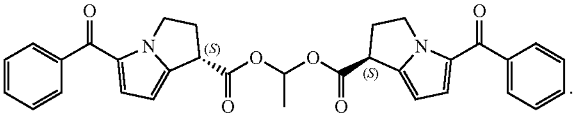

The inventor found that the specific compound represented by formula (I) has a metabolic pathway in a human body as follows:

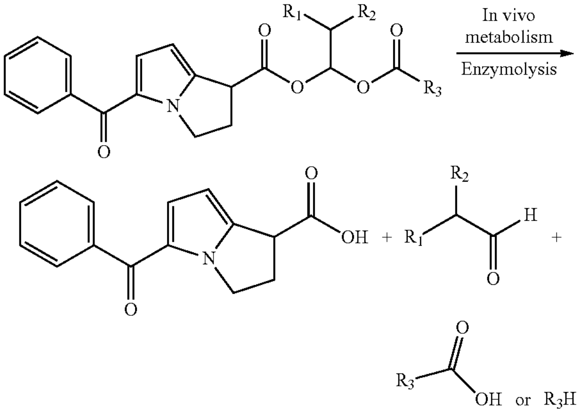

wherein $R_1$, $R_2$ and $R_3$ are all independently defined as above;

when $R_3$ is selected from $C_{1-40}$ alkoxy and $C_{3-40}$ cycloalkyloxy, methoxy, ethoxy, isopropoxy, tert-butoxy, isobutoxy, cyclopropyloxy, cyclobutoxy, cyclopentyloxy, and cyclohexyloxy, it can be metabolized to produce $R_3H$, and $R_3H$ can be finally metabolized to produce

further by alcohol dehydrogenase and aldehyde dehydrogenase (C atom in $R_3$ is connected to O via a double bond), that is:

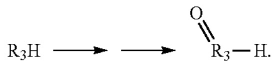

The second objective of the present disclosure is to provide a preparation method for the compound represented by formula (I) and the racemate, the stereoisomer, the pharmaceutically acceptable salt or the solvate thereof, comprising reacting the following compound 1 with compound 2 to give the compound represented by formula (I):

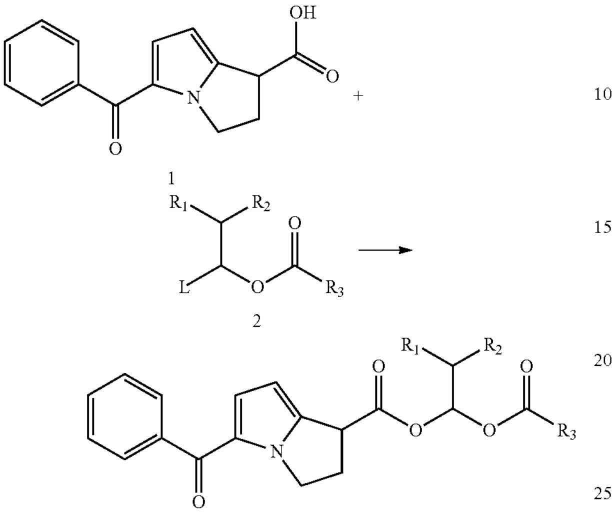

1

2

(I)

wherein $R_1$, $R_2$ and $R_3$ are all independently defined as above;

L is selected from leaving groups, such as halogen and hydroxy;

the compound 1 is selected from racemic ketorolac, and ketorolac having an R configuration and an S configuration, i.e., from (±)-5-benzoyl-2,3-dihydro-1H-pyrrolizine-1-carboxylic acid, (R)-5-benzoyl-2,3-dihydro-1H-pyrrolizine-1-carboxylic acid, and (S)-5-benzoyl-2,3-dihydro-1H-pyrrolizine-1-carboxylic acid.

According to an embodiment of the present disclosure, the compound 2 is selected from the following compound 3 and compound 4:

3

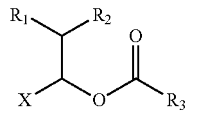

4

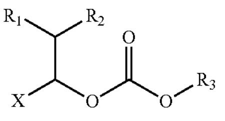

wherein all of $R_1$ and $R_3$ are independently defined as above; X is selected from chlorine, bromine and iodine.

According to an embodiment of the present disclosure, the preparation method can be performed in the presence of an organic solvent; for example, the organic solvent can be selected from at least one of the following: acetone, dimethyl sulfoxide, N,N-dimethylformamide, ethers, such as ethyl propyl ether, a n-butyl ether, anisole, phenetole, cyclohexyl methyl ether, dimethyl ether, diethyl ether, dimethyl ethylene glycol, diphenyl ether, dipropyl ether, diisopropyl ether, di-n-butyl ether, diisobutyl ether, diisopentyl ether, dimethoxyethane, isopropyl ethyl ether, methyl tert-butyl ether, tetrahydrofuran, methyl tetrahydrofuran, dioxane, dichlorodiethyl ether, and polyethers of ethylene oxide and/or propylene oxide; aliphatic, cycloaliphatic or aromatic hydrocarbons, such as pentane, hexane, heptane, octane, nonane, and hydrocarbons possibly substituted with fluorine and chlorine atoms, such as methylene chloride, dichloromethane, trichloromethane, carbon tetrachloride, fluorobenzene, chlorobenzene or dichlorobenzene; cyclohexane, methylcyclohexane, petroleum ether, octane, benzene, toluene, chlorobenzene, bromobenzene, and xylene; and esters, such as methyl acetate, ethyl acetate, butyl acetate, isobutyl acetate and dimethyl carbonate, dibutyl carbonate or ethylene carbonate.

According to an embodiment of the present disclosure, the preparation method may be performed in the presence of a acid binding agent, such as a base. The base may be an organic base or an inorganic base. For example, the inorganic base may be selected from at least one of the following: hydrides, hydroxides, alkoxides, acetates, fluorides, phosphates, carbonates and bicarbonates of alkali metals and alkaline earth metals; preferred bases are sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate and cesium carbonate; the organic base can be selected from at least one of the following: tertiary amities, substituted or unsubstituted pyridines and substituted or unsubstituted triethylamine, trimethylamine, N,N-diisopropylethylamine, tri-n-propylamine, tri-n-butylamine, tri-n-hexylamine, tricyclohexylatnine, N-methylcyclohexylamine, N-methylpyrrolidine, N-methylpiperidine, N-ethylpiperidine, N,N-dimethylaniline, N-methylmorpholine, pyridine, 2,3- or 4-methylpyridine, 2-methyl-5-ethylpyridine, 2,6-dimethylpyridine, 2,4,6-trimethylpyridine, 4-dimethylaminopyridine, quinoline, methylquinoline, N,N,N,N-tetramethylethylenediamine, N,N-dimethyl-1,4-diazacyclohexane, N,N-diethyl-1,4-diazabicyclocyclohexane, 1,8-bis(dimethylamino) naphtlialene, diazabicyclooctane (DABCO), diazabicyclononane (DBN), diazabicycloundecane (DBU), butylimidazole and methylimidazole.

According to an embodiment of the present disclosure, the preparation method may be performed in the presence of a catalyst, for example a phase transfer catalyst; the catalyst may be selected from tetrabutylammonium bromide (TBAB), tetrabutyl ammonium chloride (TBAC), tetrabutylammonium iodide (TBAI), potassium iodide, sodium iodide and 18-crown-6 ether.

According to an embodiment of the present disclosure, a reaction temperature of the preparation method is −5-80° C., for example, 0-50° C., and illustratively 10° C., 20° C., 25° C., 30° C. or 40° C. According to an embodiment of the present disclosure, a reaction time of the preparation method is 0.5-24 h, for example, 1-12 h, and illustratively 1 h, 2 h, 3 h, 4 h, 5 h or 6 h.

The present disclosure provides a preparation method for a compound 3, comprising reacting a compound 3-1 with a compound 3-2 to give the compound 3;

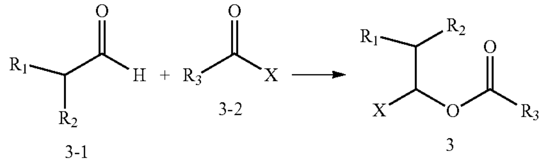

3-1

3-2

3 wherein X is selected from chlorine, bromine and iodine; $R_1$, $R_2$ and $R_3$ are as defined above.

According to an embodiment of the present disclosure, the preparation method may be performed in the presence of a catalyst; the catalyst may be zinc chloride.

According to an embodiment of the present disclosure, the preparation method may be performed in the presence of a solvent; the solvent may be selected from at least one of acetone, dichloromethane, trichloromethane, carbon tetrachloride and diethyl ether;

According to an embodiment of the present disclosure, the reaction temperature of the preparation method is −5-80° C., for example, 20-60° C.

According to an embodiment of the present disclosure, the reaction time of the preparation method is 1-8 h, for example, 2-6 h.

According to an embodiment of the present disclosure, the preparation method also comprises a post-treatment step, for example, the reaction solution is concentrated to remove the solvent, followed by washing, concentration or distillation to give the compound 3.

The present disclosure also provides a preparation method for a compound 4, comprising the following reaction steps: when X in the structure of the compound 4 is chlorine or iodine, the synthesis method comprises:

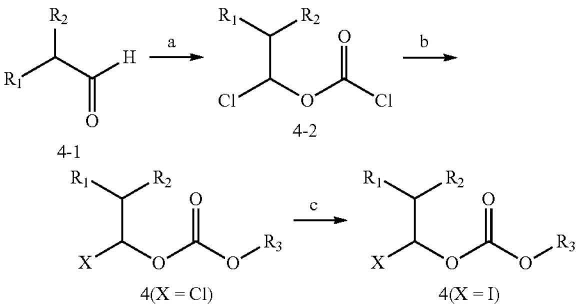

4-1, 4-2, 4(X = Cl), 4(X = I)

a) reacting a compound 4-1 with triphosgene to give a compound 4-2 in the form of chloroformate;

b) reacting the compound 4-2 with an alcohol $R_3$—OH to give chloro-organic carbonate, namely a compound 4 (X═Cl); and c) reacting the compound 4 (X═Cl) with NaI to give iodo-organic carbonate, namely a compound 4 (X═I);

when X in the structure of the compound 4 is bromine, the synthesis method comprises:

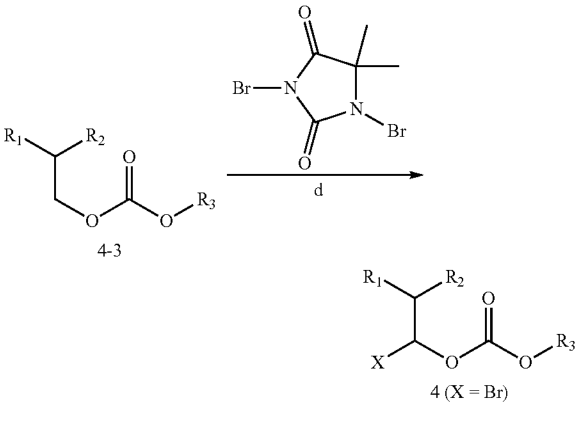

4-3, 4 (X = Br)

reacting a compound 4-3 (organic carbonic diester) with dibromohydantoin to give bromo-organic carbonate, namely a compound 4 (X═Br);

wherein $R_1$, $R_2$ and $R_3$ are defined as above.

According to an embodiment of the present disclosure, the reactions in the step a) and the step b) may be performed in the presence of a solvent; the solvent is selected from at least one of acetone, dichloromethane, trichloromethane, carbon tetrachloride and diethyl ether.

According to an embodiment of the present disclosure, the reactions in the step a) and the step b) may be performed in the presence of a acid binding agent, such as a base; the acid binding agent may be selected from at least one of pyridine, triethylamine, DIEA, NaOH, KOH, $K_2CO_3$, $KHCO_3$, $NaCO_3$ and $NaHCO_3$.

According to an embodiment of the present disclosure, the reaction time of the preparation method is 0.5-3 h, for example, 1-2 h.

According to the embodiment of the present disclosure, in the step a), the compound 4-1 is reacted in a low-temperature environment under $N_2$ atmosphere. Furthermore, the method also comprises the step of exhausting under reduced pressure (absorbing the exhausted gas by alkali liquor), concentrating the residual liquid under reduced pressure at room temperature to remove the solvent, and then performing a distillation method to give the compound 4-2.

According to an embodiment of the present disclosure, in the step b), the compound 4-2 is reacted with an alcohol under anhydrous and oxygen-free solvent conditions. Preferably, under an ice bath condition, an acid binding agent is added to give the compound 4.

According to an embodiment of the present disclosure, the method also comprises a post-treatment step, for example, the reaction solution is washed, dried and concentrated under reduced pressure to give compound 4.

The third objective of the present disclosure is to provide use of the compound represented by formula (I) and the racemate, the stereoisomer, the pharmaceutically acceptable salt or the solvate thereof for the manufacturing of a non-steroidal anti-inflammatory medicament.

According to the present disclosure, the drug may be used for anti inflammation and/or analgesia in rheumatoid arthritis, lumbago, migraine, neuralgia, scapulohumeral periarthritis, osteoarthritis, and neck-shoulder-wrist syndrome, analgesia and/or anti inflammation after surgery, trauma or tooth extraction, and relieving fever and/or analgesia in acute upper respiratory tract inflammation.

Yet another objective of the present disclosure is to provide a pharmaceutical composition comprising the compound represented by formula (I) and the racemate, the stereoisomer, the pharmaceutically acceptable salt or the solvate thereof.

The present disclosure also provides a pharmaceutical composition comprising a therapeutically effective amount of the compound represented by formula (I) and the racemate, the stereoisomer, the pharmaceutically acceptable salt or the solvate thereof.

According to an embodiment of the present disclosure, the pharmaceutical composition also comprises one or more pharmaceutically acceptable auxiliary materials.

According to an embodiment of the present disclosure, the pharmaceutical composition is in the form of a formulation. Furthermore, the formulation is an oral formulation, such as tablets, capsules, injections, eye drops, nasal drops, sprays, gels, creams, ointments, cataplasms, or the like.

According to an embodiment of the present disclosure, the pharmaceutical composition may further comprise one or more additional therapeutic agents.

The present disclosure also provides a method for anti inflammation and/or analgesia in rheumatoid arthritis, lumbago, migraine, neuralgia, scapulohumeral periarthritis, osteoarthritis, and neck-shoulder-wrist syndrome, analgesia and/or anti inflammation after surgery, trauma or tooth extraction, and relieving fever and/or analgesia in acute upper respiratory tract inflammation, comprising administering a prophylactically or therapeutically effective amount of at least one of the compound represented by formula (I) and the racemate, the stereoisomer, the pharmaceutically acceptable salt or the solvate thereof to a patient.

In some embodiments, the patient is a human.

The present disclosure also provides the compound represented by formula (I) and the racemate, the stereoisomer, the pharmaceutically acceptable salt or the solvate thereof, or the pharmaceutical composition thereof, for anti inflammation and/or analgesia in rheumatoid arthritis, lumbago, migraine, neuralgia, scapulohumeral periarthritis, osteoarthritis, and neck-shoulder-wrist syndrome, analgesia and/or anti inflammation after surgery, trauma or tooth extraction, and relieving fever and/or analgesia in acute upper respiratory tract inflammation.

When used as a drug, the compound of the present disclosure may be administered in the form of a pharmaceutical composition. These compositions may be formulated in a manner well known in the pharmaceutical arts and may be administered by a variety of routes depending on whether local or systemic treatment is desired and the area to be treated. The administration can be performed topically (e.g., transdermal, dermal, ocular, and mucosal including intranasal, vaginal, and rectal delivery), pulmonarily (e.g., by inhalation or insufflation of powders or aerosols, including by nebulizer; intratracheal, intranasal), orally, or parenterally. Parenteral administration includes intravenous, intraarterial, subcutaneous, intraperitoneal or intramuscular injection or infusion; or intracranial administration, e.g., intrathecal or intracerebroventricular administration. The administration may be performed parenterally in a single bolus form, or may be performed by, for example, continuous infusion pump. Pharmaceutical compositions and formulations for topical administration may comprise transdermal patches, ointments, lotions, creams, gels, drops, suppositories, sprays, liquids, fat emulsion injections and powders. Conventional pharmaceutical carriers, water, powders or oily matrices, thickeners and the like may be necessary or desirable.

In the preparation of the pharmaceutical composition of the present disclosure, the active ingredient is typically mixed with an excipient, diluted with an excipient or encapsulated within such a carrier, for example, in the form of a capsule, sachet, paper or other containers. When the excipient serves as a diluent, it may be a solid, semi-solid, or liquid material that serves as a vehicle, carrier, or medium for the active ingredient. Thus, the composition may be in the form of the following: tablets, pills, powders, capsules, injections, lozenges, sachets, cachets, elixirs, suspensions, emulsions, solutions, eye drops, syrups, gels, ointments, aerosols (solid or dissolved in a liquid vehicle) or cataplasms; ointments, soft and hard gelatin capsules, suppositories, sterile injectable solutions and sterile packaged powders containing, for example, up to 10% by weight of active compound.

Some examples of suitable excipients include lactose, dextrose, sucrose, sorbitol, mannitol, starches, acacia, calcium phosphate, alginates, tragacanth, gelatin, calcium silicate, microcrystalline cellulose, polyvinylpyrrolidone, cellulose, water, syrup, and methylcellulose. The formulation may also comprise: a lubricant, such as talc, magnesium stearate and mineral oil; a wetting agent; an emulsifier and a suspending agent; a preservative, such as methyl benzoate and hydroxypropyl benzoate; a sweetening agent and a flavoring agent. The composition of the present disclosure may be formulated by using methods known in the art so as to provide immediate release, sustained release or delayed release of the active ingredient after administration to the patient.

The composition may be formulated in a unit dosage form containing about 5-1000 mg, more typically about 1100-500 mg, of the active ingredient per dose. The term “unit dosage form” refers to a physically discrete single dosage unit suitable for use in human patients and other mammals, each unit containing a predetermined amount of active substance calculated to produce a desired therapeutic effect, in association with a suitable pharmaceutical excipient.

The effective dosage of the active compound may vary widely and is generally administered in a pharmaceutically effective amount. It can be understood, however, that the amount of the compound actually administered is generally determined by a physician, in the light of the relevant circumstances, including the condition to be treated, the chosen route of administration, the actual compound administered; age, weight and response of the individual patient; severity of patient symptoms, and the like.

For preparing a solid composition such as a tablet, the principal active ingredient is mixed with a pharmaceutical excipient to form a solid preformulation composition comprising a homogeneous mixture of the compound of the present disclosure. When referring to these preformulation compositions as homogeneous, it is meant that the active ingredient is generally distributed evenly throughout the composition such that the composition may be readily divided into equally effective unit dosage forms such as tablets, pills and capsules. The solid preformulation is then divided into unit dosage forms of the type described above containing, for example, about 0.1-1000 mg of the active ingredient of the present disclosure.

The tablets or pills of the present disclosure may be coated or compounded to provide a dosage form affording the advantage of prolonged action. For example, a tablet or pill contains components with an inner dosage and an outer dosage, the latter being in the coated form of the former. The two components may be separated by an enteric-coated layer which serves to resist disintegration in the stomach, such that the inner component is allowed to pass through the duodenum completely or to be delayed in release. A variety of materials may be used for such enteric-coated layers or coatings, such materials including various polymeric acids and mixtures of polymeric acids with such materials as shellac, cetanol and cellulose acetate.

Liquid forms in which the compound and the composition of the present disclosure may be incorporated for administration orally or by injection include aqueous solutions, suitably flavoured syrups, aqueous or oil suspensions; and emulsions formulated with edible oils such as cottonseed oil, sesame oil, medium-chain oil, coconut oil or peanut oil; and elixirs and similar pharmaceutical vehicles.

Compositions for inhalation or insufflation include solutions, suspensions and powders dissolved in pharmaceutically acceptable water or organic solvents or mixtures thereof. The liquid or solid compositions may contain suitable pharmaceutically acceptable excipients as described above. In certain embodiments, the composition is administered by the oral or nasal respiratory route to achieve a local or systemic effect. The composition may be atomized by using an inert gas. The atomized solution may be inhaled directly by an atomizing device, or the atomizing device may be connected to a mask or an intermittent positive pressure ventilator. The solution, suspension or powder compositions may be administered orally or nasally by means of a device which delivers the formulation in a suitable manner.

The amount of the compound or composition administered to a patient is not fixed and depends on the drug administered, the purpose of administration such as prevention or treatment; the condition of the patient, the mode of administration, and the like. In therapeutic use, compositions may be administered to a patient already suffering from a disease in an amount sufficient to cure or at least partially arrest the symptoms of the disease and its complications. The effective dosage may depend on the disease state being treated and the determination of the attending clinician, the determination depending on factors such as the severity of the disease, the age, weight and general condition of the patient, and the like.

The composition administered to the patient may be in the form of the pharmaceutical composition as described above. These compositions may be sterilized by conventional sterilization techniques or may be sterilized by filtration. The aqueous solutions may be packaged for use in an original shape, or lyophilized, and the lyophilized formulation is mixed with a sterile aqueous carrier prior to administration. The pH of the compound formulation is usually 3-11, more preferably 5-9, and most preferably 7-8. It can be appreciated that the use of certain aforementioned excipients, carriers or stabilizers may result in the formation of a pharmaceutical salt.

The therapeutic dosage of the compound of the present disclosure may be determined, for example, by: the specific use of the treatment, the mode of administration of the compound, the health and condition of the patient, and the determination of the prescribing physician. The proportion or concentration of the compound of the present disclosure in the pharmaceutical composition may not be fixed and depends on a variety of factors including the dosage, chemical properties (e.g., hydrophobicity), and the route of administration. For example, the compound of the present disclosure may be provided for parenteral administration by a physiological buffered aqueous solution containing about 0.1-10% w/v of the compound. A certain typical dosage range is about 1 μg/kg to about 1 g/kg body weight/day. In certain embodiments, the dosage range is about 0.01 mg/kg to about 100 mg/kg body weight/day. The dosage is more than likely to depend upon such variables as the type and extent of progression of the disease or condition, the general health status of the particular patient, the relative biological potency of the compound selected, the excipient formulation and its route of administration. Effective doses may be obtained by extrapolation from dose-response curves derived from in vitro or animal model test systems.

Beneficial Effects

1) The present disclosure designs and prepares a series of ketorolac derivatives by derivatizing the carboxyl of racemic ketorolac to overcome the problems of short half-life period, poor stability, irritation, compatibility and the like of ketorolac which commonly exist at present. The compounds of the present disclosure has good pharmacokinetic properties demonstrated through in vitro plasma tests. In addition, the physical and chemical stability of the compound itself is high, for example, the purity of the compound is basically kept unchanged in a high-temperature test (placing for 5-10 days at 60° C.) for influencing factor investigation.

2) The main pharmacological activity of ketorolac is derived from levorotatory ketorolac, wherein a levorotatory ketorolac ester derivative with (IS) configuration is directionally synthesized by taking the levorotatory ketorolac as a starting material, and further experiments show that related substances and the corresponding levorotatory isomer of the ketorolac derivative may be kept at higher stability in an oil phase for 30 days when placed at different temperatures.

3) The side chains of a series of ketorolac derivatives prepared in the present disclosure contain carbonate structures, so that the fat solubility thereof are improved, and the structures are beneficial to improving the absorption efficiency of the compounds in the gastrointestinal tract after oral administration, thereby increasing the bioavailability of the drug.

DEFINITIONS AND DESCRIPTION

Figure 1:
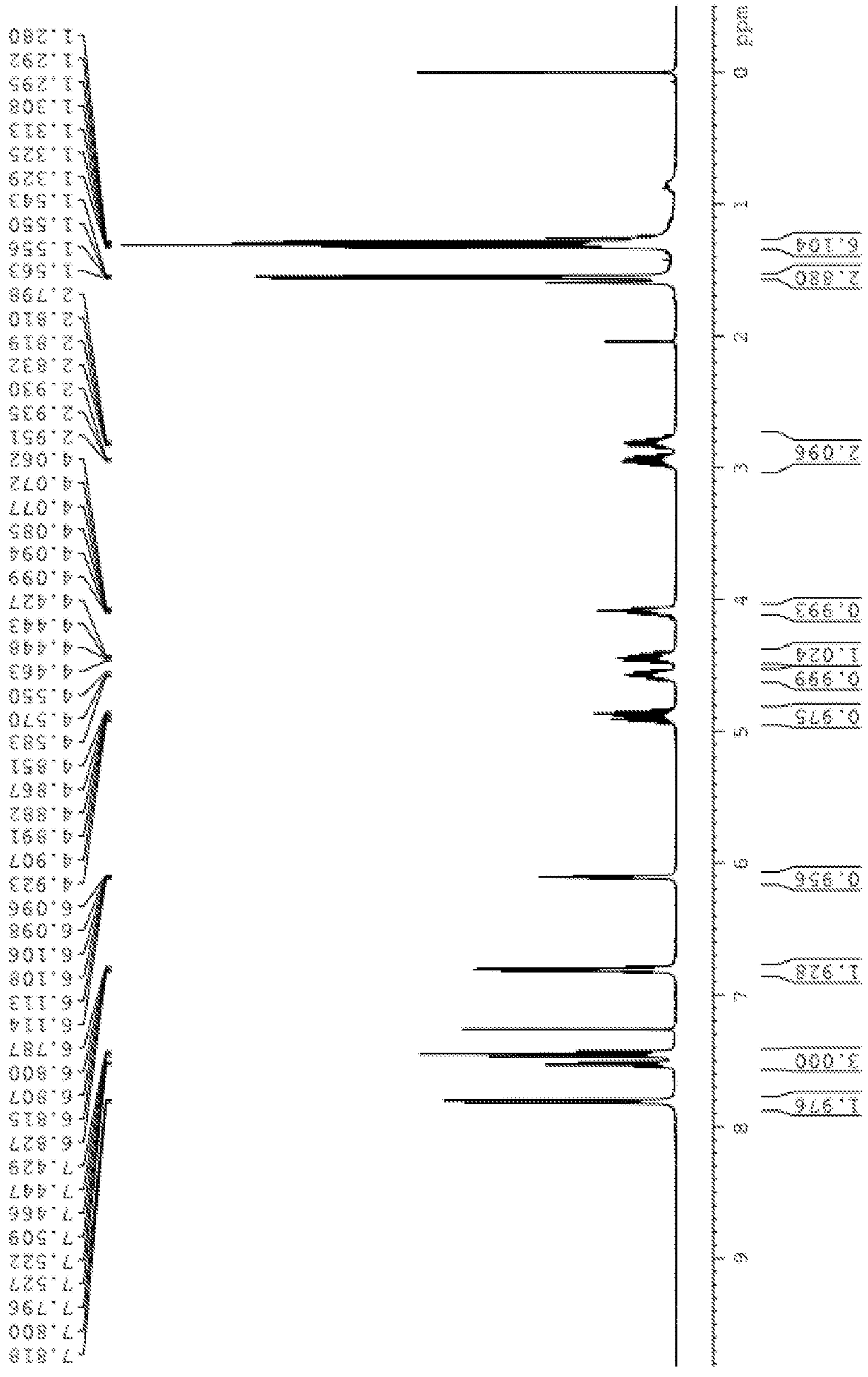
FIG. 1 is a hydrogen spectrum of the compound N2 of the present disclosure.

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification.

Unless otherwise stated, a numerical range set forth in the description and claims shall be construed as at least including each specific integer within the range. For example, the numerical range "1-40" is equivalent to recording each integer value in the numerical range "1-10", i.e., 1, 2, 3, 4, 5, 6, 7, 8, 9 and 10, and each integer value in the numerical range "11-40", i.e., 11, 12, 13, 14, 15, . . . , 35, 36, 37, 38, 39 and 40. It should be understood that when one, two or more are used to describe a substituent herein, "more" shall mean an integer ≥3, such as 3, 4, 5, 6, 7, 8, 9 or 10. In addition, when a certain numerical range is defined as "numbers", it shall be construed as recording both endpoints of the range, each integer within the range, and each decimal within the range. For example, "numbers of 0-10" shall be construed as including not only each of integers 0, 1, 2, 3, 4, 5, 6, 7, 8, 9 and 10, but also at least the sums of each integer and 0.1, 0.2, 0.3, 0.4, 0.5, 0.6, 0.7, 0.8 or 0.9.

The term "halogen" refers to fluorine, chlorine, bromine and iodine.

The term "$C_{1-40}$ alkyl" preferably refers to a linear or branched saturated monovalent hydrocarbyl group having 1-40 carbon atoms. For example, "$C_{1-10}$ alkyl" refers to a linear or branched alkyl group having 1, 2, 3, 4, 5, 6, 7, 8, 9 or 10 carbon atoms and "$C_{1-6}$ alkyl" refers to a linear or branched alkyl group having 1, 2, 3, 4, 5 or 6 carbon atoms. The alkyl is, for example, methyl, ethyl, propyl, butyl, pentyl, hexyl, isopropyl, isobutyl, sec-butyl, tert-butyl, isopentyl, 2-methylbutyl, 1-methybutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl, etc., or isomers thereof.

The term "$C_{2-40}$ alkenyl" preferably refers to a linear or branched monovalent hydrocarbyl comprising one or more double bonds and having 2-40 carbon atoms, preferably "$C_{2-10}$ alkenyl". The "$C_{2-10}$ alkenyl" preferably refers to a linear or branched monovalent hydrocarbyl comprising one or more double bonds and having 2, 3, 4, 5, 7, 8, 9 or 10 carbon atoms, for example, having 2, 3, 4, 5 or 6 carbon atoms (i.e., $C_{2-6}$ alkenyl) or having 2 or 3 carbon atoms (i.e., $C_{2-3}$ alkenyl). It should be understood that in the case that the alkenyl comprises more than one double bond, the double bonds can be separated from one another or conjugated. The alkenyl is, for example, vinyl, allyl, (E)-2-methylvinyl, (Z)-2-methylvinyl, (E)-but-2-enyl, (Z)-but-2-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methybut-1-enyl, (Z)-3-methylbut-1-enyl, (E)-2-methybut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl or 1-isopropylvinyl.

The term "$C_{2-40}$ alkynyl" refers to a linear or branched monovalent hydrocarbyl comprising one or more triple bonds and having 2-40 carbon atoms, preferably "$C_{2-10}$ alkynyl". The term "$C_{2-10}$ alkynyl" preferably refers to a linear or branched monovalent hydrocarbyl comprising one or more triple bonds and having 2, 3, 4, 5, 6, 7, 8, 9 or 10 carbon atoms, for example, having 2, 3, 4, 5 or 6 carbon atoms (i.e., "$C_{2-6}$ alkynyl") or having 2 or 3 carbon atoms ("$C_{2-3}$ alkynyl"). The alkynyl is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethyl prop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropyl-prop-2-ynyl, 2,2-dimethylbut-3-ynyl, 1,1-dimethylbut-3-ynyl, 1,1-dimethylbut-2-ynyl or 3,3-dimethylbut-1-ynyl. In particular, the alkynyl is ethynyl, prop-1-ynyl or prop-2-ynyl.

The term "$C_{3-40}$ cycloalkyl" refers to a saturated monovalent monocyclic or bicyclic hydrocarbon ring or bridged cycloalkane having 3-40 carbon atoms, preferably "$C_{3-40}$ cycloalkyl". The term "$C_{3-10}$, cycloalkyl" refers to a saturated monovalent monocyclic or bicyclic hydrocarbon ring or bridged cycloalkane having 3, 4, 5, 6, 7, 8, 9 or 10 carbon atoms. The $C_{3-10}$ cycloalkyl may be a monocyclic hydrocarbyl such as cyclopropyl, cyclobutyl, cyclopentyl, cyclohexyl, cycloheptyl, cyclooctyl, cyclononyl or cyclodecyl, or may be a bicyclic hydrocarbyl such as a decahydronaphthalene ring. The term "3-20 membered heterocyclyl" refers to a saturated monovalent monocyclic or bicyclic hydrocarbon ring or bridged cycloalkane, which is a non-aromatic cyclic group with a total number of 3-20 (such as 3, 4, 5, 6, 7, 8, 9 and 10) ring atoms comprising 1-5 heteroatoms independently selected from N, O and S, preferably a "3-10 membered heterocyclyl". The term "3-10 membered heterocyclyl" refers to a saturated monovalent monocyclic or bicyclic hydrocarbon ring or bridged cycloalkane comprising 1-5, preferably 1-3, heteroatoms selected from N, O and S. The heterocyclyl may be connected to the rest of the molecule through any of the carbon atoms or the nitrogen atom (if present). In particular, the heterocyclyl may include, but is not limited to: 4-membered rings such as azetidinyl and oxetanyl; 5-membered rings such as tetrahydrofuranyl, dioxolyl, pyrrolidinyl, imidazolidinyl, pyrazolidinyl and pyrrolinyl; 6-membered rings such as tetrahydropyranyl, piperidyl, morpholinyl, dithianyl, thiomotpholinyl, piperazinyl and trithianyl; or 7-membered rings such as diazepanyl. Optionally, the heterocyclyl may be benzo-fused. The heterocyclyl may be bicyclic, for example, but not limited to, a 5,5-membered ring such as pyrrolizine, a hexahydrocyclopenta[c]pyrrol-2(1H)-yl ring, or a 5,6-membered bicyclic ring such as a hexahydropyrrolo[1,2-a]pyrazin-2(1H)-yl ring. The ring containing nitrogen atoms may be partially unsaturated, i.e., it may contain one or more double bonds, for example, but not limited to, 2,5-dihydro-1H-pyrrolyl, 4H-[1,3,4]thiadiazinyl, 4,5-dihydrooxazolyl or 4H-[1,4]thiazinyl, or it may be benzo-fused, for example, but not limited to, dihydroisoquinolyl. According to the present disclosure, the heterocyclyl is non-aromatic. When the 3-20 membered heterocyclyl is connected to another group to form the compound of the present disclosure, the group may be connected to the carbon atom on the 3-20 membered heterocyclyl, or may be connected to the heteroatom on the 3-20 membered heterocyclyl. For example, when the 3-20 membered heterocyclyl is selected from piperazinyl, the group may be connected to the nitrogen atom on the piperazinyl. Alternatively, when the 3-20 membered heterocyclyl is selected from piperidinyl, the group may be connected to the nitrogen atom on the piperidinyl or the carbon atom in the para position.

The term "$C_{6-20}$ aryl" preferably refers to an aromatic or partially aromatic monovalent monocyclic, bicyclic or tricyclic hydrocarbon ring having 6-20 carbon atoms, preferably "$C_{6-14}$ aryl". The term "$C_{6-14}$ aryl" preferably refers to an aromatic or partially aromatic monovalent monocyclic, bicyclic or tricyclic hydrocarbon ring having 6, 7, 8, 9, 10, 11, 12, 13 or 14 carbon atoms ("$C_{6-14}$ aryl"), in particular a ring having 6 carbon atoms ("$C_6$ aryl"), such as phenyl or biphenyl, a ring having 9 carbon atoms ("$C_9$ aryl"), such as indanyl or indenyl, a ring having 10 carbon atoms ("$C_{10}$ aryl"), such as tetrahydronaphthyl, dihydronaphthyl or naphthyl, a ring having 13 carbon atoms ("$C_{13}$ aryl"), such as fluorenyl, or a ring having 14 carbon atoms ("$C_{14}$ aryl"), such as anthryl. When the $C_{6-20}$ aryl is substituted, it may be monosubstituted or polysubstituted. In addition, the substitution site is not limited, and may be, for example, ortho-substitution, para-substitution, or meta-substitution.

The term "5-20 membered heteroaryl" refers to a monovalent aromatic monocyclic, bicyclic or tricyclic ring system which has 5-20 ring atoms and comprises 1-5 heteroatoms independently selected from N, O and S, such as "5-14 membered heteroaryl". The term "5-14 membered heteroaryl" refers to a monovalent aromatic monocyclic, bicyclic or tricyclic ring system which has 5, 6, 7, 8, 9, 10, 11, 12, 13 or 14 ring atoms, in particular 5, 6, 9 or 10 carbon atoms, comprises 1-5, preferably 1-3 heteroatoms each independently selected from N, O and S, and may be benzo-fused in each case. In particular, the heteroalyl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and the like, and benzo derivatives thereof such as benzofuranyl, benzothienyl, benzoxazolyl, benzoisoxazolyl, benzimidazolyl, benzotriazolyl, indazolyl, indolyl, and isoindolyl; or pyridinyl, pyridazinyl, pyrimidinyl, pyrazinyl, triazinyl and the like, and benzo derivatives thereof such as quinolyl, quinazolinyl, and isoquinolyl; or azocinyl, indolizinyl, purinyl and the like, and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, and the like. When the 5-20 membered heteroaryl is connected to another group to form the compound of the present disclosure, the group may be connected to the carbon atom on the 5-20 membered heteroaryl ring, or may be connected to the heteroatom on the 5-20 membered heteroaryl ring. When the 5-20 membered heteroaryl is substituted, it may be monosubstituted or polysubstituted. In addition, the substitution site is not limited. For example, hydrogen connected to the carbon atom on the heteroaryl ring may be substituted, or hydrogen connected to the heteroatom on the heteroaryl ring may be substituted.

Unless otherwise stated, the heterocyclyl, heteroaryl or heteroarylene includes all possible isomeric forms thereof, e.g., positional isomers thereof. Thus, for some illustrative non-limiting examples, forms that involving substitutions at or bonding to other groups at one, two or more of positions 1, 2, 3, 4, 5, 6, 7, 8, 9, 10, 11, 12 and the like (if present) are included, including pyridin-2-yl, pyridinylene-2-yl, pyridin-3-yl, pyridinylene-3-yl, pyridin-4-yl and pyridinylene-4-yl; thienyl or thienylene, including thien-2-yl, thien-2-ylene, thien-3-yl, and thien-3-ylene; pyrazol-1-yl, pyrazol-3-yl, pyrazol-4-yl and pyrazol-5-yl.

Unless otherwise indicated, the definitions of the terms herein are also applicable to groups comprising the terms, e.g., the definition of $C_{1-40}$ cycloalkyl is also applicable to $C_{1-40}$ cycloalkyloxy. It can be understood by those skilled in the art that the compound represented by formula (I) may exist in the form of various pharmaceutically acceptable salts. If these compounds have basic centers, they can form acid addition salts; if these compounds have acidic centers, they can form base addition salts; if these compounds contain both acidic centers (e.g., carboxyl) and basic centers (e.g., amino), they can also form internal salts. Acid addition salts include, but are not limited to: hydrochloride, hydrofluoride, hydrobromide, hydroiodide, sulphate, pyrosulphate, phosphate, nitrate, methanesulphonate, ethanesulphonate, 2-hydroxyethanesulphonate, benzenesulphonate, toluenesulphonate, sulphamate, 2-naphthalenesulphonate, formate, acetoacetic acid, pyruvic acid, laurate, cinnamate, benzoate, acetate, di hydroxyacetate, trifluoroacetate, pivalate, propionate, butyrate, hexanoate, heptanoate, undecanoate, stearate, ascorbate, camphorate, camphorsulphonate, citrate, fumarate, malate, maleate, hydroxymaleate, oxalate, salicylate, succinate, gluconate, quinate, pamoate, glycolate, tartrate, lactate, 2-(4-hydroxybenzoyl)benzoate, cyclopentanepropionate, digluconate, 3-hydroxy-2-naphthoate, nicotinate, embonate, pectinate, 3-phenylpropionate, picrate, pivalate, itaconate, triflate, dodecyl sulfate, p-toluenesulfonate, napadisylate, malonate, adipate, alginate, mandelate, glucoheptonate, glycerophosphate, sulfosalicylate, hemisulfate or thiocyanate, aspartate, and the like; base addition salts, such as alkali metal salts, alkaline earth metal salts, ammonium salts and the like, specifically include, but are not limited to: sodium salt, lithium salt, potassium salt, ammonium salt, aluminum salt, magnesium salt, calcium salt, barium salt, iron salt, ferrous salt, manganese salt, manganous salt, zinc salt, ammonium salt (including salt with $NH_3$ and organic amine $NH_4$ salt), methylammonium salt, trimethylammonium salt, diethylammonium salt, triethylammonium salt, propylamine salt, tripropylammonium salt, isopropylammonium salt, tert-butyl ammonium salt, N,N'-dibenzylethylenediamine salt, dicyclohexylammonium salt, 1,6-hexadimethrine ammonium salt, benzylammonium salt, ethanolamine salt, N,N-dimethylethanolamine salt, N,N-diethylethanolamine salt, triethanolamine salt, tromethamine salt, lysine salt, arginine salt, hi stidine salt, glucose ammonium salt, N-methylglucamine salt, dimethylglucammonium salt, ethylgucammonium salt, meglumine salt, betaine salt, caffeine salt, chloroprocaine salt, procaine salt, lidocaine salt, pyridine salt, picoline salt, piperidine salt, morpholine salt, piperazine salt, purine salt, theobromine salt, and choline salt), and the like.

The compound disclosed herein may exist in the form of a solvate (e.g., hydrate), and the compound disclosed herein contains a polar solvent as a structural element of the crystal lattice of the compound, particularly, for example, water, methanol or ethanol. The amount of polar solvent, especially water, can exist in a stoichiometric or non-stoichiometric ratio.

According to the molecular structure, the compounds disclosed herein may be chiral and may therefore exist in various enantiomeric forms. These compounds may therefore exist in racemic or optically active form. The compounds disclosed herein or intermediates thereof may be separated into enantiomers by chemical or physical methods well known to those skilled in the art, or used in this form for synthesis. In the case of racemic amines, diastereoisomers are manufactured from mixtures by reaction with optically active resolving agents. Examples of suitable resolving agents are optically active acids such as R- or S-tartaric acid, diacetyltartatic acid, dibenzoyitartaric acid, mandelic acid, malic acid, lactic acid, suitable N-protected amino acids (e.g., N-benzoylproline or N-benzenesulfonylproline) or various optically active camphorsulfonic acids. Enantiomeric resolution by chromatography can be advantageously performed with the aid of optically active resolving agents, such as dinitrobenzoyl phenyl glycine, cellulose triacetate or other carbohydrate derivatives or chirally derivatized methacrylate polymers immobilized on silica gel. Suitable eluents for this purpose are mixtures of solvent containing water or alcohol, for example, hexane/isopropanol/acetonitrile.

The corresponding stable isomers can be separated according to known methods, such as extraction, filtration or column chromatography.

The term "leaving group" refers to is an atom or a group of atoms that is replaced as stable species and takes the bound electrons as it leaves in a chemical reaction. Preferably, the leaving group is selected from: halogen (e.g. chlorine, bromine or iodine), hydroxy, $C_{1-40}$ haloalkyl, mesyloxy, p-toluenesulfonyloxy, trifluoromethanesulfonyloxy, nonafluorobutanesulfonyloxy, (4-bromobenzene)sulfonyloxy, (4-nitrobenzene)sulfonyloxy, (2-nitrobenzene)sulfonyloxy, (4-isopropylbenzene)sulfonyloxy, (2,4,6-triisopropylbenzene)sulfonyloxy, (2,4,6-trimethylbenzene)sulfonyloxy, (4-tert-butylbenzene)sulfonyloxy, benzenesulfonyloxy and (4-methoxybenzene)sulfonyloxy.

The term "patient" refers to any animal including mammals, preferably mice, rats, other rodents, rabbits, dogs, cats, pigs, cattle, sheep, horses or primates, and most preferably humans.

The term "therapeutically effective amount" refers to the amount of the active compound or drug that causes a biological or medical response that researchers, veterinarians, physicians, other clinicians, etc., are looking for in tissues, systems, animals, individuals or humans, including one or more of the following effects: (1) disease prevention: for example, the prevention of a disease, disorder or condition in an individual who is susceptible to the disease, disorder or condition but has not yet experienced or exhibited the pathology or symptoms of the disease; (2) disease inhibition: for example, the inhibition of a disease, disorder or condition in an individual who is experiencing or exhibiting the pathology or symptoms of the disease, disorder or condition (i.e., the prevention of the further development of the pathology and/or symptoms); and (3) disease alleviation: for example, the alleviation of a disease, disorder or condition in an individual who is experiencing or exhibiting the pathology or symptoms of the disease, disorder or condition (i.e., the reverse of the pathology and/or symptoms).

DETAILED DESCRIPTION

The technical scheme of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the content of the present disclosure described above are encompassed within the protection scope of the present disclosure.

Unless otherwise stated, the starting materials and reagents used in the following examples are all commercially available products or can be manufactured by using known methods.

Example 1

Synthesis of Compound N2

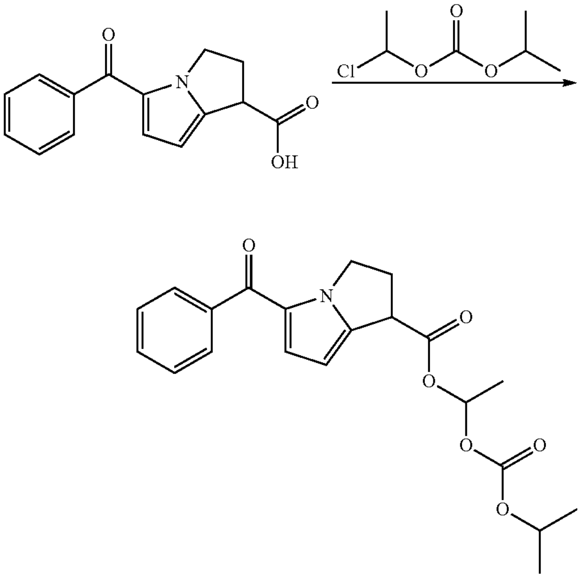

Ketorolac (4.401 g, 1724 mmol) was weighed into a dry two-necked reaction flask at room temperature, and 8.0 mL of DMSO was added and stirred to dissolve ketorolac. Potassium fluoride KF (2.205 g, 38.00 mmol) was weighed and added to the reaction flask described above, the reaction flask was purged with Ar for 2 times, and 1-chloroethyl isopropyl carbonate (6.9 g, 18.88 mmol) was weighed and added dropwise to the reaction flask described above. After the dropwise addition was completed, the reaction flask was placed at 35° C. and reacted for 1 h. TBAB (1.385 g, 4.30 mmol) and potassium iodide KI (1.430 g, 8.61 mmol) were then added to the reaction flask, followed by overnight stirring. 20 mL of water and 30 mL of ethyl acetate were added to the reaction flask, followed by liquid separation, the EA layer was washed with 5% $NaHCO_3$ aqueous solution, washed with water and saturated. NaCl aqueous solution, dried over anhydrous $Na_2SO_4$, and concentrated, and the residue was subjected to column chromatography (wet loading, PE/EA=6:1) to give a colorless oil (4,507 g, yield: 82.27%);

$^1H$ NMR (400 MHz, $CDCl_3$) δ 7.8188-7.7980 (m, 2H), 7.5470-7.5104 (m, 1H), 7.4672-7.4302 (t, 2H, J=7.1 Hz), 6.8288-6.7883 (m, 2H), 6.1141-6.1042 (d, 1H, J=4.0 Hz), 4.9543-4.8513 (m, 1H), 4.6028-4.5372 (m, 1H), 4.4778-4.4116 (m, 1H), 4.1087-4.0720 (m, 1H), 2.9997-2.9157 (m, 1H), 2.8462-2.7553 (m, 1H), 1.5566-1.4431 (m, 3H), 1.3291-1.3094 (m, 6H);

ESI-MS m/z=386.1, $[M+H]^+$.

Example 2

Synthesis of Compound N2(S)

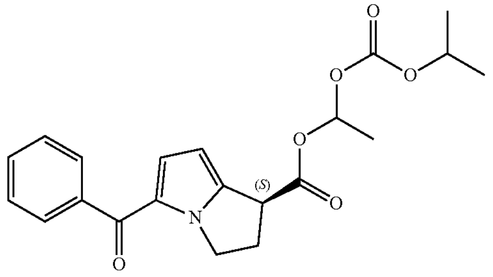

The synthesis method of compound N1(S) is the same as that of compound a, except that ketorolac was replaced with S-ketorolac;

$^1$H NMR (400 MHz, $CDCl_3$) δ 7.8188-7.7980 (m, 2H), 7.5470-7.5104 (m, 1H), 7.4672-7.4302 (t, 2H, J=7.1 Hz), 6.8288-6.7883 (m, 2H), 6.1141-6.1042 (d, 1H, J=4.0 Hz), 4.9543-4.8513 (m, 1H), 4.6028-4.5372 (m, 1H), 4.4778-4.4116 (m, 1H), 4.1087-4.0720 (m, 1H), 2.9997-2.9157 (m, 1H), 2.8462-2.7553 (m, 1H), 1.5566-1.4431 (m, 3H), 1.3291-1.3094 (m, 6H);

ESI-MS m/z=386.1, $[M+H]^+$.

Example 3

Synthesis of Compound N3

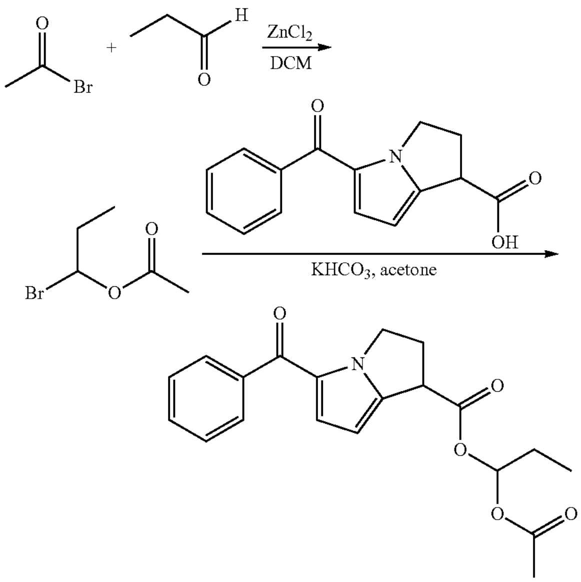

Synthesis of 1-bromopropyl acetate: $ZnCl_2$ (0.020 g, 0.15 mmol) was weighed and added to a dry two-necked reaction flask, the reaction flask was purged with N2 for 2 times, then 40 mL of anhydrous dichloromethane and acetyl bromide (4.0 g, 32.53 mmol) were added to the reaction flask, and the reaction was placed in an ice-water bath at 0° C. under constant stirring. n-propionaldehyde (2.064 g, 35.54 mmol) was added slowly and dropwise to the reaction flask described above, and after the dropwise addition was completed, the reaction flask was placed at room temperature and reacted for 1 h. 10 mL of water was added to the reaction flask, followed by liquid separation, the dichloromethane layer was washed with 5% $NaHCO_3$ aqueous solution for 2 times until pH was about 9, washed with water again and with saturated brine, dried over anhydrous sodium sulfate, and concentrated under reduced pressure to give a light yellow oil (4.4 g, crude), namely 1-bromopropyl acetate, which was used directly in the next reaction step without further purification;

Synthesis of compound N3: ketorolac (1.0 g, 3.92 mmol) and $KHCO_3$ (0.628 g, 6.27 mmol) were weighed and added to a dry single-necked reaction flask, 8 mL of acetone was added at room temperature under constant stirring, 1.4 g of fresh-synthesized 1-bromopropyl acetate crude product was added slowly and dropwise to the reaction flask described above, and after the dropwise addition was completed, the reaction was kept at room temperature under constant stirring for 1-5 h; after the reaction was completed, 10 mL of water and 40 mL of ethyl acetate were added to the reaction flask, followed by liquid separation, and the organic layer was washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=7:1) to give compound N3 (1.14 g, yield: 82%);

$^1$H NMR (400 MHz, $CDCl_3$) δ 7.8210-7.7970 (m, 2H), 7.5465-7.5033 (m, 1H), 7.4644-7.4274 (m, 2H), 6.8211-6.8084 (dd, 1H, J=1.2, 3.9 Hz), 6.7967-6.7695 (t, J=5.4 Hz, 1H), 6.1057-6.0858 (m, 1H), 4.6092-4.5359 (m, 1H), 4.4870-4.4032 (m, 1H), 4.1267-4.0606 (m, 1H), 2.9964-2.7485 (m, 2H), 2.0928-2.0688 (d, 3H, J=9.6 Hz), 1.8697-1.7952 (m, 2H), 0.9855-0.9329 (m, 3H);

ESI-MS m/z=356.1, $[M+H]^+$.

Example 4

Synthesis of Compound N4

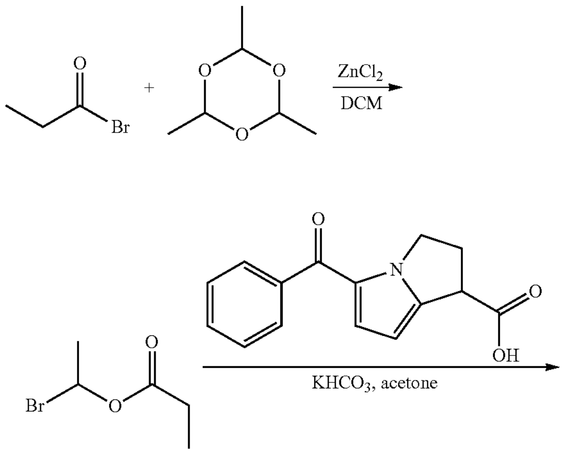

-continued

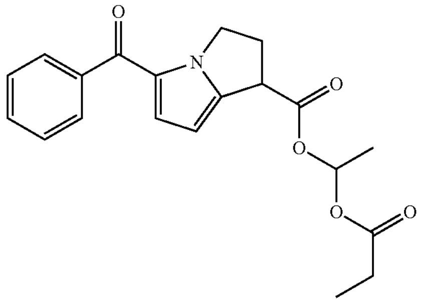

Synthesis of 1-bromoethyl propionate: 5.0 mg of $ZnCl_2$ (0.005 g, 0.04 mmol) was weighed and added to a dry two-necked reaction flask, the reaction flask was purged with $N_2$ for 2 times, then 40 mL of anhydrous dichloromethane and propionyl bromide (2.0 g, 14.60 mmol) were added to the reaction flask, and the reaction was placed in an ice-water bath at 0° C. under constant stirring. 0.67 mL of paraldehyde (0.66 g, 4.99 mmol) was added slowly and dropwise to the reaction flask described above, and after the dropwise addition was completed, the reaction flask was placed at room temperature and reacted for 1 h, 10 mL of water was added to the reaction flask, followed by liquid separation, the dichloromethane layer was washed with 5% $NaHCO_3$ aqueous solution for 2 times until pH was about 9, washed with water again and with saturated brine, dried over anhydrous sodium sulfate, and concentrated under reduced pressure to give a light yellow oil (1.5 g, crude), namely 1-bromoethyl propionate, which was used directly in the next reaction step without further purification;

Synthesis of compound N4: ketorolac (0.5 g, 1.96 mmol) and $KHCO_3$ (0.314 g, 3.14 mmol) were weighed and added to a dry single-necked reaction flask, 8 mL of acetone was added at room temperature under constant stirring, 0.7 g of fresh-synthesized 1-bromoethyl propionate crude product was added slowly and dropwise to the reaction flask described above, and after the dropwise addition was completed, the reaction was kept at room temperature under constant stirring for 1-5 h; after the reaction was completed, 10 mL of water and 40 ml of ethyl acetate were added to the reaction flask, followed by liquid separation, and the organic layer was washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=7:1) to give compound. N4 (0.52 g, yield: 75%);

$^1H$ NMR (400 MHz, $CDCl_3$) δ 7.8211-7.8028 (d, 2H, J=7.3 Hz), 7.5452-7.5090 (t, 1H, J=7.3 Hz), 7.4665-7.4293 (t, 2H, J=7.6 Hz), 6.9381-6.8975 (q, 1H, J=5.4 Hz), 6.8195-6.8098 (d, 1H, J=4.0 Hz), 6.1031-6.0842 (t, 1H, J=3.8 Hz), 4.6117-4.5388 (m, 1H), 4.4745-4.3959 (m, 1H), 4.0846-4.0500 (t, 1H, J=7.7 Hz), 2.9828-2.8764 (m, 1H), 2.8428-2.7521 (m, 1H), 2.3893-2.3105 (m, 2H), 1.5241-1.5037 (m, 3H), 1.1681-1.1076 (q, 3H, J=7.6 Hz);

ESI-MS m/z=356.1, $[M+H]^+$.

Example 5

Synthesis of Compound N5

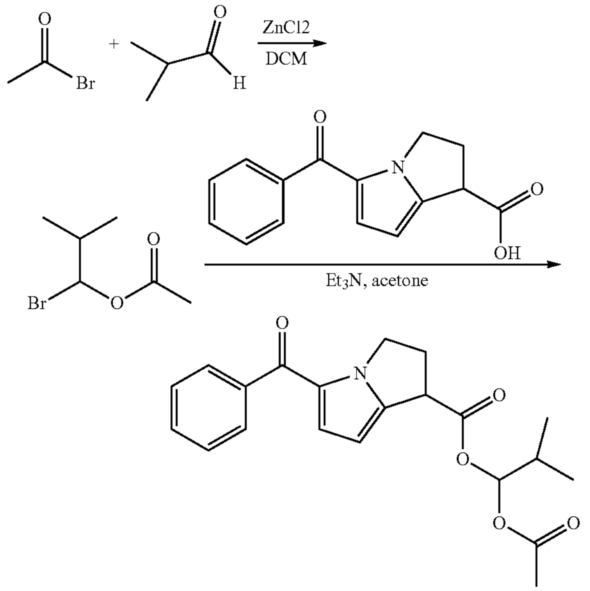

Synthesis of 1-bromoisobutyl acetate: 20.0 mg of $ZnCl_2$ (0.02 g, 0.15 mmol) was weighed and added to a dry two-necked reaction flask, the reaction flask was purged with $N_2$ for 2 times, then 40 mL of anhydrous dichloromethane and acetyl bromide (4.0 g, 29.20 mmol) were added to the reaction flask, and the reaction was placed in an ice-water bath at 0° C. under constant stirring. Isobutyraldehyde (2.59 g, 35.92 mmol) was added slowly and dropwise to the reaction flask described above, and after the dropwise addition was completed, the reaction flask was placed at room temperature and reacted for 1 h, 10 mL of water was added to the reaction flask, followed by liquid separation, the dichloromethane layer was washed with 5% $NaHCO_3$ aqueous solution for 2 times until pH was about 9, washed with water again and with saturated brine, dried over anhydrous sodium sulfate, and concentrated under reduced pressure to give a light yellow oil (4.4 g, crude), namely 1-bromoisobutyl acetate, which was used directly in the next reaction step without further purification;

Synthesis of compound N5: ketorolac (2.0 g, 7.83 mmol) and 2.5 mL of triethylamine (1.82 g, 17.99 mmol) were weighed and added to a dry single-necked reaction flask. 8 mL of acetone was added at room temperature under constant stirring, 3.48 g of fresh-synthesized 1-bromoisobutyl acetate crude product was added slowly and dropwise to the reaction flask described above, and after the dropwise addition was completed, the reaction was kept at room temperature under constant stirring for 1-5 h; after the reaction was completed, 10 mL of water and 40 mL of ethyl acetate were added to the reaction flask, followed by liquid separation, and the organic layer was washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=8:1) to give compound N5 (2.29 g, yield: 79.5%);

$^1H$ NMR (400 MHz, $CDCl_3$) δ 7.8238-7.8058 (d, 2H, J=7.2 Hz), 7.5490-7.5126 (m, 1H), 7.4686-7.4315 (t, 2H, J=7.0 Hz), 6.8247-6.8153 (d, 1H, J=3.8 Hz), 6.6818-6.6696 (d, 1H, J=4.9 Hz), 6.1166-6.0877 (m, 1H), 4.6042-4.5389 (m, 1H), 4.4873-4.4215 (m, 4.1469-4.0717 (m, 1H), 3.0078-2.7502 (m, 2H), 2.1007-2.0262 (m, 4H), 0.9918-0.9470 (m, 6H);

ESI-MS m/z=370.1, $[M+H]^+$.

Example 6

Synthesis of Compound N6

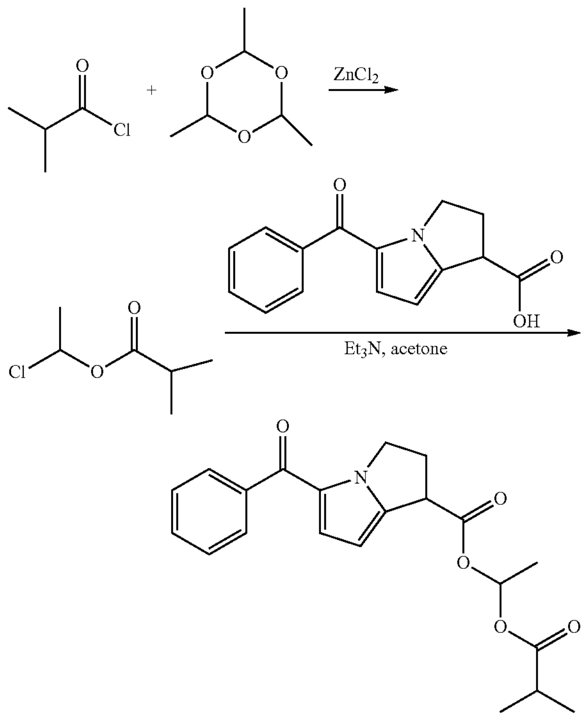

Synthesis of 1-chloroethyl isobutyrate: $ZnCl_2$ (0.01 g, 0.07 mmol) was weighed and added to a dry two-necked reaction flask, the reaction flask was purged with $N_2$ for 2 times, then isobutyryl chloride (4.0 g, 37.54 mmol) was added to the reaction flask, the reaction was placed in an ice-water bath at 0° C. under constant stirring, isobutyraldehyde (2.59 g, 35.92 mmol) was added slowly and dropwise to the reaction flask described above, and after the dropwise addition was completed, the reaction flask was placed at 80° C. and reacted for 1 h. The reaction solution was cooled to room temperature, 10 mL of water and 10 mL of dichloromethane were added to the reaction flask, followed by liquid separation, the dichloromethane layer was washed with 5% $NaHCO_3$ aqueous solution for 2 times until pH was about 9, washed with water and saturated brine, dried over anhydrous sodium sulfate, and concentrated under reduced pressure to give a light yellow oil (2.4 g, crude), namely 1-chloroethyl isobutyrate, which was used directly in the next reaction step without further purification;

Synthesis of compound N6: ketorolac (1.9 g, 7.44 mmol) and triethylamine (1.46 g, 14.43 mmol) were weighed and added to a dry single-necked reaction flask, 8 mL of acetone was added at room temperature under constant stirring, 2.4 g of fresh-synthesized 1-bromoisobutyl acetate crude product was added slowly and dropwise to the reaction flask described above, and after the dropwise addition was completed, the reaction was kept at room temperature under constant stirring for 1-5 h; after the reaction was completed, 10 mL of water and 40 mL of ethyl acetate were added to the reaction flask, followed by liquid separation, and the organic layer was washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=8:1) to give compound N6 (1.4 g, yield: 51%);

$^1H$ NMR (400 MHz, $CDCl_3$) δ 7.7493-7.7306 (d, 2H, J=7.5 Hz), 7.4749-7.4383 (t, 1H, J=7.4 Hz), 7.3958-7.3585 (t, 2H, J=7.6 Hz), 6.8573-6.8071 (m, 1H), 6.7468-6.7371 (d, 1H, J=3.9 Hz), 6.0294-6.0092 (t, 1H, J=4.0 Hz), 4.5355-4.4694 (m, 1H), 4.4069-4.3270 (m, 1H), 4.0109-3.9742 (t, 1H, J=7.5 Hz), 2.8969-2.8076 (m, 1H), 2.7704-2.6811 (m, 1H), 2.5181-2.4301 (m, 1H), 1.4535-1.4342 (m, 3H), 1.1105-1.0656 (m, 6H);

ESI-MS m/z=370.1, $[M+H]^+$.

Example 7

Synthesis of Compound N7

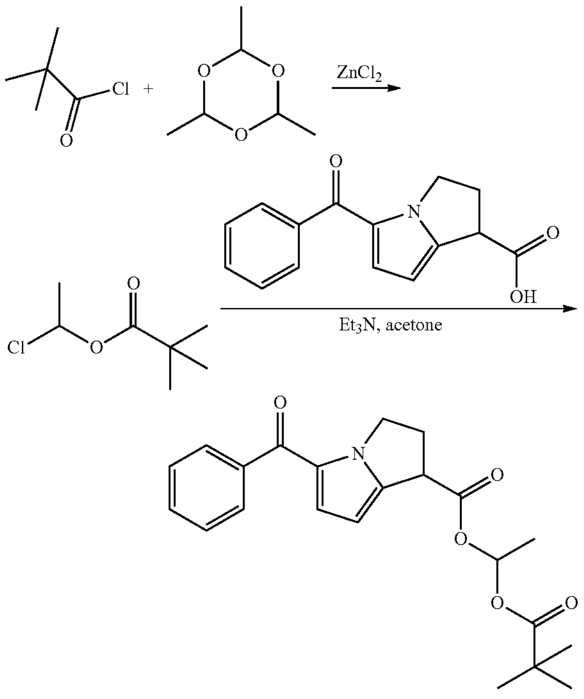

Synthesis of 1-chloroethyl pivalate: $ZnCl_2$ (4.0 g, 0.03 mmol) was weighed and added to a dry two-necked reaction flask, the reaction flask was purged with $N_2$ for 2 times, then pivaloyl chloride (2.0 g, 16.59 mmol) was added to the reaction flask, and the reaction was placed in an ice-water bath at 0° C. under constant stirring. Paraldehyde (0.75 g, 5.67 mmol) was added slowly and dropwise to the reaction flask described above, and after the dropwise addition was completed, the reaction flask was placed at 80° C. and reacted for 1 h. The reaction solution was cooled to room temperature. 10 mL of water and 10 mL of dichloromethane were added to the reaction flask, followed by liquid separation, the dichloromethane layer was washed with 5% $NaHCO_3$ aqueous solution for 2 times until pH was about 9, washed with water and saturated brine, dried over anhydrous sodium sulfate, and concentrated under reduced pressure to give a light yellow oil (2.19 g, crude), namely 1-chloroethyl pivalate, which was used directly in the next reaction step without further purification;

Synthesis of compound N7: ketorolac (1.0 g, 3.92 mmol) and triethylamine (0.63 g, 6.26 mmol) were weighed and added to a dry single-necked reaction flask, 8 mL of acetone was added at room temperature under constant stirring, 1.7 g of fresh-synthesized 1-chloroethyl pivalate crude product was added slowly and dropwise to the reaction flask described above, and after the dropwise addition was completed, the reaction was performed at 40° C. for 1-5 h; after the reaction was completed, 10 mL of water and 40 mL of ethyl acetate were added to the reaction flask, followed by liquid separation, and the organic layer was then washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=8:1) to give compound N7 (0.482 g, yield: 32%);

$^1H$ NMR (400 MHz, $CDCl_3$) δ 7.8221-7.8024 (d, 2H, J=7.9 Hz), 7.5482-7.5128 (t, 1H, J=7.6 Hz), 7.4684-7.4312 (m, 2H), 6.9173-6.8578 (m, 1H), 6.8194-6.8104 (m, 1H), 6.0970-6.0804 (m, 1H), 4.5839-4.4044 (m, 2H), 4.0830-4.0468 (m, 1H), 2.9648-2.7499 (m, 2H), 1.5237-1.5030 (m, 3H), 1.2032-1.1734 (m, 9H);

EST-MS m/z=384.1, $[M+H]^+$.

Example 8

Synthesis of Compound N8

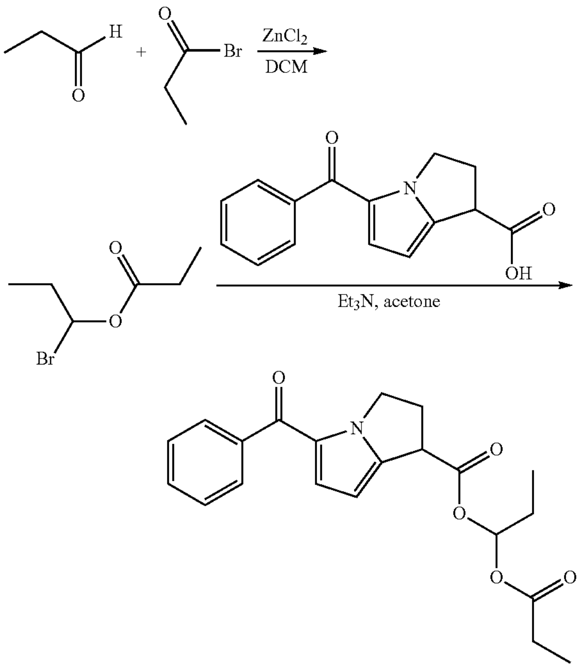

Synthesis of 1-bromopropyl propionate: $ZnCl_2$ (0.01 g, 0.07 mmol) was weighed and added to a dry two-necked reaction flask, the reaction flask was purged with $N_2$ for 2 times, then 15 mL of anhydrous dichloromethane and propionyl bromide (3.0 g, 21.90 mmol) were added to the reaction flask, and the reaction was placed in an ice-water bath at 0° C. under constant stirring. Propionaldehyde (1.39 g, 23.93 mmol) was added slowly and dropwise to the reaction flask described above, and after the dropwise addition was completed, the reaction flask was placed at room temperature for 1 h. 10 mL of water was added to the reaction flask, followed by liquid separation, the dichloromethane layer was washed with 5% $NaHCO_3$ aqueous solution for 2 times until pH was about 9, washed with water again and with saturated brine, dried over anhydrous sodium sulfate, and concentrated under reduced pressure to give a black brown oil (2.1 g, crude), namely 1-bromopropyl propionate, which was used directly in the next reaction step without further purification;

Synthesis of compound N8: ketorolac (1.0 g, 3.92 mmol) and triethylamine (0.99 g, 9.78 mmol) were weighed and added to a dry single-necked reaction flask, 8 mL of acetone was added at room temperature under constant stirring, 1.7 g of fresh-synthesized 1-bromopropyl propionate crude product was added slowly and dropwise to the reaction flask described above, and after the dropwise addition was completed, the reaction was kept at room temperature under constant stirring for 1-5 h; after the reaction was completed, 10 mL of water and 40 mL of ethyl acetate were added to the reaction flask, followed by liquid separation, and the organic layer was washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=8:1) to give compound N8 (1:1 g, yield: 76%);

$^1H$ NMR (400 MHz, $CDCl_3$) δ 7.8188-7.8001 (d, 2H, J=7.5 Hz), 7.5478-7.5047 (m, 1H), 7.4654-7.4284 (m, 2H), 6.8169-6.7859 (m, 2H), 6.1063-6.0798 (m, 1H), 4.6069-4.5336 (m, 1H), 4.4789-4.4010 (m, 1H), 4.1082-40599 (m, 1H), 2.9930-2.7472 (m, 211), 2.3965-2.3141 (m, 2H), 1.8693-1.7968 (m, 2H), 1.1687-1.1040 (m, 3H), 0.9832-0.9367 (m, 3H);

EST-MS m/z=370.2, $[M+H]^+$.

Example 9

Synthesis of Compound N8(S)

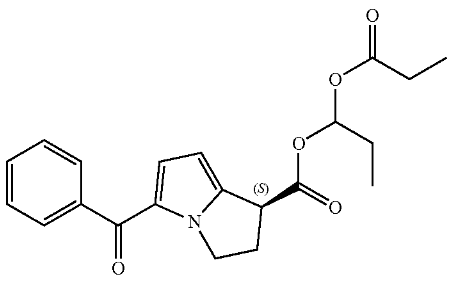

The procedure was the same as in Example 8, except that ketorolac was replaced with S-ketorolac;

$^1H$ NMR (400 MHz, $CDCl_3$) δ 7.8215-7.8035 (d, 2H, J=7.2 Hz), 7.5503-7.5070 (m, 1H), 7.4678-7.4308 (m, 2H), 6.7476-6.7165 (m, 2H), 6.1055-6.0815 (m, 1H), 4.5958-4.4552 (m, 1H), 4.4506-4.4043 (m, 1H), 4.1476-4.0670 (m, 1H), 2.9951-2.7501 (m, 2H), 2.3978-2.3156 (m, 2H), 1.8719-1.7990 (m, 2H), 1.1718-1.1073 (m, 3H), 0.9859-0.9350 (m, 3H);

EST-MS m/z=370.2, $[M+H]^+$.

Example 10

Synthesis of Compound N9

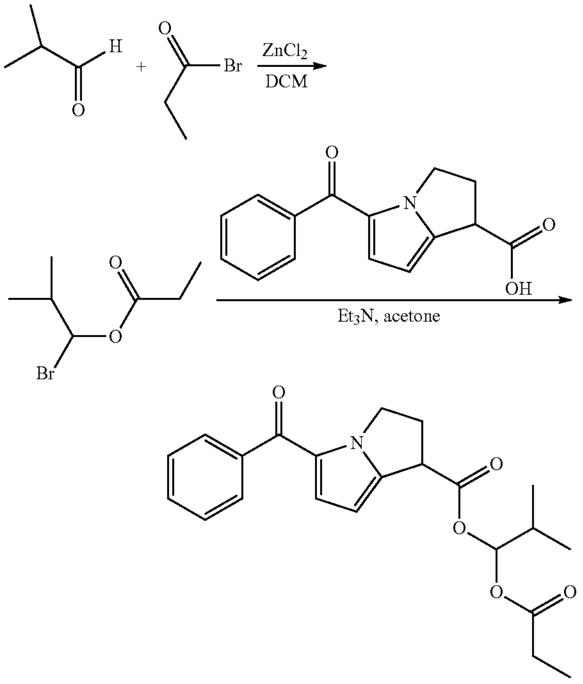

Synthesis of 1-bromoisobutyl propionate: $ZnCl_2$ (0.006 g, 0.004 mmol) was weighed and added to a dry two-necked reaction flask, the reaction flask was purged with $N_2$ for 2 times, then 20 mL of anhydrous dichloromethane and propionyl bromide (3.0 g, 21.90 mmol) were added to the reaction flask, and the reaction was placed in an ice-water bath at 0° C. under constant stirring. Isobutyraldehyde (1.74 g, 24.13 mmol) was added slowly and dropwise to the reaction flask described above, and after the dropwise addition was completed, the reaction flask was placed at room temperature and reacted for 1 h. 10 mL of water was added to the reaction flask, followed by liquid separation, the dichloromethane layer was washed with 5% $NaHCO_3$ aqueous solution for 2 times until pH was about 9, washed with water again and with saturated brine, dried over anhydrous sodium sulfate, and concentrated under reduced pressure to give a light yellow oil (3.0 g, crude), namely 1-bromoisobutyl propionate, which was used directly in the next reaction step without further purification;

Synthesis of compound N9: ketorolac (1.5 g, 5.88 mmol) and triethylamine (1.49 g, 14.72 mmol) were weighed and added to a dry single-necked reaction flask, 8 mL of acetone was added at room temperature under constant stirring, 2.68 g of fresh-synthesized 1-bromoisobutyl propionate crude product was added slowly and dropwise to the reaction flask described above, and after the dropwise addition was completed, the reaction was heated to 40° C. and performed for 1-5 h; after the reaction was completed, 10 mL of water and 40 mL of ethyl acetate were added to the reaction flask, followed by liquid separation, and the organic layer was then washed with 5% $NaHCO_3$ aqueous solution, washed with water and saturated brine, dried over anhydrous sodium sulfate, and concentrated under reduced pressure to give a light yellow oil, which was subjected to flash column chromatography (wet loading, PE/EA=6:1) to give compound N9 (1.64 g, yield: 73%);

$^1H$ NMR (400 MHz, $CDCl_3$) δ 7.8173-7.7966 (m, 2H), 7.5441-7.5075 (t, 1H, J=7.4 Hz), 7.4648-7.4275 (t, 2H, J=7.6 Hz), 6.8175-6.8076 (d, 1H, J=4.0 Hz), 6.6932-6.6808 (d, 1H, J=5.0 Hz), 6.1109-6.0776 (dd, 1H, J=4.0, 9.4 Hz), 4.5953-4.5291 (m, 1H), 4.4845-4.4116 (m, 1H), 4.1257-4.0639 (m, 1H), 3.0003-2.7456 (m, 2H), 2.3990-2.3134 (m, 2H), 2.0989-2.0082 (m, 1H), 1.1695-1.1016 (m, 3H), 0.9854-0.9436 (m, 6H);

ESI-MS m/z=384.1, $[M+H]^+$.

Example 11

Synthesis of Compound N10

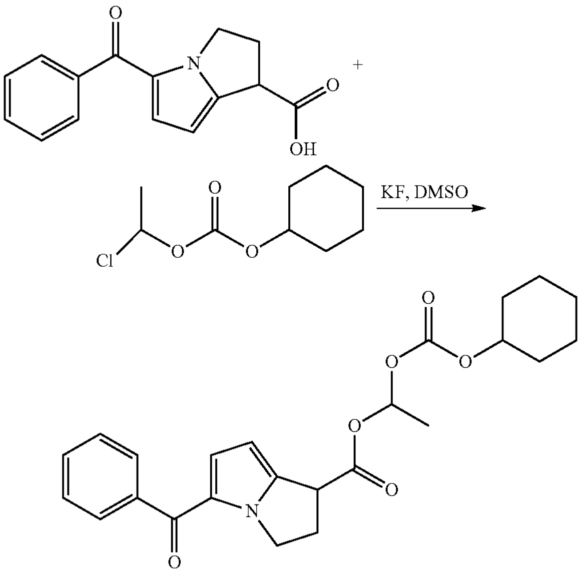

Ketorolac (1.0 g, 3.92 mmol) was weighed into a dry two-necked reaction flask at room temperature, and 3.0 mL of DMSO was added and stirred to dissolve ketorolac. KF (0.5 g, 8.61 mmol) was weighed and added to the reaction flask described above, the reaction flask was purged with Ar for 2 times, 1-chloroethyl cyclohexanyl carbonate (0.83 g, 4.02 mmol) was weighed and added dropwise to the reaction flask described above, and after the dropwise addition was completed, the reaction flask was placed at 35° C. and reacted overnight. 20 mL of water and 30 mL of ethyl acetate were added to the reaction flask, followed by liquid separation, the EA layer was washed with 5% $NaHCO_3$ aqueous solution, washed with water and saturated NaCl aqueous solution, dried over anhydrous $Na_2SO_4$, and concentrated, and the residue was subjected to column chromatography (wet loading, PE/EA=6:1) to give a light yellow oil (0.99 g, yield: 67%);

$^1H$ NMR (400 MHz, $CDCl_3$) δ 7.8183-7.7989 (d, 2H, J=7.8 Hz), 7.5461-7.5096 (t, 1H, J=7.3 Hz), 7.4662-7.4288

(t, 2H, J=7.6 Hz), 6.8315-6.7939 (m, 2H), 6.6932-6.6808 (d, 1H, J=5.0 Hz), 6.1129-6.0969 (m, 1H), 4.6776-4.5399 (m, 2H), 4.4781-4.4017 (m, 1H), 4.1064-4.0606 (m, 1H), 2.9980-2.8994 (m, 1H), 2.8512-2.7524 (m, 1H), 1.9165 (s, 2H), 1.7489-1.7393 (m, 1H), 1.5653-1.3194 (m, 9H);

ESI-MS m/z=426.1, $[M+H]^+$.

Example 12

Synthesis of Compound N12

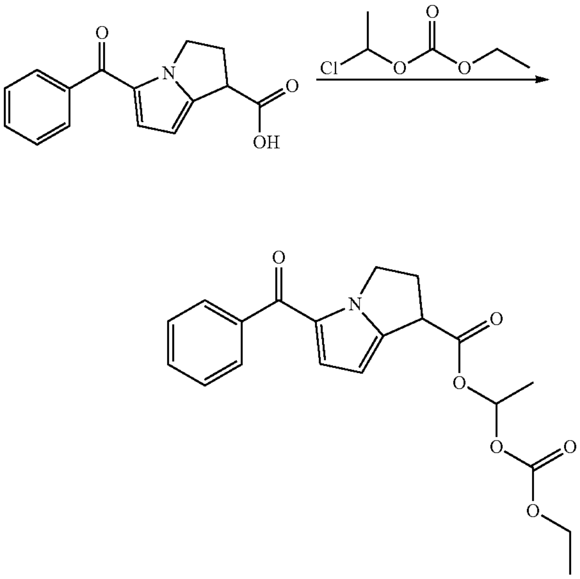

Ketorolac (2.0 g, 7.83 mmol) and DBU (2.38 g, 15.63 mmol) were added to a 50 mL dry single-necked reaction flask at room temperature, 10 mL of acetone was added and stirred to dissolve ketorolac, then 1-chloroethyl ethyl carbonate (1.79 g, 11.73 mmol) was weighed and added to the reaction flask described above, and the reaction was heated to 40° C. and performed for 2 h. KI (1.3 g, 7.83 mmol) and TBAB (0.51 g, 1.58 mmol) were weighed and added to the reaction flask, and the reaction was continued under stirring at 40° C. overnight. Water (10 mL) and ethyl acetate (30 mL) were added to the reaction flask, followed by liquid separation, the organic layer was washed with 5% $NaHCO_3$ aqueous solution, washed with water and saturated brine, dried over anhydrous sodium sulfate, and concentrated under reduced pressure, and the residue was subjected to flash column chromatography (PE/EA=8:1) to give the target product (1.90 g, yield: 65.3%);

$^1H$ NMR (400 MHz, $CDCl_3$) δ 7.83-7.79 (m, 2H), 7.55-7.51 (m, 1H), 7.47-7.43 (m, 2H), 6.87-6.79 (m, 2H), 6.11 (d, J=4.0 Hz, 1H), 4.62-4.53 (m, 1H), 4.48-4.40 (m, 1H), 4.29-4.17 (m, 2H), 4.14-4.06 (m, 1H), 3.01-2.89 (m, 1H), 2.86-2.75 (m, 1H), 1.56 (dd, J=2.8, 5.6 Hz, 3H), 1.35-1.28 (m, 3H).

ESI-MS m/z=372.1, $[M+H]^+$.

Example 13

Synthesis of Compound N12(S)

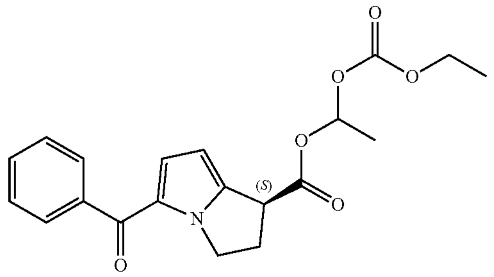

The procedure was the same as in Example 12, except that ketorolac was replaced with S-ketorolac;

$^1H$ NMR (400 MHz, $CDCl_3$) δ 7.83-7.79 (m, 2H), 7.55-7.51 (m, 1H), 7.47-7.43 (m, 2H), 6.87-6.79 (m, 2H), 6.11 (d, J=4.0 Hz, 1H), 4.62-4.53 (m, 1H), 4.48-4.40 (m, 1H), 4.29-4.17 (m, 2H), 4.14-4.06 (m, 1H), 3.01-2.89 (m, 1H), 2.86-2.75 (m, 1H), 1.56 (dd, J=2.8, 5.6 Hz, 3H), 1.35-1.28 (m, 3H).

ESI-MS m/z=372.1, $[M+H]^+$.

Example 14

Synthesis of Compound N13

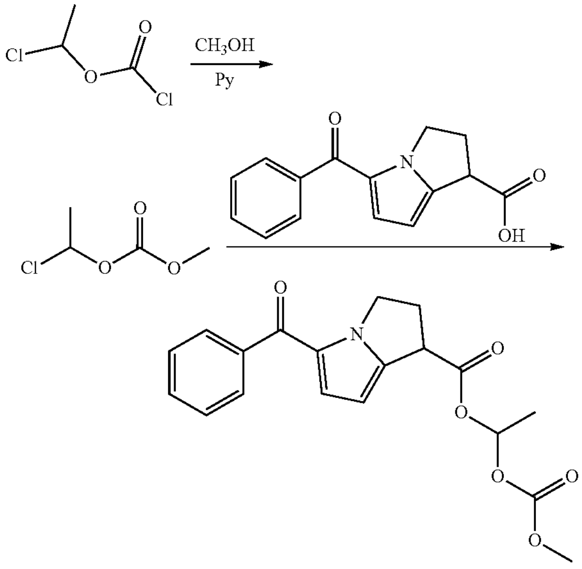

Synthesis of 1-chloroethyl methyl carbonate: 1-chloroethyl chloroformate (2.0 g) was weighed in a 50 mL dry two-necked reaction flask under $N_2$ atmosphere, anhydrous dichloromethane was added, the reaction flask was placed in an ice bath under stirring, methanol (0.67 g, 1.5 eq) was weighed in the reaction flask, then pyridine Py (1.33 g, 1.2 eq) was weighed and added slowly and dropwise to the reaction flask, and after the dropwise addition was completed, the reaction flask was placed at room temperature and reacted for 1 h. A small amount of dichloromethane and water were supplemented to the reaction flask, followed by liquid separation, and the dichloromethane layer was washed with 5% $KHSO_4$ until pH was about 3, and then washed with water until it was neutral, and the dichloromethane was dried over anhydrous sodium sulfate and concentrated under reduced pressure to give 1-chloroethyl methyl carbonate (0.665 g).

Synthesis of compound N13: ketorolac (0.73 g, 1.0 eq) was weighed in a dry single-necked reaction flask, 10 mL of acetone was added and stirred to dissolve ketorolac, DBU (0.88 g, 2.0 eq) and the fresh-prepared 1-chloroethyl methyl carbonate (0.66 g, 1.5 eq) were added, the reaction was performed at 40° C. for 1 h, KI (1.0 eq) and TBAB (0.2 eq) were supplemented, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.61 g, yield: 61%).

$^1H$ NMR (400 MHz, $CDCl_3$) δ 7.84-7.80 (m, 2H), 7.59-7.53 (m, 1H), 7.50-7.46 (m, 2H), 6.91-6.82 (m, 2H), 6.13 (d, J=4.2 Hz, 1H), 4.62-4.53 (m, 1H), 4.48-4.40 (m, 1H), 4.29-4.17 (d, J=7.1 Hz, 3H), 4.14-4.06 (m, 1H), 3.01-2.89 (m, 1H), 2.86-2.75 (m, 1H), 1.57 (dd, J=2.8, 5.6 Hz, 3H).

EST-MS m/z=358.2, $[M+H]^+$.

Example 15

Synthesis of Compound N14

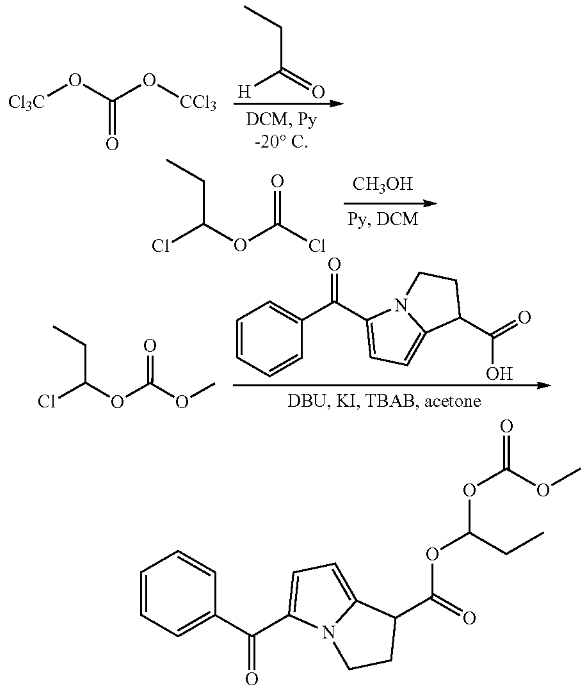

Synthesis of 1-chloropropyl chloroformate: triphosgene (10.00 g, 33.70 mmol) was weighed to a 100 mL three-necked reaction flask. 15 mL of anhydrous dichloromethane was added, the reaction flask was purged with Ar gas for 3 times, and the reaction flask was placed to a cold trap at −20° C. under constant stirring. Py (0.54 g, 6.83 mmol) was weighed and added with 5 mL of dichloromethane for dilution, and added to the reaction flask. Then n-propionaldehyde (4.6 g, 79.20 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (3.91 g, yield: 73.2%).

Synthesis of 1-chloropropyl methyl carbonate: 1-chloropropyl chloroformate (1.00 g, 6.38 mmol) was weighed in a dry two-necked reaction flask, 10 mL of anhydrous dichloromethane was added under constant stirring, methanol (0.30 g, 9.50 mmol) was weighed and added to the reaction flask described above, the reaction flask was placed in an ice-water bath under constant stirring, Py (0.63 g, 7.96 mmol) was weighed and added slowly and dropwise to the reaction flask described above, a white solid produced during the dropwise addition process, and after the dropwise addition was completed, the reaction flask was placed at room temperature and reacted for 1 h, 10 mL of water was added to the reaction flask, followed by liquid separation, and the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (0.705 g), which was used directly in the next reaction step without further purification;

Synthesis of compound N14: ketorolac (0.73 g, 2.86 mmol) was weighed to a dry single-necked reaction flask, 10 mL of acetone was added and stirred to dissolve ketorolac, DBU (0.88 g, 5.78 mmol) and 0.66 g of fresh-prepared 1-chloropropyl methyl carbonate were added, the reaction was performed at 40° C. for 1 h, KI (0.48 g, 2.90 mmol) and TBAB (0.19 g, 0.58 mmol) were supplemented, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.64 g, yield: 58.1%).

$^1H$ NMR (400 MHz, $CDCl_3$) δ 7.83-7.80 (m, 2H), 7.49-7.44 (m, 2H), 6.87-6.79 (m, 2H), 6.82 (d, J=3.9 Hz, 1H), 6.12-6.10 (m, 1H), 4.67-4.42 (m, 2H), 4.23 (d, J=6.5 Hz, 3H), 4.14-4.02 (m, 1H), 3.04-2.76 (m, 2H), 1.96-1.82 (m, 2H), 1.04-0.96 (m, 3H).

ESI-MS m/z=372.1, $[M+H]^+$.

Example 16

Synthesis of Compound N15

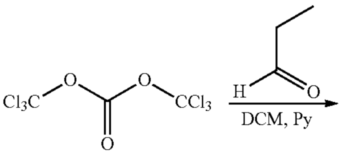

-continued

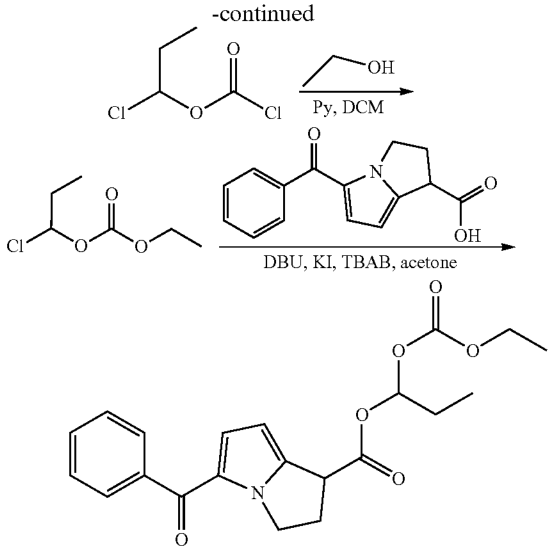

Synthesis of 1-chloropropyl chloroformate: triphosgene (10.00 g, 33.70 mmol) was weighed to a 100 mL three-necked reaction flask. 15 mL of anhydrous dichloromethane was added, the reaction flask was purged with Ar gas for 3 times, and the reaction flask was placed to a cold trap at −20° C. under constant stirring. Py (0.54 g, 6.83 mmol) was weighed and added with 5 mL of dichloromethane for dilution, and added to the reaction flask. Then n-propionaldehyde (4.6 g, 79.20 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (3.91 g, yield: 73.2%).

Synthesis of 1-chloropropyl ethyl carbonate: 1-chloropropyl chloroformate (1.0 g, 6.38 mmol) was weighed to a thy two-necked reaction flask, 10 mL of anhydrous dichloromethane was added under constant stirring, ethanol (0.44 g. 9.55 mmol) was weighed and added to the reaction flask described above, the reaction flask was placed in an ice-water bath under constant stirring, pyridine (0.63 g, 7.96 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (0.766 g), which was used directly in the next reaction step without further purification; Synthesis of compound NIS: ketorolac (0.73 g, 2.86 mmol) was weighed to a dry single-necked reaction flask, 10 mL of acetone was added and stirred to dissolve ketorolac, DEW (0.88 g, 5.78 mmol) and 0.78 g of the fresh-prepared 1-chloropropyl ethyl carbonate were added, the reaction was performed at 40° C., for 1 h, KI (0.48 g, 2.90 mmol) and TBAB (0.19 g, 0.58 mmol) were added, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.66 g, yield: 59.88%).

$^1H$ NMR (400 MHz, $CDCl_3$) δ 7.8174-7.7961 (m, 2H), 7.4658-7.4288 (m, 2H), 6.87-6.79 (m, 2H), 6.81 (d, J=3.9 Hz, 1H), 6.1138-6.0967 (m, 1H), 4.6115-4.4063 (m, 2H), 4.2648-4.1697 (m, 2H), 4.1276-4.0759 (m, 1H), 3.0117-2.7529 (m, 2H), 1.9097-1.8045 (m, 2H), 1.3463-1.2380 (m, 3H), 1.0103-0.9594 (m, 3H).

ESI-MS m/z=385.2, $[M+H]^+$.

Example 17

Synthesis of Compound N15(S)

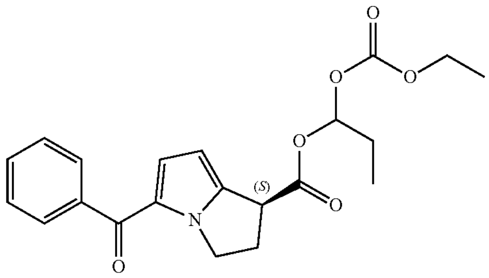

The procedure was the same as in Example 16, except that ketorolac was replaced with S-ketorolac;

$^1H$ NMR (400 MHz, $CDCl_3$) δ 7.8174-7.7961 (m, 2H), 7.4658-7.4288 (m, 2H), 6.87-6.79 (m, 2H), 6.81 (d, J=3.9 Hz, 1H), 6.1138-6.0967 (m, 1H), 4.6115-4.4063 (m, 2H), 4.2648-4.1697 (m, 2H), 4.1276-4.0759 (m, 1H), 3.0117-2.7529 (m, 2H), 1.9097-1.8045 (m, 2H), 1.3463-1.2380 (m, 3H), 1.0103-0.9594 (m, 3H).

ESI-MS m/z=385.2, $[M+H]^+$.

Example 18

Synthesis of Compound N16

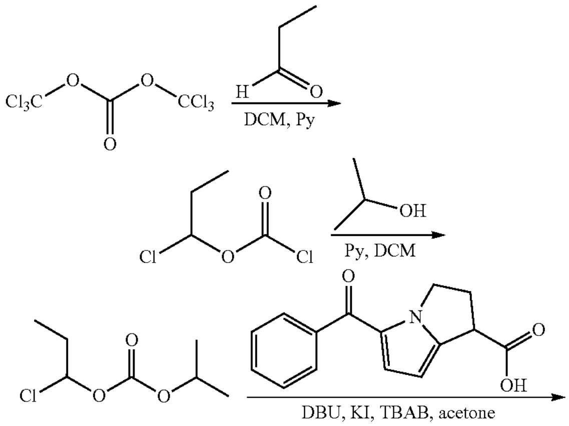

-continued

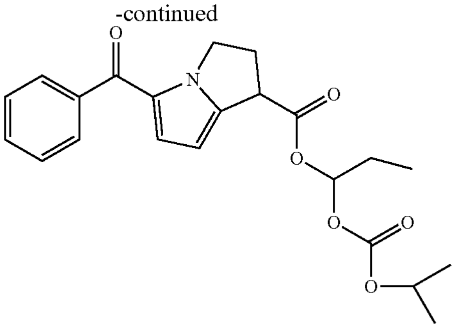

Synthesis of 1-chloropropyl chloroformate: triphosgene (10.00 g, 33.70 mmol) was weighed to a 100 mL three-necked reaction flask, 15 mL of anhydrous dichloromethane was added, the reaction flask was purged with Ar gas for 3 times, and the reaction flask was placed to a cold trap at −20° C. under constant stirring. Py (0.54 g, 6.83 mmol) was weighed and added with 5 mL of dichloromethane for dilution, and added to the reaction flask. Then n-propionaldehyde (4.6 g, 79.20 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (3.91 g, yield: 73.2%).

Synthesis of 1-chloropropyl isopropyl carbonate: 1-chloropropyl chloroformate (1.0 g, 6.38 mmol) was weighed to a dry two-necked reaction flask, 10 mL of anhydrous dichloromethane was added under constant stirring, isopropanol (0.58 g, 9.60 mmol) was weighed and added to the reaction flask described above, the reaction flask was placed in an ice-water bath under constant stirring, pyridine (0.63 g, 7.94 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (0.781 g), which was used directly in the next reaction step without further purification;

Synthesis of compound N16: ketorolac (0.73 g, 2.86 mmol) was weighed to a dry single-necked reaction flask, 10 mL of acetone was added and stirred to dissolve ketorolac, DBU (0.88 g, 5.78 mmol) and 0.72 g of the fresh-prepared 1-chloropropyl isopropyl carbonate were added, the reaction was performed at 40° C. for 1 h, KI (0.48 g, 2.90 mmol) and TBAB (0.19 g, 0.58 mmol) were added, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.61 g, yield: 53.40%).

$^1$H NMR (400 MHz, $CDCl_3$) δ 7.82-7.79 (m, 2H), 7.55-7.50 (m, 1H), 7.47-7.42 (m, 2H), 6.81 (t, 3.8 Hz, 1H), 6.68 (t, J=5.4 Hz, 1H), 6.12-6.09 (m, 1H), 4.94-4.82 (m, 1H), 4.62-4.53 (m, 1H), 4.49-4.40 (m, 1H), 4.12-4.07 (m, 1H), 3.01-2.89 (m, 1H), 2.87-2.75 (m, 1H), 1.91-1.83 (m, 2H); 1.33-1.27 (m, 6H), 1.01-0.95 (m, 3H).

ESI-MS m/z=400.2, $[M+H]^+$.

Example 19

Synthesis of Compound N16(S)

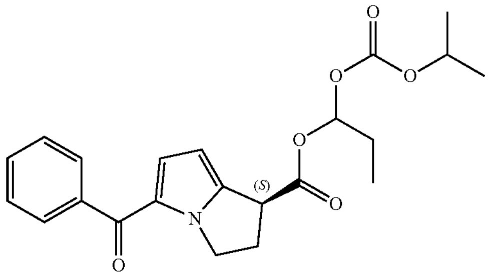

The procedure was the same as in Example 18, except that ketorolac was replaced with S-ketorolac;

$^1$H NMR (400 MHz, $CDCl_3$) δ 7.82-7.79 (m, 2H), 7.55-7.50 (m, 1H), 7.47-7.42 (m, 2H), 6.81 (t, J=3.8 Hz, 1H), 6.68 (t, J=5.4 Hz, 1H), 6.12-6.09 (m, 1H), 4.94-4.82 (m, 1H), 4.62-4.53 (m, 1H), 4.49-4.40 (m, 1H), 4.12-4.07 (m, 1H), 3.01-2.89 (m, 1H), 2.87-2.75 (m, 1H), 1.91-1.83 (m, 2H); 1.33-1.27 (m, 6H), 1.01-0.95 (m, 3H).

EST-MS m/z=400.2, $[M+H]^+$.

Example 20

Synthesis of Compound N17

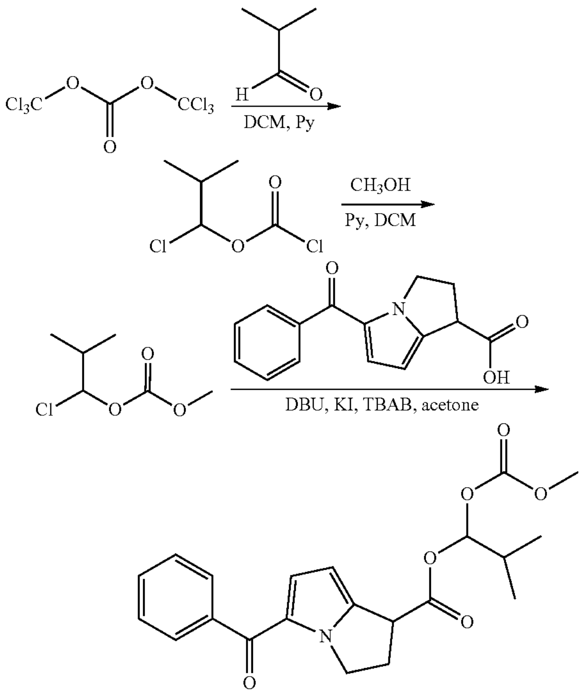

Synthesis oft-chloroisobutyl chloroformate: triphosgene (16.00 g, 53.92 mmol) was weighed to a 100 mL three-necked reaction flask, 30 mL of anhydrous dichloromethane was added, the reaction flask was purged with Ar gas for 3 times, and the reaction flask was placed to a −20° C. cold trap under constant stirring. Py (0.872 g, 11.02 mmol) was weighed and added with 4 mL of dichloromethane for dilution, and added to the reaction flask. Then n-propionaldehyde (7.44 g, 128.1 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (7.96 g, yield: 36.5%);

Synthesis of 1-chloroisobutyl methyl carbonate: 1-chloroisobutyl chloroformate (2.00 g, 11.7 mmol) was weighed to a dry two-necked reaction flask, 10 mL of anhydrous dichloromethane was added under constant stirring, methanol (0.57 g, 17.84 mmol) was weighed and added to the reaction flask described above, the reaction flask was placed in an ice-water bath under constant stirring, pyridine (1.12 g, 14.16 mmol) was weighed and added slowly and dropwise to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (1.205 g), which was used directly in the next reaction step without further purification;

Synthesis of compound N17: with reference to the above, ketorolac (0.792 g, 3.10 mmol) was weighed to a dry single-necked reaction flask, 10 mL of acetone was added and stirred to dissolve ketorolac, DBU (0.96 g, 6.3 mmol) and the fresh-prepared 1-chloropropyl methyl carbonate (0.775 g, 4.67 mmol) were added, the reaction was performed at 40° C. for 1 h, KI (0.516 g, 3.13 mmol) and TBAB (0.204 g, 0.624 mmol) were supplemented, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.703 g, yield: 58.75%).

$^1H$ NMR (400 MHz, $CDCl_3$) δ 7.82-7.78 (m, 2H), 7.55-7.51 (m, 1H), 7.47-7.43 (m, 2H), 6.82-6.80 (m, 1H), 6.57 (dd, J=3.6, 4.9 Hz, 1H), 6.12-6.09 (m, 1H), 4.61-4.53 (m, 1H), 4.49-4.41 (m, 1H), 4.21 (d, J=6.4 Hz, 3H), 4.13-4.08 (m, 1H), 3.03-2.75 (m, 2H), 2.13-2.04 (m, 1H), 1.02-0.96 (m, 6H).

ESI-MS m/z=386.2, $[M+H]^+$.

Example 21

Synthesis of Compound N18

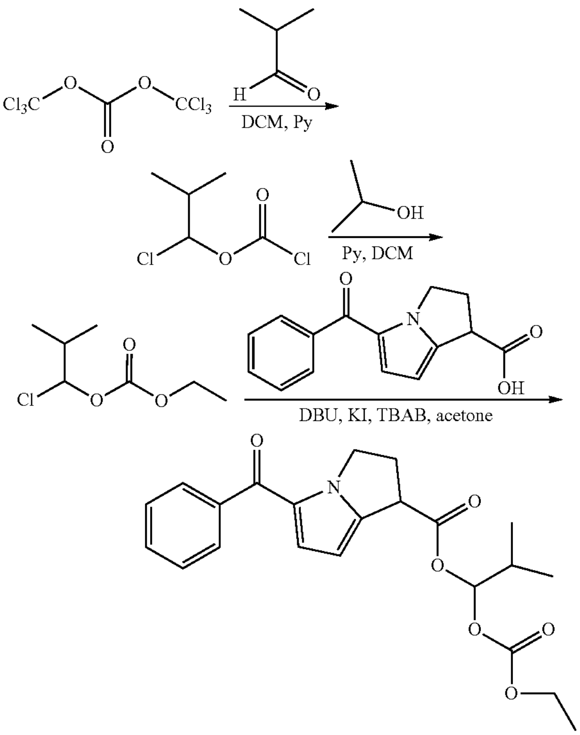

Synthesis of 1-chloroisobutyl chloroformate: triphosgene (20.00 g, 67.40 mmol) was weighed to a 100 mL three-necked reaction flask, 35 mL of anhydrous dichloromethane was added, the reaction flask was purged with Ar gas for 3 times, and the reaction flask was placed to a cold trap at −20° C. under constant stirring. Py (1.09 g, 13.78 mmol) was weighed, diluted with 5 mL of dichloromethane, and added to the reaction flask. Then n-propionaldehyde (9.30 g, 160.12 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (7.64 g, yield: 71.5%); Synthesis of 1-chloroisobutyl ethyl carbonate: 1-chloroisobutyl chloroformate (1.00 g and 5.85 mmol) was weighed to a dry two-necked reaction flask, 10 mL of anhydrous dichloromethane was added under constant stirring, ethanol (0.29 g and 8.92 mmol) was weighed to the reaction flask described above, the reaction flask was placed in an ice-water bath under constant stirring, pyridine (0.56 g and 7.08 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until was 3-4, then washed with water until it was nearly neutral, washed with saturated brine, dried over anhydrous sodium sulfate, and concentrated under reduced pressure to give a colorless oil (0.695 g), which was used directly in the next reaction step without further purification;

Synthesis of compound N18: with reference to the above, ketorolac (0.66 g, 2.59 mmol) was weighed to a dry single-necked reaction flask, 10 mL of acetone was added and stirred to dissolve ketorolac, DBU (0.8 g, 5.25 mmol) and 0.67 g of the fresh-prepared 1-chloroisobutyl ethyl carbonate were added, the reaction was performed at 40° C. for 1 h, KI (0.43 g, 2.61 mmol) and TBAB (0.17 g, 0.52 mmol) were supplemented, and the reaction solution was kept warm and reacted for 2-6 h, Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.63 g, yield: 55.15%).

$^1H$ NMR (400 MHz, $CDCl_3$) δ 7.82-7.78 (m, 2H), 7.55-7.51 (m, 1H), 7.47-7.43 (m, 2H), 6.82-6.80 (m, 1H), 6.57 (dd, J=3.6, 4.9 Hz, 1H), 6.12-6.09 (m, 1H), 4.61-4.53 (m, 1H), 4.49-4.41 (m, 1H), 4.27-4.14 (m, 2H), 4.13-4.08 (m, 1H), 3.03-2.75 (m, 2H), 2.13-2.04 (m, 1H), 1.35-1.25 (m, 3H), 1.02-0.96 (m, 6H).

ESI-MS m/z=400.2, $[M+H]^+$.

Example 22

Synthesis of Compound N19

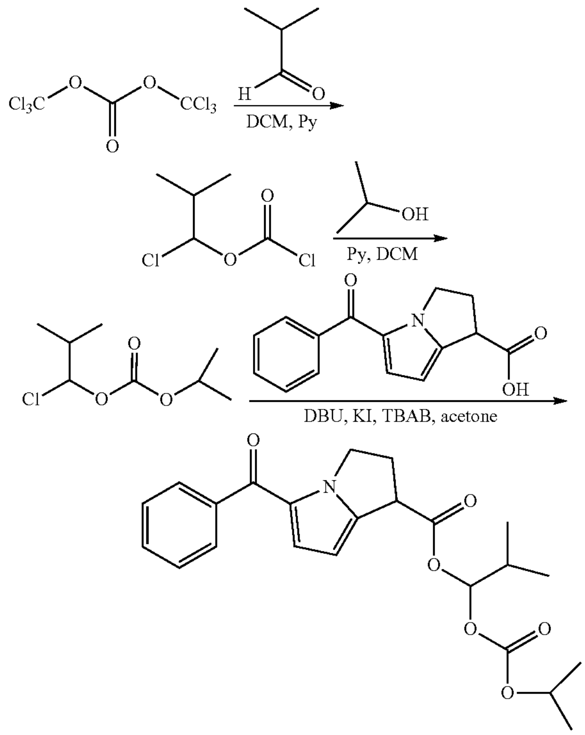

Synthesis of 1-chloroisobutyl chloroformate: triphosgene (20.00 g, 67.40 mmol) was weighed to a 100 mL three-necked reaction flask, 35 mL of anhydrous dichloromethane was added, the reaction flask was purged with Ar gas for 3 times, and the reaction flask was placed to a cold trap at −2° C. under constant stirring. Py (1.09 g, 13.78 mmol) was weighed, diluted with 5 mL of dichloromethane, and added to the reaction flask. Then n-propionaldehyde (9.30 g, 160.12 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (7.64 g, yield: 71.5%);

Synthesis of 1-chloroisobutyl isopropyl carbonate: 1-chloroisobutyl chloroformate (1.00 g, 5.85 mmol) was weighed to a dry two-necked reaction flask, 10 mL of anhydrous dichloromethane was added under constant stirring, isopropanol (0.53 g, 8.78 mmol) was weighed and added to the reaction flask described above, the reaction flask was placed in an ice-water bath under constant stirring, pyridine (0.57 g, 7.21 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (0.755 g), which was used directly in the next reaction step without further purification;

Synthesis of compound N19: ketorolac (0.66 g, 2.59 mmol) was weighed to a dry single-necked reaction flask, 10 mL of acetone was added and stirred to dissolve ketorolac, DIRT (0.80 g, 5.25 mmol) and 0.65 g of the fresh-prepared 1-chloroisobutyl isopropyl carbonate were added, the reaction was performed at 40° C. for 1 h, KI (0.43 g, 2.61 mmol) and TBAB (0.17 g, 0.52 mmol) were supplemented, and the reaction solution was kept warm and reacted for 2-6 h, Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/FA=8:1) to give a colorless oil (0.56 g, yield: 47.36%).

$^1H$ NMR (400 MHz, $CDCl_3$) δ 7.82-7.79 (m, 2H), 7.55-7.50 (m, 1H), 7.47-7.42 (m, 2H), 6.81 (t, J=4.0 Hz, 1H), 6.56 (dd, J=5.0, 2.6 Hz, 1H), 6.13-6.09 (m, 1H), 4.94-4.82 (m, 1H), 4.61-4.53 (m, 1H), 4.49-4.41 (m, 1H), 4.13-4.08 (m, 1H), 3.03-2.75 (an, 2H), 2.14-2.05 (m, 1H), 1.33-1.27 (m, 6H), 1.02-0.96 (m, 6H);

ESI-MS m/z=414.3, $[M+H]^+$.

Example 23

Synthesis of Compound N20

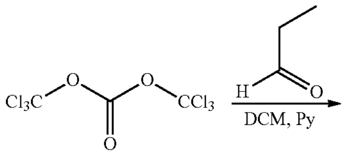

-continued

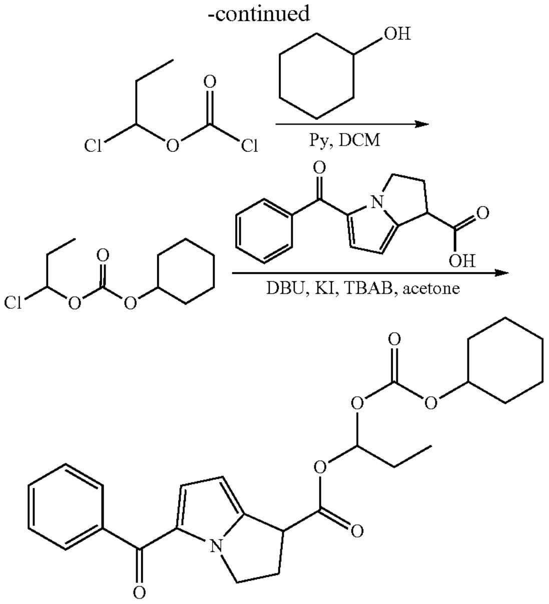

Synthesis of 1-chloropropyl chloroformate: triphosgene (5.00 g, 16.85 mmol) was weighed to a 100 mL three-necked reaction flask, 10 mL of anhydrous dichloromethane was added, the reaction flask was purged with Ar gas for 3 times, and the reaction flask was placed to a cold trap at −20° C. under constant stirring, Py (0.27 mg, 3.41 mg) was weighed, diluted with 5 mL of dichloromethane, and added to the reaction flask. Then n-propionaldehyde (2.3 g, 39.60 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (2.01 g, yield: 75.3%);

Synthesis of 1-chloropropyl cyclohexyl carbonate: 1-chloropropyll chloroformate (1.882 g, 12.0 mmol) was weighed to a dry two-necked reaction flask, 10 mL of anhydrous dichloromethane was added under constant stirring, cyclohexanol (1.820 g, 18.0 mmol) was weighed to the reaction flask described above, the reaction flask was placed in an ice-water bath under constant stirring, pyridine (1.259 g, 14.76 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (2.702 g), which was used directly in the next reaction step without further purification;

Synthesis of compound N20: ketorolac (0.872 g, 3.41 mmol) was weighed to a dry single-necked reaction flask, 5 mL of acetone was added and stirred to dissolve ketorolac, (1.037 g, 6.82 mmol) and the fresh-prepared 1-chloropropyl cyclohexyl carbonate (1.354 g, 6.06 mmol) were added, the reaction was performed at 40° C. for 1 h, KI (0.592 g, 3.41 mmol) and TBAB (0.235 g, 0.68 mmol) were supplemented, and the reaction solution was kept warm and reacted for 2-6 h. Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.98 g, yield: 65.3%).

$^1H$ NMR (400 MHz, $CDCl_3$) δ 7.82-7.79 (m, 2H), 7.55-7.50 (m, 1H), 7.47-7.42 (m, 2H), 6.80 (t, J=4.6 Hz, 1H), 6.08 (t, J=5.4 Hz, 1H), 6.12-6.09 (m, 1H), 4.67-4.53 (m, 2H), 4.48-4.41 (m, 1H), 4.15-4.07 (m, 1H), 3.01-2.89 (m, 1H), 2.86-2.74 (m, 1H), 1.93-1.84 (m, 4H), 1.77-1.72 (m, 2H), 1.57-1.43 (m, 3H), 1.41-1.30 (m, 3H), 1.01-0.95 (m, 3H).

ESI-MS m/z=440.2, $[M+H]^+$.

Example 24

Synthesis of Compound N21

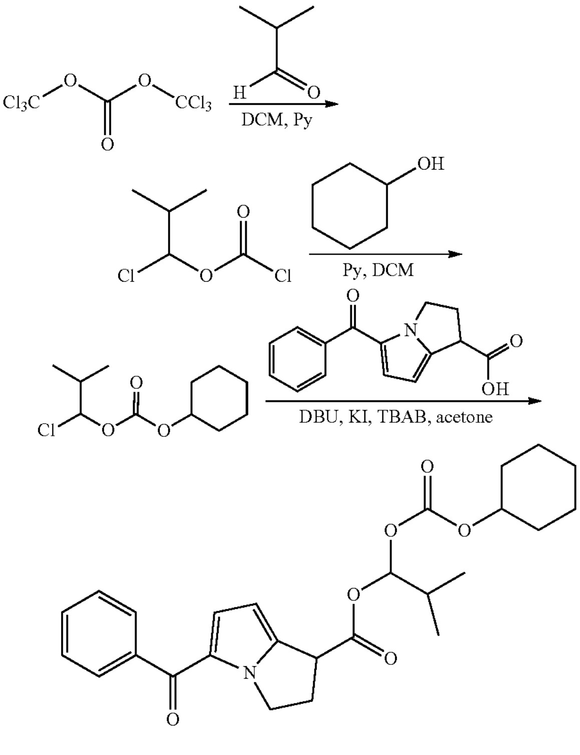

Synthesis of 1-chloroisobutyl chloroformate: triphosgene (10.00 g, 38.70 mmol) was weighed to a 50 mL three-necked reaction flask, 25 mL of anhydrous dichloromethane was added, the reaction flask was purged with Ar gas for 3 times, and the reaction flask was placed to a cold trap at −20° C. under constant stirring. Py (0.55 mg, 6.95 mmol) was weighed, diluted with 5 mL of dichloromethane, and added to the reaction flask. Then n-propionaldehyde (4.7 g, 80.92 mmol) was weighed and added slowly and dropwise to the reaction flask, and after the dropwise addition was completed, the temperature of the cold trap was set at −2° C., and the reaction was continued for 20 h. The reaction flask containing KOH aqueous solution was pumped to a water pump for 5 min before being removed from the cold trap, concentrated under reduced pressure to remove dichloromethane, and then distilled to give a colorless to light yellow oil (3.82 g, 71.5%);

Synthesis of 1-chloroisobutyl cyclohexyl carbonate: 1-chloroisobutyl chloroformate (1.0 g, 5.88 mmol) was weighed to a dry two-necked reaction flask. 10 mL of anhydrous dichloromethane was added under constant stirring, cyclohexanol (0.883 g, 8.82 mmol) was weighed to the reaction flask described above, the reaction flask was placed in an ice-water bath under constant stirring, pyridine (0.558 g, 7.05 mmol) was weighed and added slowly to the reaction flask described above, a white solid produced during the dropwise addition process, and after the dropwise addition was completed, the reaction flask was placed at room temperature and reacted for 1 h. 10 mL of water was added to the reaction flask, followed by liquid separation, the dichloromethane layer was washed with 5% $KHSO_4$ until pH was 3-4, then washed with water until it was nearly neutral, washed with saturated brine, dried over anhydrous sodium sulfate, and concentrated under reduced pressure to give a colorless oil (0.86 g), which was used directly in the next reaction step without further purification;

Synthesis of compound N21: ketorolac (0.5 g, 1.96 mmol) was weighed to a dry single-necked reaction flask, 5 mL of acetone was added and stirred to dissolve ketorolac, DBU (0.45 g, 3.41 mmol) and the fresh-prepared 1-chloroisobutyl cyclohexyl carbonate (0.798 g, 3.41 mmol) were added, the reaction was performed at 40° C. for 1 h, KI (0.325 g, 1.96 mmol) and TBAB (0.126 g, 0.39 mmol) were supplemented, and the reaction solution was kept warm and reacted for 2-6 h.

Dichloromethane and water were added to the reaction, followed by liquid separation, and the dichloromethane layer was washed with 5% $NaHCO_3$ aqueous solution, washed with water and saturated brine, dried, and concentrated, and the residue was subjected to flash column chromatography (PE/EA=8:1) to give a colorless oil (0.51 g, yield: 58.5%).

$^1H$ NMR (400 MHz, $CDCl_3$) δ 7.83-7.79 (m, 2H), 7.54-7.9 (m, 1H), 7.47-7.41 (m, 2H), 6.84-6.78 (m, 1H), 6.10 (t, J=5.4 Hz, 1H), 6.12-6.10 (m, 1H), 4.68-4.52 (m, 2H), 4.48-4.42 (m, 1H), 4.16-4.05 (m, 1H), 3.03-2.91 (m, 1H), 2.88-2.75 (m, 1H), 2.06-1.88 (m, 3H), 1.79-1.71 (m, 2H), 1.58-1.42 (m, 3H), 1.44-1.32 (m, 3H), 1.03-0.93 (m, 6H).

EST-MS m/z=454.4, $[M+H]^+$.

Example 25

Synthesis of Compound N22

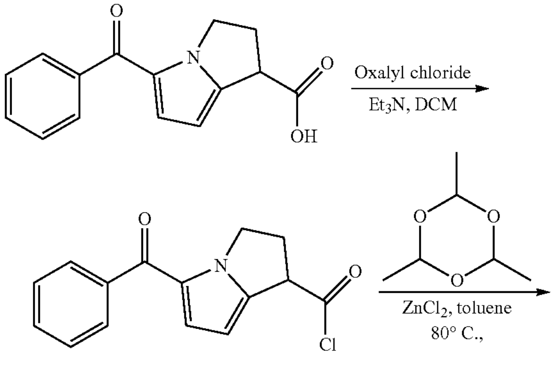

-continued

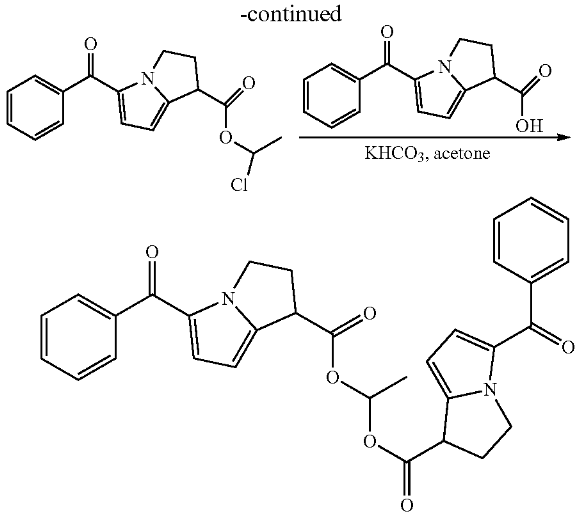

Synthesis of ketorolac chloride: ketorolac (1.0 g, 3.92 mmol) was weighed to a 50 mL pre-dried two-necked reaction flask, 10 mL of anhydrous dichloromethane was added, the reaction flask was purged with $N_2$ for 2 times under constant stirring, the reaction flask was placed in the ice bath under constant stirring, 5 drops of DMF were added, then oxalyl chloride (0.746 g, 5.88 mmol) was added slowly and dropwise to the reaction flask, and after the dropwise addition was completed, the reaction solution was kept in the ice bath and reacted for 2 h, and concentrated under reduced pressure to remove the solvent to give a yellow oil (0.92 g), which was used directly in the next reaction step without further purification;

Synthesis of 1-chloroethyl ketorolac ester: The fresh-prepared ketorolac chloride (0.92 g, 3.37 mmol) was placed in a 50 mL two-necked reaction flask under $N_2$ atmosphere, and anhydrous $ZnCl_2$ (46 mg, 0.337 mmol) was added to the reaction flask. Anhydrous toluene (20 ml) was then weighed and added to the reaction flask, and the reaction flask was placed in an ice bath under constant stirring. After paraldehyde (147 mg, 1.11 mmol) was weighed, diluted with 5 mL of toluene, and added slowly and dropwise to the reaction flask described above, and after the dropwise addition was completed, the reaction was heated to 80° C. and performed for 6 h. 10 mL of water was added to the reaction flask, followed by liquid separation, the dichloromethane layer was washed with 5% $NaHCO_3$ aqueous solution for 2 times until pH was about 9, then washed with water again and with saturated brine, dried over anhydrous sodium sulfate, and concentrated under reduced pressure to give a yellowish-brown oil (0.91 g, crude), namely 1-chloroethyl ketorolac ester, which was used directly in the next reaction step without further purification;

Synthesis of compound N22: ketorolac (0.5 g, 1.96 mmol) and $KHCO_3$ (0.3 g, 3.0 mmol) were weighed to a 50 mL single-necked reaction flask, 10 mL of acetone was added under constant stirring, then 1-chloroethyl ketorolac ester (0.93 g, 2.93 mmol) was weighed to the reaction flask, and the reaction was heated to 60° C. and performed for 6 h. Dichloromethane and water were added to the reaction, followed by liquid separation, and the di chloromethane layer was washed with 5% $NaHCO_3$ aqueous solution, washed with water and saturated brine, dried, and concentrated, and the residue was subjected to flash column chromatography (PE/EA=3:1) to give a yellow oil (332.09 mg, yield: 31.6%).

$^1$H NMR (400 MHz, $CDCl_3$) δ 7.8301-7.8106 (m, 4H), 7.5671-7.5201 (m, 2H), 7.4856-7.45276 (m, 4H), 6.9409-6.8896 (m, 2H), 6.8448-6.8250 (m, 1H), 6.1611-6.1.1026 (m, 2H), 4.6335-4.5599 (m, 2H), 4.4835-4.4213 (m, 2H), 4.0994-4.0534 (m, 2H), 2.9910-2.8786 (m, 2H), 2.8511-2.7639 (m, 2H), 1.5349 (q, 3H, J=2.7 Hz);

ESI-MS m/z=537.2, $[M+H]^+$.

Example 26

Synthesis of Compound N26 tion, the filtrate was separated, and the organic phase was collected. The organic phase was washed with 10% sodium thiosulfate solution (300 mL), water (200 mL) and saturated brine (200 mL), dried over anhydrous sodium sulfate and concentrated to give 56.51 g of crude product, which was used directly in the next step without purification.

Synthesis of compound N26: M02 (56.51 g, 0.172 mol) and ketorolac (48.31 g, 0.189 mol) were weighed and placed to the reaction flask, ethyl acetate (500 mL) was added and the dissolution was found to be not completed, and then tetrahydrofuran (100 mL) was added for improving dissolution in an ice bath. Triethylamine (26.11 g, 0.258 mol) was

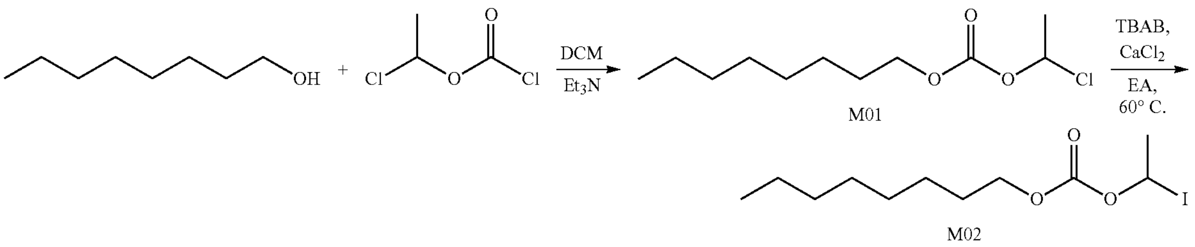

M01
M02

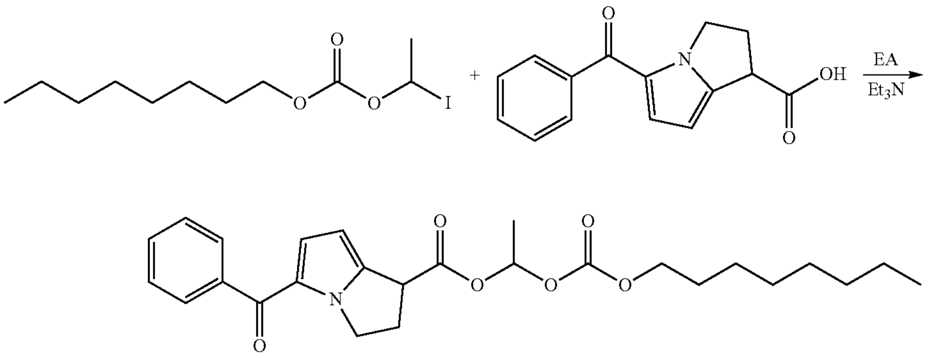

Synthesis of M01: n-octanol (29.1 g, 0.223 mol) and 1-chloroethyl chloroformate (40.0 g, 0.280 mol) were weighed to a reaction flask, and dissolved in dichloromethane (300 mL) and placed in an ice bath. Triethylamine (34.0 g, 0.336 mol) was diluted with dichloromethane (50 mL) and added dropwise to the reaction flask in an ice bath over about 1 h. After the dropwise addition was completed, the ice bath was removed, and the reaction was performed at room temperature overnight. The next day, the reaction solution was subjected to suction filtration, and the filter cake was washed with dichloromethane (50 mL×3). The filtrate was washed with 1% citric acid solution (500 mL), water (300 mL) and saturated brine (300 mL), dried over anhydrous sodium sulfate, and concentrated to give M01 (54.83 g, crude), which was used directly in the next step without purification.

Synthesis of M02: M01 (54.83 g, 0.229 mol), sodium iodide (69.41 g, 0.463 mol), calcium chloride (7.70 g, 0.069 mol) and TBAB (4.47 g, 0.014 mol) were weighed and placed in the reaction flask, and dissolved in ethyl acetate (500 mL). The reaction was heated to 60° C., kept warm and stirred for 3 h. The reaction solution was subjected to suction filtration, and the filter cake was washed with ethyl acetate (50 mL). The filtrate was concentrated, and the concentrate was added with n-hexane (300 mL) and water (200 mL), stirred at room temperature, and subjected to suction filtraweighed and added dropwise to the reaction flask over about 30 min. The ice bath was removed, and the reaction was performed under stirring at room temperature overnight. The next day, the reaction solution was subjected to suction filtration, and the filter cake was washed with ethyl acetate (50 mL×3). The reaction solution was washed with water (300 mL), the aqueous layer was extracted with ethyl acetate (150 mL×3), and the organic phases were combined, washed with 10% sodium carbonate solution (300 mL), water (300 mL) and saturated brine (300 mL), dried over anhydrous sodium sulfate, and concentrated, and the residue was subjected to flash column chromatography (wet loading, PE/EA=15:1) and concentrated. The concentrate was dissolved in ethyl acetate, and added with activated charcoal (1.35 g), followed by stirring in a water bath at 40° C., and subjected to suction filtration after about 1 h, the filtrate was collected and concentrated to give compound N26 (20.98 g, yield: 26.76%);

$^1$H NMR (400 MHz, $CDCl_3$) δ 7.81-7.79 (m, 2H), 7.55-7.50 (m, 1H), 7.46-7.42 (m, 2H), 6.83-6.80 (m, 2H), 6.11-6.09 (m, 1H), 4.58-4.23 (m, 2H), 4.15-4.06 (m, 3H), 2.95-2.78 (m, 214), 1.61-1.55 (m, 5H), 1.31-1.25 (m, 10H), 0.88-0.85 (m, 3H).

ESI-MS m/z=494.1 $[M+K]^+$.

Example 27

Synthesis of Compound N27

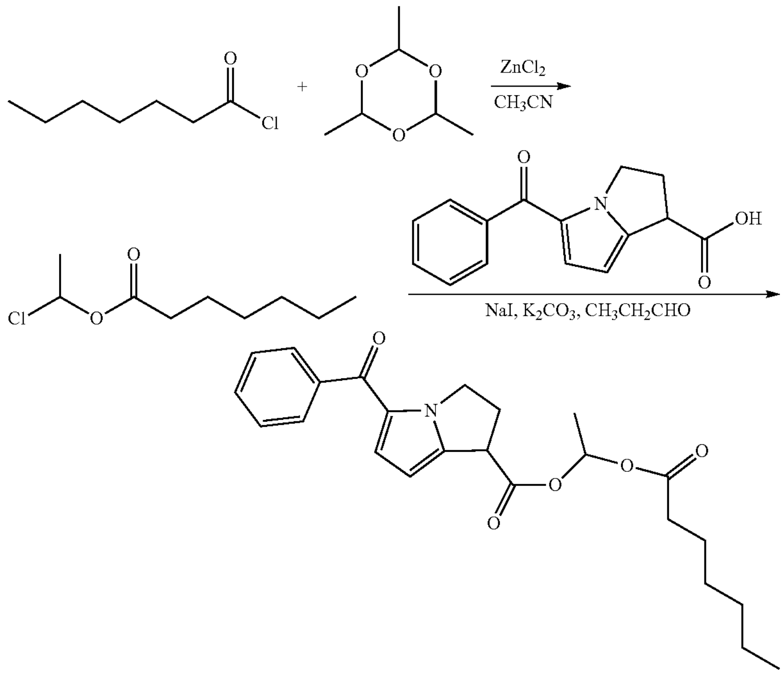

Synthesis of 1-chloroethyl heptanoate: heptanoyl chloride (1000 g, 0.068 mol) was weighed to a three-necked flask, dissolved in acetonitrile (50 mL), then added with zinc chloride (0.02 g) and 4A molecular sieves (0.50 g), and purged with nitrogen for 3 times in an ice bath. Paraldehyde (3.1 g, 0.023 mol) was added dropwise over 30 min, the reaction solution was placed in a water bath at 60° C. for heating, and the reaction was completed after 3.5 h. The reaction solution was subjected to suction filtration, and the filter cake was washed with ethyl acetate (50 mL×3). The filtrate was concentrated to give 12.63 g of crude product, which was used directly in the next reaction without purification.

Synthesis of compound N27: ketorolac (8.48 g, 0.033 mol), potassium carbonate (6.82 g, 0.049 mol) and sodium iodide (5.05 g, 0.034 mol) were weighed and placed to a reaction flask, acetone (150 mL) was added and stirred to dissolve the mixture at room temperature. 1-chloroethyl heptanoate (12.63 g, 0.066 mol) was weighed and added dropwise to the reaction flask. After the dropwise addition was completed, the reaction was performed at room temperature overnight. The next day, the reaction solution was subjected to suction filtration, the filtrate was concentrated, and the concentrate was dissolved in ethyl acetate (100 mL). The solution was washed with water (100 mL), 10% sodium bicarbonate solution (100 mL) and saturated brine (100 mL), dried, and concentrated, and the residue was subjected to flash column chromatography (wet loading, PE/EA=15:1) to give compound N27 (4.29 g, yield: 31.59%);

$^1$H NMR (400 MHz, CDCl$_3$) δ 7.8211-7.8028 (d, 2H, 7.3 Hz), 7.5452-7.5090 (t, 1H, J=7.3 Hz), 7.4665-7.4293 (t, 2H, J=7.6 Hz), 6.9381-6.8975 (q, 1H, J=5.4 Hz), 6.8195-6.8098 (d, 1H, J=4.0 Hz), 6.1031-6.0842 (t, 1H, J=3.8 Hz), 4.6117-4.5388 (m, 1H), 4.4745-4.3959 (m, 1H), 4.0846-4.0500 (t, 1H, J=7.7 Hz), 2.9828-2.8764 (m, 1H), 2.8428-2.7521 (m, 1H), 2.3893-2.3105 (m, 2H), 1.5241-1.5037 (m, 5H), 1.2563-1.1918 (m, 6H), 1.1681-1.1076 (q, 3H, J=7.6 Hz); ESI-MS m/z=412.5, [M+H]$^+$.

Comparative Example 1

Synthesis of Compound N11

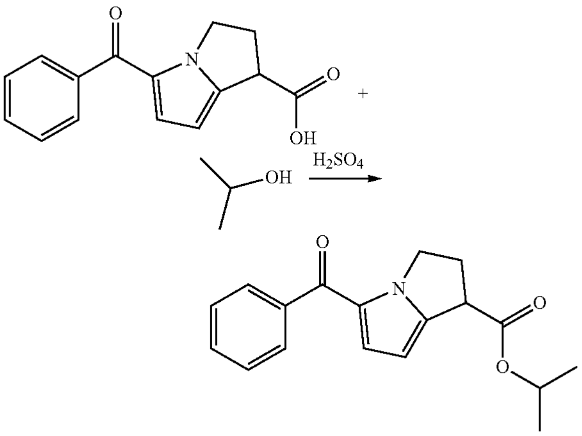

At room temperature, 1.0 g of ketorolac was weighed to a 50 mL dry reaction flask, 5 mL of isopropanol was added and stirred to dissolve ketorolac, then 0.5 mL of concentrated sulfuric acid was added slowly to the reaction flask, and after the dropwise addition was completed, the reaction was continued at room temperature for 2 h, and water (10 mL) and ethyl acetate (30 mL) were added to the reaction flask, followed by liquid separation, the organic layer was washed with 5% $NaHCO_3$ aqueous solution, dried over anhydrous sodium sulfate, concentrated and subjected to flash column chromatography (PE/EA=6:1) to give the target product (1.05 g, yield: 91%);

$^1H$ NMR (400 MHz, $CDCl_3$) δ 7.8254-7.8014 (m, 2H), 7.5459-7.5024 (m, 1H), 7.4650-7.4255 (m, 2H), 6.8197-6.8098 (m, 1H), 6.0940-6.0823 (m, 1H), 5.1195-5.0256 (m, 1H), 4.6155-4.5501 (m, 1H), 4.4640-4.3973 (m, 1H), 4.0436-4.0064 (m, 1H), 2.9737-2.8888 (m, 1H), 2.8199-2.7300 (m 1H), 1.2950-1.2641 (t, 6H, J=6.2 Hz);

The side chain of the ketorolac derivative represented by compound N21 was selected from fatty chains, which was used as a control compound for the compounds of the present disclosure.

Comparative Example 2

The listed drug flurbiprofen axetil (FPA) was purchased as a control compound for the compounds of the present disclosure.

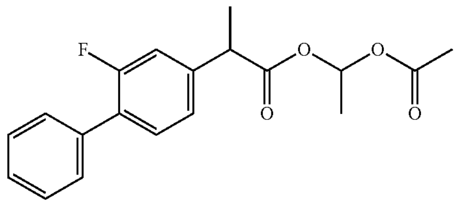 [SMILES: CC(=O)OC(C)OC(=O)C(C)c1ccc(-c2ccccc2)c(F)c1]

Test Example 1: High Temperature Stability Study of Compounds

Test protocol: the compounds prepared in the present disclosure were placed in a colorless and transparent vial, placed in the dark at a high temperature (60° C.), and were sampled for day 0, day 5 and day 10, respectively, and the purity of the compounds and the change of the related substance (ketorolac) were determined. The results are shown in Table 1:

TABLE 1

| | | Day 0 | Day 5 | Day 10 |
|---|---|---|---|---|
| N2 | Total main peak purity (%) | 95.58 | 95.21 | 94.82 |
| | Ketorolac (%) | 0.03 | 0.04 | 0.05 |
| N3 | Total main peak purity (%) | 92.45 | 90.83 | 90.36 |
| | Ketorolac (%) | 0.11 | 0.15 | 0.17 |
| N4 | Total main peak purity (%) | 98.91 | 98.38 | 98.04 |
| | Ketorolac (%) | 0.12 | 0.17 | 0.14 |
| N5 | Total main peak purity (%) | 97.46 | 97.62 | 97.37 |
| | Ketorolac (%) | 0.14 | 0.15 | 0.17 |
| N6 | Total main peak purity (%) | 91.56 | 90.94 | 90.22 |
| | Ketorolac (%) | 0.14 | 0.13 | 0.17 |
| N7 | Total main peak purity (%) | 90.83 | 88.66 | 88.59 |
| | Ketorolac (%) | 0.18 | 0.25 | 0.32 |
| N8 | Total main peak purity (%) | 93.15 | 93.30 | 92.34 |
| | Ketorolac (%) | 0.18 | 0.42 | 0.96 |
| N9 | Total main peak purity (%) | 96.21 | 95.58 | 95.21 |
| | Ketorolac (%) | 0.29 | 0.31 | 0.30 |

TABLE 1-continued

| | | Day 0 | Day 5 | Day 10 |
|---|---|---|---|---|
| N10 | Total main peak purity (%) | 96.36 | 94.28 | 94.41 |
| | Ketorolac (%) | 0.05 | 0.23 | 0.37 |
| N12 | Total main peak purity (%) | 93.84 | 93.59 | 93.36 |
| | Ketorolac (%) | 0.03 | 0.07 | 0.07 |
| N15 | Total main peak purity (%) | 96.30 | 95.87 | 95.59 |
| | Ketorolac (%) | 0.08 | 0.09 | 0.14 |
| N16 | Total main peak purity (%) | 97.33 | 96.50 | 96.16 |
| | Ketorolac (%) | 0.05 | 0.07 | 0.07 |
| N18 | Total main peak purity (%) | 94.25 | 92.10 | 91.78 |
| | Ketorolac (%) | 0.06 | 0.18 | 0.26 |
| N19 | Total main peak purity (%) | 96.30 | 94.61 | 94.41 |
| | Ketorolac (%) | 0.07 | 0.09 | 0.12 |

As can be seen from the test results, the compounds of the present disclosure could all maintain relatively high stability at 60° C.

Test Example 2: Stability Study of Levorotatory Enantiomer of Compounds in Solvent 1. Test protocol: the compounds (N2(S), N12(S), N15(S) and N16 (S)) were dissolved in medium-chain triglyceride (MCT), and the resulting samples were kept at 5° C., 25° C. and 60° C. and sampled at day 0, day 5, day 15 and day 30, respectively, and the purity of the compounds, the change of the related substance (ketorolac) and the change in the isomer (dextrorotatory form) were determined.

2. Test method: the samples were prepared according to Table 2, wherein each sample was dispensed into 10 vials according to the lofting volume, and the samples were lofted according to Table 3.

TABLE 2

Investigation of sample formula with solution stability

| | Total formulation amount (g) | Concentration of drug substances (mg/g) | Dosage of drug substances (g) | Dosage of sample for single detection (g) | Dosage of solvent (g) |
|---|---|---|---|---|---|
| Drug-containing MCT solution | 12 | 50 | 0.6 | 1 | 11.4 |

TABLE 3

Lofting location, investigation condition and time

| Investigation condition | Instruments and equipment | Sampling detection time (d) | | | |
|---|---|---|---|---|---|
| | | 0 | 5 | 15 | 30 |
| 2-8° C., in the dark | Analysis refrigerator | ✓ | ✓ | ✓ | ✓ |
| 25° C., in the dark | Formulation stability kit | / | ✓ | ✓ | ✓ |
| 60° C., in the dark | Formulation oven | / | ✓ | ✓ | ✓ |

"✓" denotes that the relevant substance and isomer were determined;
"/" denotes that they were undeterminable.

3. Procedures:

(1) Sample Preparation:

① Preparation of drug-containing MCT solution: 6 g of the drug substances of compounds N2(S), N12(S), N15(S) and N16(S) were weighed, respectively, 9 g of MCT was added, and the reaction solution was magnetically stirred for 20 min.

(2) Packaging and Sample Retention:

① Each batch of the drug-containing MCT solution was packaged into 10 vials, followed by marking the name and the batch number.

② Three vials from each batch of the samples were stored in a light-tight box, followed by investigation and sample retention according to the conditions in the experimental method.

(3) Samples Were Sent at Day 0:

① One vial was taken from each batch of the samples as sample at day 0.

② Samples were sent for analysis to detect the related substance and isomer.

4. The related substance was determined according to high performance liquid chromatography (General Chapter 0512, China Pharmacopoeia, 2015 Edition).

(1) Chromatographic conditions: the chromatography column was Agilent ZORBAX SB-C8, 4.6 mm×250 mm, 5 μm, and 0.1% phosphoric acid solution-acetonitrile (50:50) was used as a mobile phase; the detection wavelength was 310 am; the flow rate was 1.0 mL/min; the column temperature was 40° C., and linear gradient elution was performed according to the following table;

(2) Determination method: an appropriate amount of the product was weighed precisely, a diluent (absolute ethanol) was added and shaken to dissolve, and quantitatively diluted to give a solution containing 0.4 mg per 1 mL, the solution was thawed by vortex for 30 s, and filtered with PTFE filter membrane (0.22 μm, JINTENG), and the filtrate was collected as a test sample solution. 10 μL of the solution was weighed precisely and injected into a liquid chromatograph, and a chromatogram was recorded; if an impurity peak existed in the chromatogram of the test sample solution, calculation was performed according to a peak area normalization method to give the target product.

5. Isomer determination was performed according to high performance liquid chromatography (General Chapter 0512, China Pharmacopoeia, 2015 Edition).

(1) Chromatographic conditions: cellulose-tris(3,5-dimethylphenylcarbamate)silica gel was used as filler (Chiralcel OD-H, 250×4.6 mm, 5 μm); n-hexane-isopropanol (90:10) was used as a mobile phase, and isocratic elution was performed for 25 min at a flow rate of 1.0 mL/min; the column temperature was 35° C.; the detection wavelength was 310 nm.

(2) Determination method: an appropriate amount of the product was weighed precisely, a diluent (n-hexane-isopropanol (90:10)) was added and shaken to dissolve, and quantitatively diluted to give a solution containing about 1.0 mg per 1 mL, the solution was thawed by vortex for 30 s, and filtered with PTFE filter membrane (0.22 μm, JINTENG), and the filtrate was collected as a test sample solution. 20 μL of the solution was weighed precisely and injected into a liquid chromatograph, and a chromatogram was recorded; if an isomer peak existed in the chromatogram of the test sample solution, calculation was performed according to a peak area normalization method to give the target product.

The test results are shown in Table 4:

TABLE 4

| Name and Lot No. | Lofting conditions | Time | Ketorolac (%) | Purity (%) | Isomer (%) |
|---|---|---|---|---|---|
| N2(S) MCT solution | 5° C. | 0 | 0.16 | 99.14 | 5.65 |
| | | Day 5 | 0.2 | 99.08 | 5.63 |
| | | Day 15 | 0.14 | 99.18 | 5.87 |
| | | Day 30 | 0.25 | 99.01 | 5.99 |
| | 25° C. | 0 | 0.16 | 99.14 | 5.65 |
| | | Day 5 | 0.21 | 99.08 | 5.66 |
| | | Day 15 | 0.17 | 99.13 | 5.86 |
| | | Day 30 | 0.28 | 98.95 | 6.01 |
| | 60° C. | 0 | 0.16 | 99.14 | 5.65 |
| | | Day 5 | 0.3 | 98.92 | 5.7 |
| | | Day 15 | 0.49 | 98.67 | 5.89 |
| | | Day 30 | 0.65 | 98.38 | 6.13 |
| N12(S) MCT solution | 5° C. | 0 | 0.02 | 99.65 | 3.01 |
| | | Day 5 | 0.02 | 99.62 | 3.05 |
| | | Day 15 | 0.02 | 99.64 | 3.07 |
| | | Day 30 | 0.03 | 99.55 | 3.06 |
| | 25° C. | 0 | 0.02 | 99.65 | 3.01 |
| | | Day 5 | 0.03 | 99.59 | 3.04 |
| | | Day 15 | 0.04 | 99.61 | 3.09 |
| | | Day 30 | 0.07 | 99.49 | 3.11 |
| | 60° C. | 0 | 0.02 | 99.65 | 3.01 |
| | | Day 5 | 0.09 | 99.53 | 3.12 |
| | | Day 15 | 0.23 | 99.35 | 3.1 |
| | | Day 30 | 0.41 | 99.05 | 3.48 |
| N15(S) MCT solution | 5° C. | 0 | 0.03 | 99.48 | 4.59 |
| | | Day 5 | 0.02 | 99.46 | 4.58 |
| | | Day 15 | 0.02 | 99.45 | 4.73 |
| | | Day 30 | 0.03 | 99.38 | 4.62 |
| | 25° C. | 0 | 0.03 | 99.48 | 4.59 |
| | | Day 5 | 0.03 | 99.42 | 4.58 |
| | | Day 15 | 0.03 | 99.41 | 4.72 |
| | | Day 30 | 0.05 | 99.33 | 4.64 |
| | 60° C. | 0 | 0.03 | 99.48 | 4.59 |
| | | Day 5 | 0.06 | 99.35 | 4.59 |
| | | Day 15 | 0.17 | 99.21 | 4.75 |
| | | Day 30 | 0.35 | 98.92 | 4.63 |
| N16(S) MCT solution | 5° C. | 0 | 0.02 | 99.71 | 2.46 |
| | | Day 5 | 0.03 | 99.55 | 2.47 |
| | | Day 15 | 0.02 | 99.65 | 2.6 |
| | | Day 30 | 0.03 | 99.52 | 2.58 |
| | 25° C. | 0 | 0.02 | 99.71 | 2.46 |
| | | Day 5 | 0.03 | 99.52 | 2.47 |
| | | Day 15 | 0.03 | 99.63 | 2.6 |
| | | Day 30 | 0.04 | 99.48 | 2.59 |
| | 60° C. | 0 | 0.02 | 99.71 | 2.46 |
| | | Day 5 | 0.05 | 99.52 | 2.48 |
| | | Day 15 | 0.12 | 99.51 | 2.61 |
| | | Day 30 | 0.24 | 99.27 | 2.63 |

According to the test results, the levorotatory isomer corresponding to the compound of the present disclosure could be placed in an oil phase for 30 days at different temperatures, and the related substance and the isomer could maintain relatively high stability.

Test Example 3: Enzymolysis Kinetics Experiment of Compounds in Plasma

Figure 2:
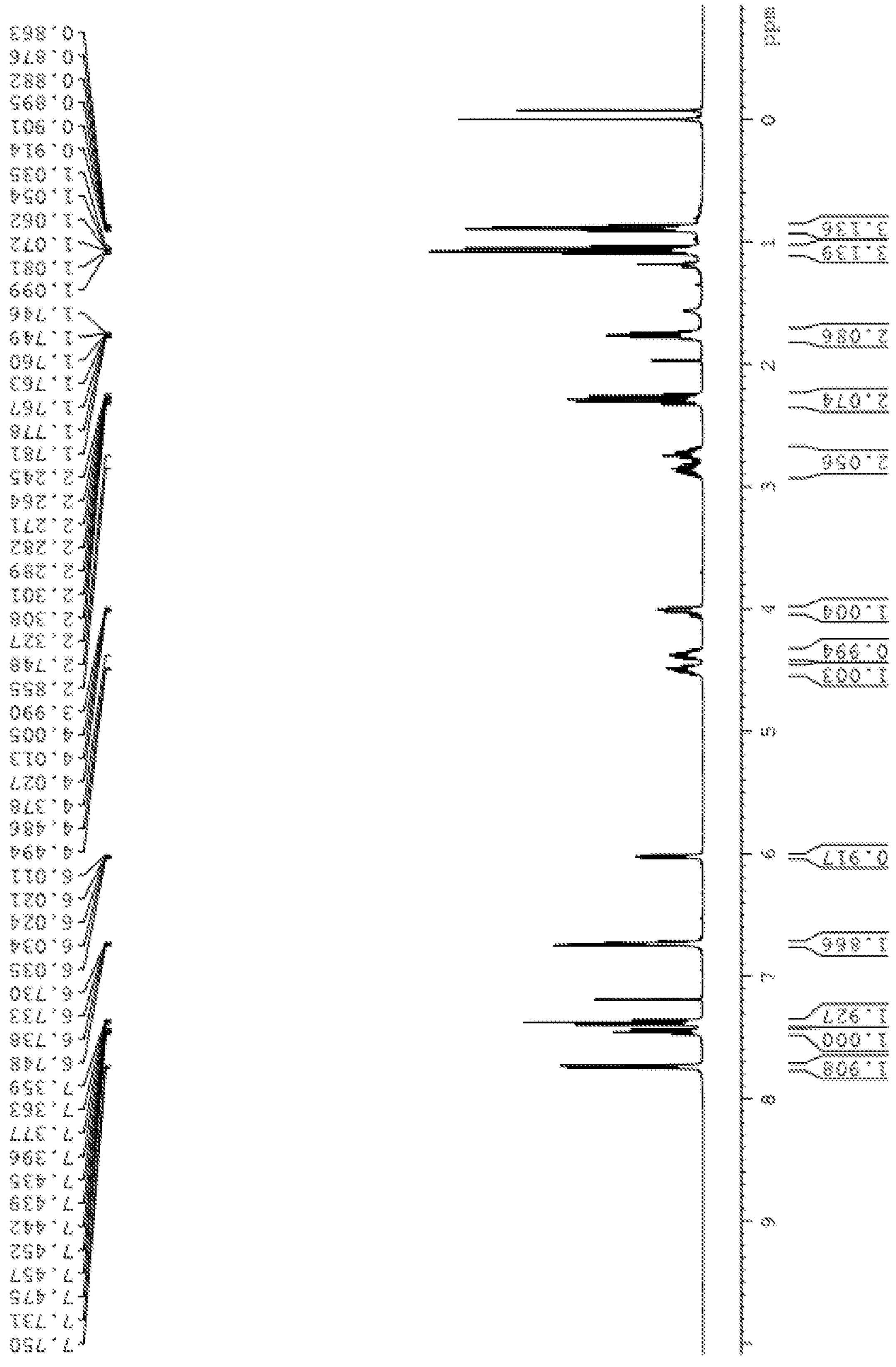
FIG. 2 is a hydrogen spectrum of the compound N8 of the present disclosure.
Figure 3:
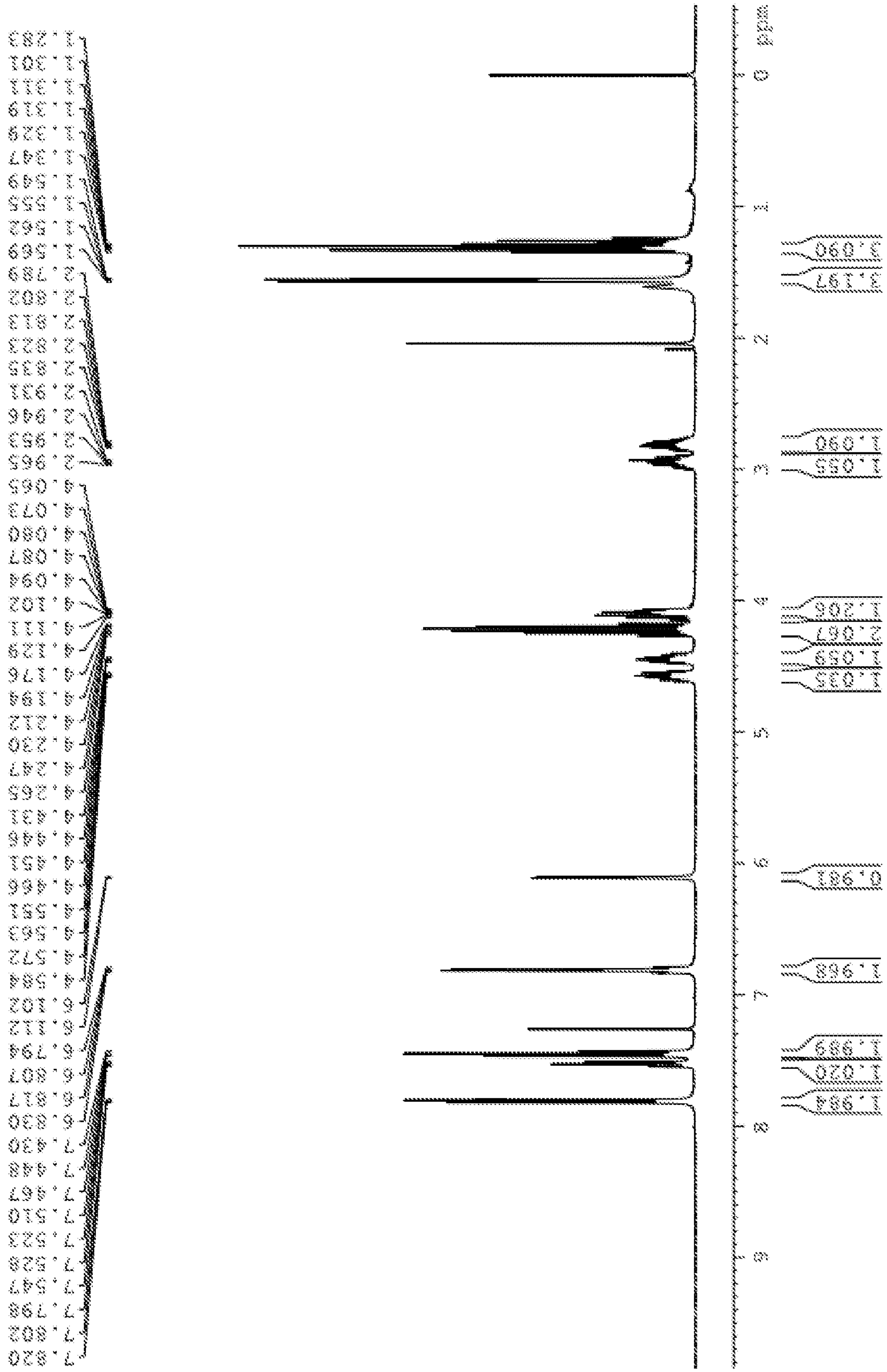
FIG. 3 is a hydrogen spectrum of the compound N12 of the present disclosure.
Figure 4:
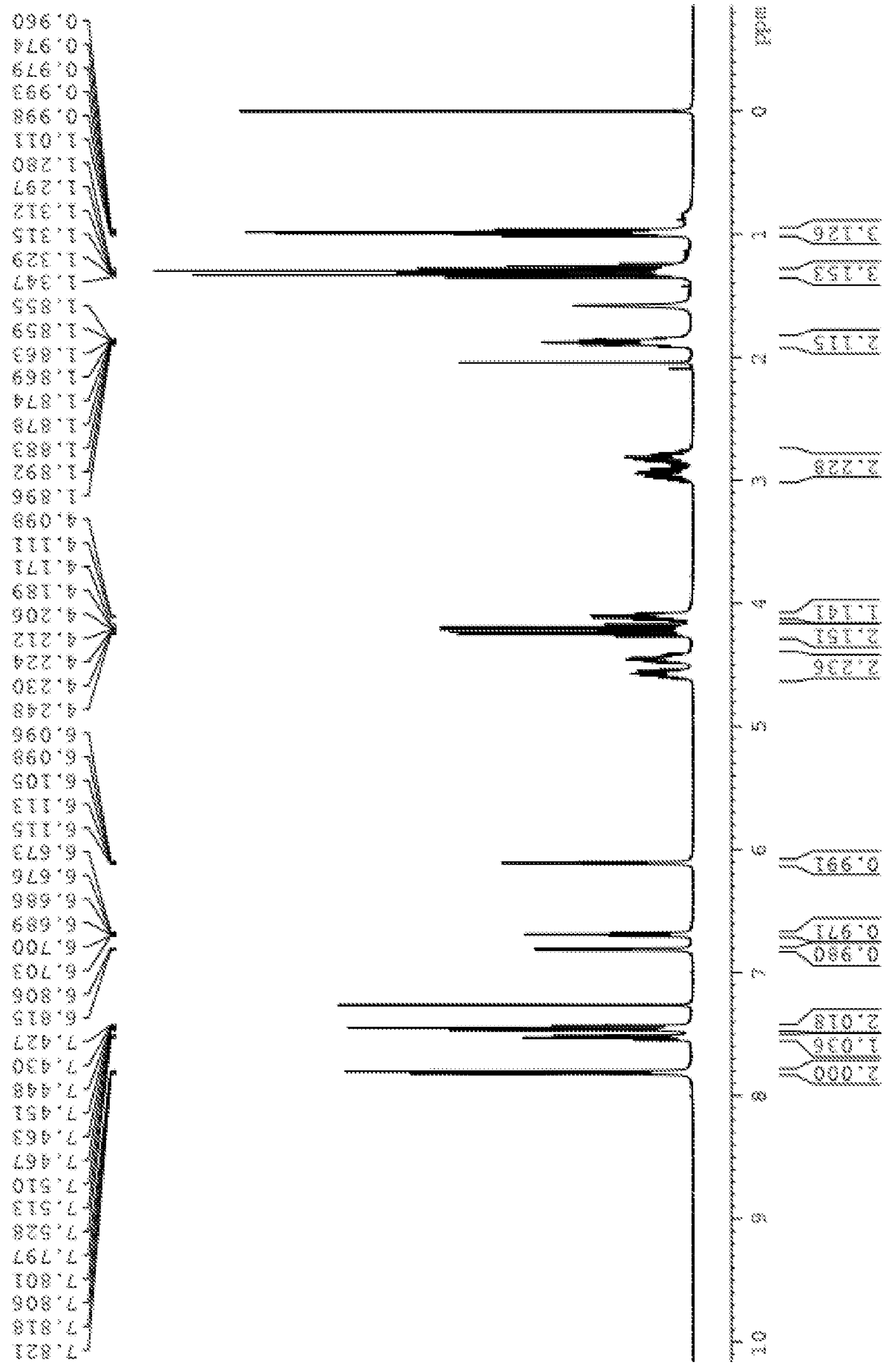
FIG. 4 is a hydrogen spectrum of the compound N15 of the present disclosure.
Figure 5:
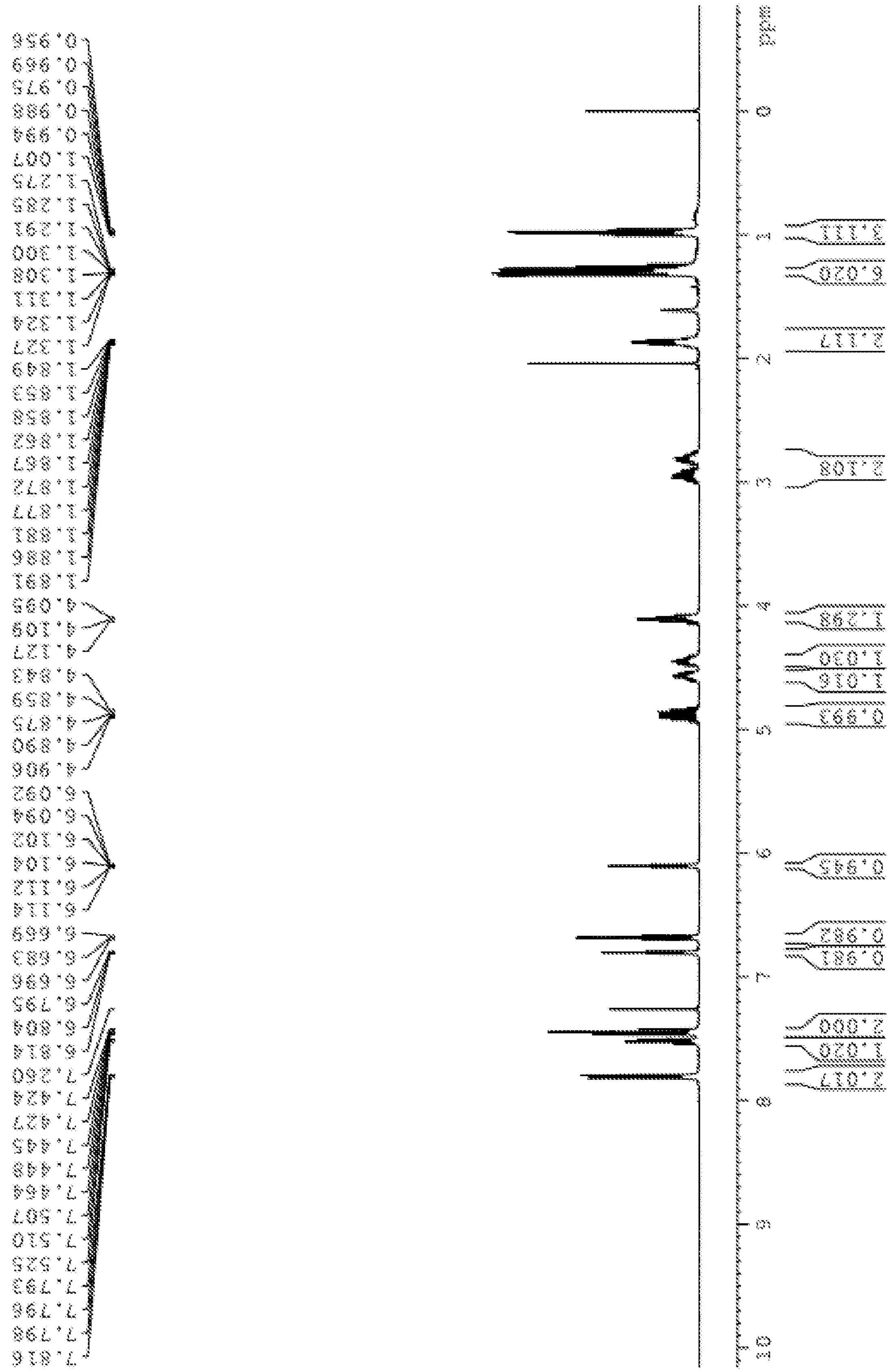
FIG. 5 is a hydrogen spectrum of the compound N16 of the present disclosure.

1. Procedures:

Compounds N2, N8, N12, N15 and N16 formulated in the examples, compound N11 formulated in Comparative Example 1, and flurbiprofen axetil in Comparative Example 2 were subjected to an enzymolysis kinetics experiment in human plasma in batches. The procedures were as follows:

(1) 4 mM compound NX (X represents different compound numbers), 4 mM methanol stock solution of flurbiprofen axetil and 4 mM methanol stock solution of ketorolac were prepared;

(2) 25 μL of ketorolac stock solution was mixed with 1 mL of human plasma, the reaction mixture was thawed by vortex for 30 s, followed by sampling 200 μL, 800 μL of acetonitrile was added for settling protein, and thawed by vortex for 1 min to terminate the reaction, and the resulting product was used as ketorolac control:

(3) 4 mM compound NX and 4 mM flurbiprofen axetil stock solution were diluted 200-fold as a control;

(4) 100 μL of methanol stock solution of compound NX and flurbiprofen axetil was weighed and added to 4 mL of human plasma, followed by mixing, the reaction mixture was thawed by vortex for 30 s, and placed in a water-bath constant-temperature oscillator at 37° C. and 100 rpm for oscillation;

(5) 200 μL samples were taken at different time points (0 min, 15 min, 30 min, 60 min and 120 min), with sampling for 3 times at each time point, 800 μL of acetonitrile was added to settle protein, and thawed by vortex for 1 min to terminate the reaction; and a blank plasma control was made by using the same method;

(6) the reaction solution was centrifuged at 12000 rpm and 4° C. for 10 min, the supernatant was collected and injected for 30 μL (via filter membrane), and peak area changes were recorded (shown in FIG. 2); and (7) the metabolic rate of compound NX and flurbiprofen axetil was observed and analyzed, and an appropriate compound NX was screened out according to the data.

Figure 6:
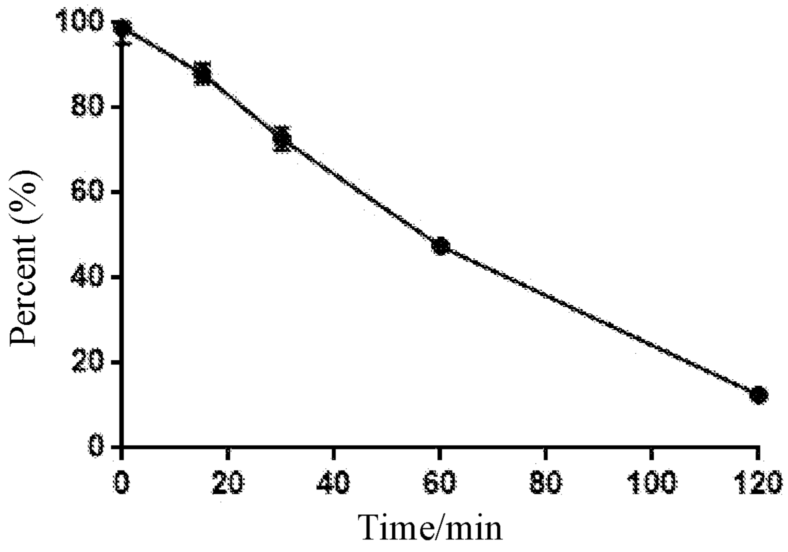
FIG. 6 is a line graph of the degradation rate of the compound N2 of the present disclosure in human plasma.

2. Experimental Results:

1) The content changes of compound N2 and ketorolac generated by metabolism are shown in Table 5; plasma metabolic rates of compound N2 at different time points are shown in FIG. 6.

TABLE 5

| | 0 min | 15 min | 30 min | 60 min | 120 min |
|---|---|---|---|---|---|
| Content of the compound % | 98.950 ± 3.765 | 88.103 ± 2.289 | 72.813 ± 2.707 | 47.510 ± 1.739 | 12.573 ± 0.260 |
| Content of ketorolac % | 1.050 ± 0.079 | 8.860 ± 0.426 | 20.993 ± 0.561 | 34.590 ± 1.381 | 59.790 ± 2.019 |

Figure 7:
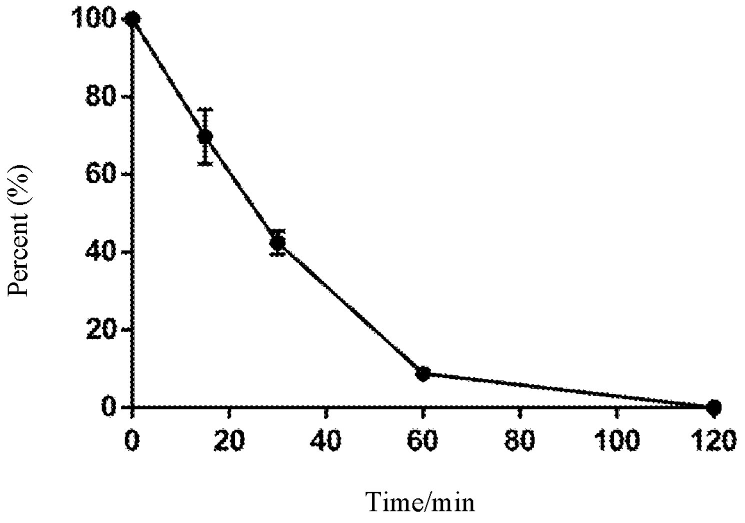
FIG. 7 is a line graph of the degradation rate of the compound N8 of the present disclosure in human plasma.

2) The content changes of compound N8 and ketorolac generated by metabolism are shown in Table 6; plasma metabolic rates of compound N8 at different time points are shown in FIG. 7.

TABLE 6

| | 0 min | 15 min | 30 min | 60 min | 120 min |
|---|---|---|---|---|---|
| Content of the compound % | 100 ± 1.782 | 69.713 ± 6.985 | 42.467 ± 2.983 | 8.777 ± 0.560 | 0 |
| Content of ketorolac % | 0 | 19.140 ± 1.467 | 36.277 ± 3.301 | 53.130 ± 2.171 | 65.997 ± 3.446 |

Figure 8:
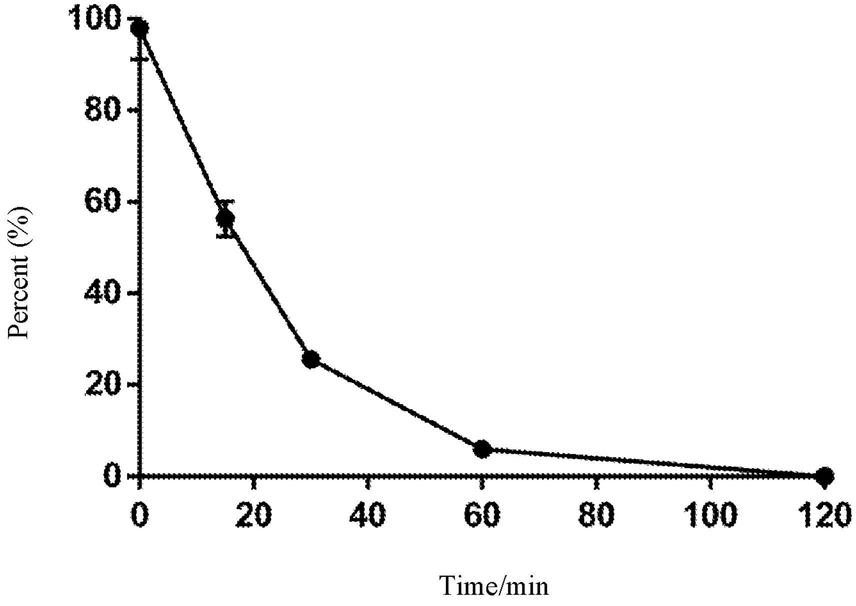
FIG. 8 is a line graph of the degradation rate of the compound N12 of the present disclosure in human plasma.

3) The content changes of compound N12 and ketorolac generated by metabolism are shown in Table 7; plasma metabolic rates of compound N I 2 at different time points are shown in FIG. 8.

TABLE 7

| | 0 min | 15 min | 30 min | 60 min | 120 min |
|---|---|---|---|---|---|
| Content of the compound % | 97.967 ± 6.878 | 56.277 ± 3.890 | 25.590 ± 1.131 | 5.997 ± 0.976 | 0 |
| Content of ketorolac % | 2.033 ± 0.342 | 34.203 ± 3.165 | 53.297 ± 1.296 | 76.623 ± 10.483 | 87.973 ± 4.045 |

Figure 9:
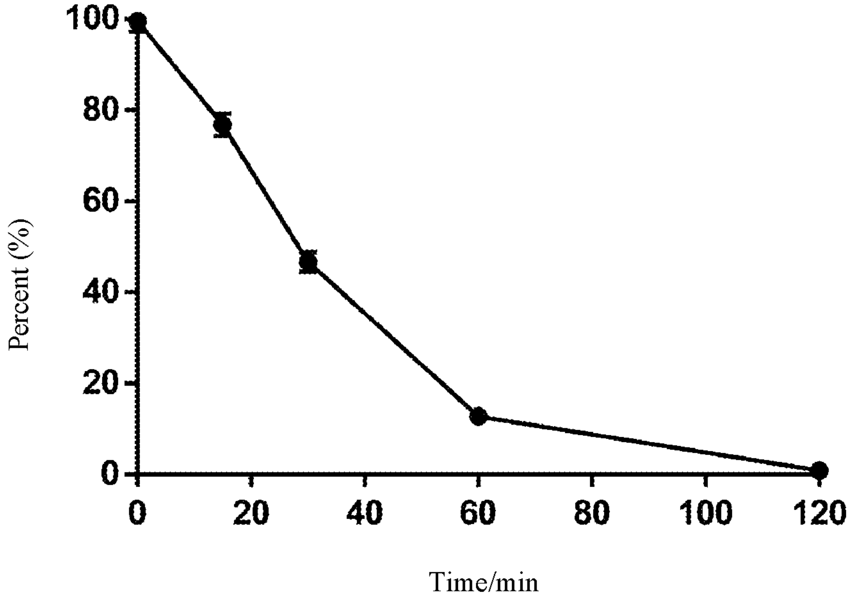
FIG. 9 is a line graph of the degradation rate of the compound N15 of the present disclosure in human plasma.
Figure 10:
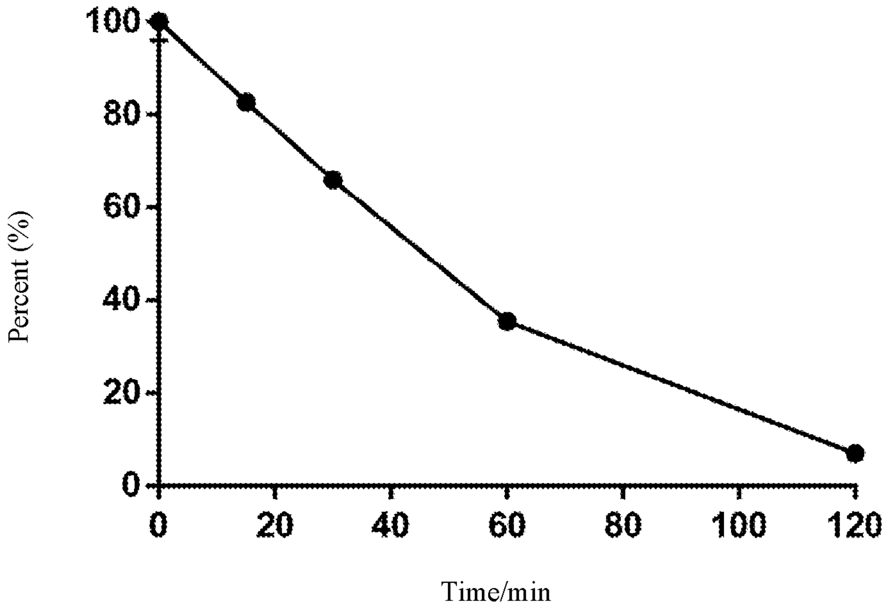
FIG. 10 is a liquid chromatogram of the degradation of the compound N15 of the present disclosure in human plasma.

4) The content changes of compound N15 and ketorolac generated by metabolism are shown in Table 8; plasma metabolic rates of compound N15 at different time points are shown in FIG. 9; a liquid chromatogram of the degradation of compound N13 in human plasma is shown in 10.

TABLE 8

| | 0 min | 15 min | 30 min | 60 min | 120 min |
|---|---|---|---|---|---|
| Content of the compound % | 99.560 ± 2.324 | 76.800 ± 2.423 | 46.680 ± 2.229 | 12.760 ± 1.133 | 0.893 ± 0.051 |
| Content of ketorolac % | 1.727 ± 1.502 | 23.933 ± 1.119 | 50.917 ± 1.868 | 83.957 ± 3.139 | 96.910 ± 3.848 |

Figure 11:
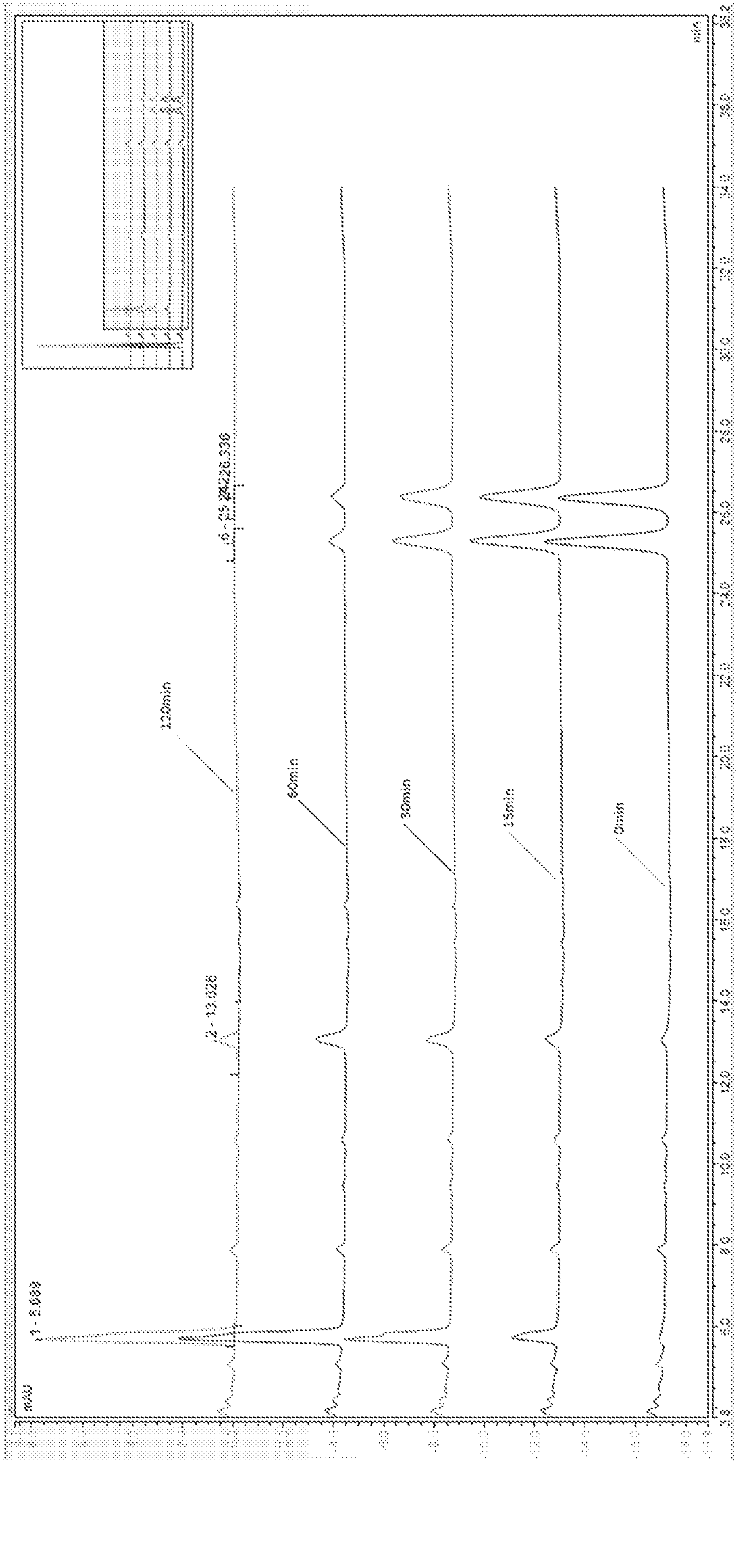
FIG. 11 is a line graph of the degradation rate of the compound N16 of the present disclosure in human plasma.

5) The content changes of compound N16 and ketorolac generated by metabolism are shown in Table 9; plasma metabolic rates of compound N16 at different time points are shown in FIG. 11.

TABLE 9

| | 0 min | 15 min | 30 min | 60 min | 120 min |
|---|---|---|---|---|---|
| Content of the compound % | 100 ± 4.001 | 82.710 ± 1.909 | 65.987 ± 0.506 | 35.437 ± 1.960 | 7.047 ± 0.374 |
| Content of ketorolac % | 0 | 9.847 ± 2.479 | 28.653 ± 0.277 | 56.793 ± 2.096 | 70.443 ± 4.274 |

Figure 16:
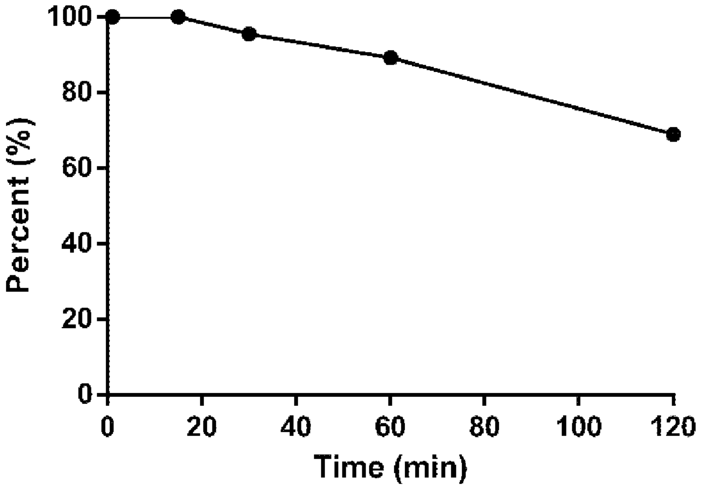
FIG. 16 is a line graph of the degradation rate of the compound N26 of the present disclosure in human plasma.

6) The content changes of compound N26 and ketorolac generated by metabolism are shown in Table 1; plasma metabolic rates of compound N26 at different time points are shown in FIG. 16.

TABLE 10

| | 1 min | 15 min | 30 min | 60 min | 120 min |
|---|---|---|---|---|---|
| Content of the compound % | 100 | 100 | 95.48 ± 1.56 | 89.20 ± 1.67 | 68.99 ± 1.45 |
| Content of ketorolac % | 0 | 0 | 3.89 ± 0.61 | 8.60 ± 0.33 | 24.34 ± 0.90 |

Figure 17:
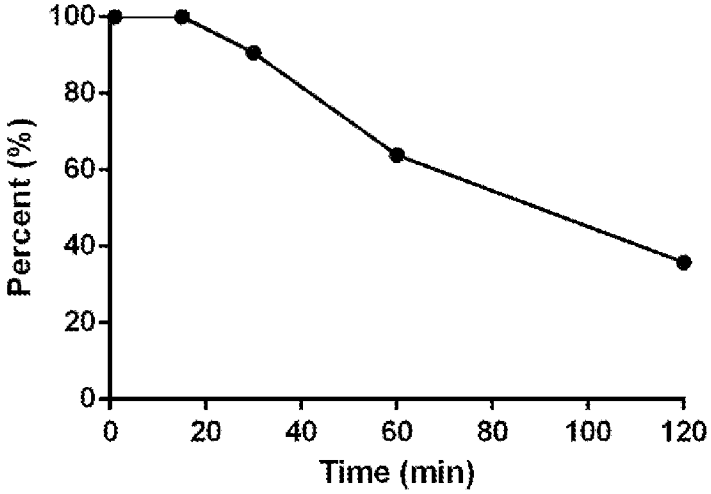
FIG. 17 is a line graph of the degradation rate of the compound N27 of the present disclosure in human plasma.

7) The content changes of compound N27 and ketorolac generated by metabolism are shown in Table 2; plasma metabolic rates of compound N27 at different time points are shown in FIG. 17.

TABLE 11

| | 1 min | 15 min | 30 min | 60 min | 120 min |
|---|---|---|---|---|---|
| Content of the compound % | 100 | 100 | 90.63 ± 1.81 | 63.89 ± 1.20 | 35.75 ± 1.46 |
| Content of ketorolac % | 0 | 0 | 9.89 ± 0.8 | 37.78 ± 1.13 | 66.73 ± 1.73 |

Figure 12:
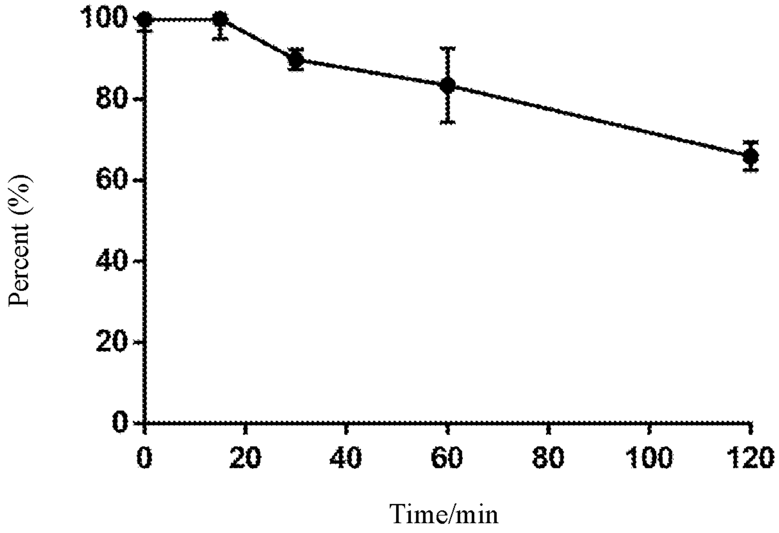
FIG. 12 is a line graph of the degradation rate of the compound N11 of the present disclosure in human plasma.
Figure 13:
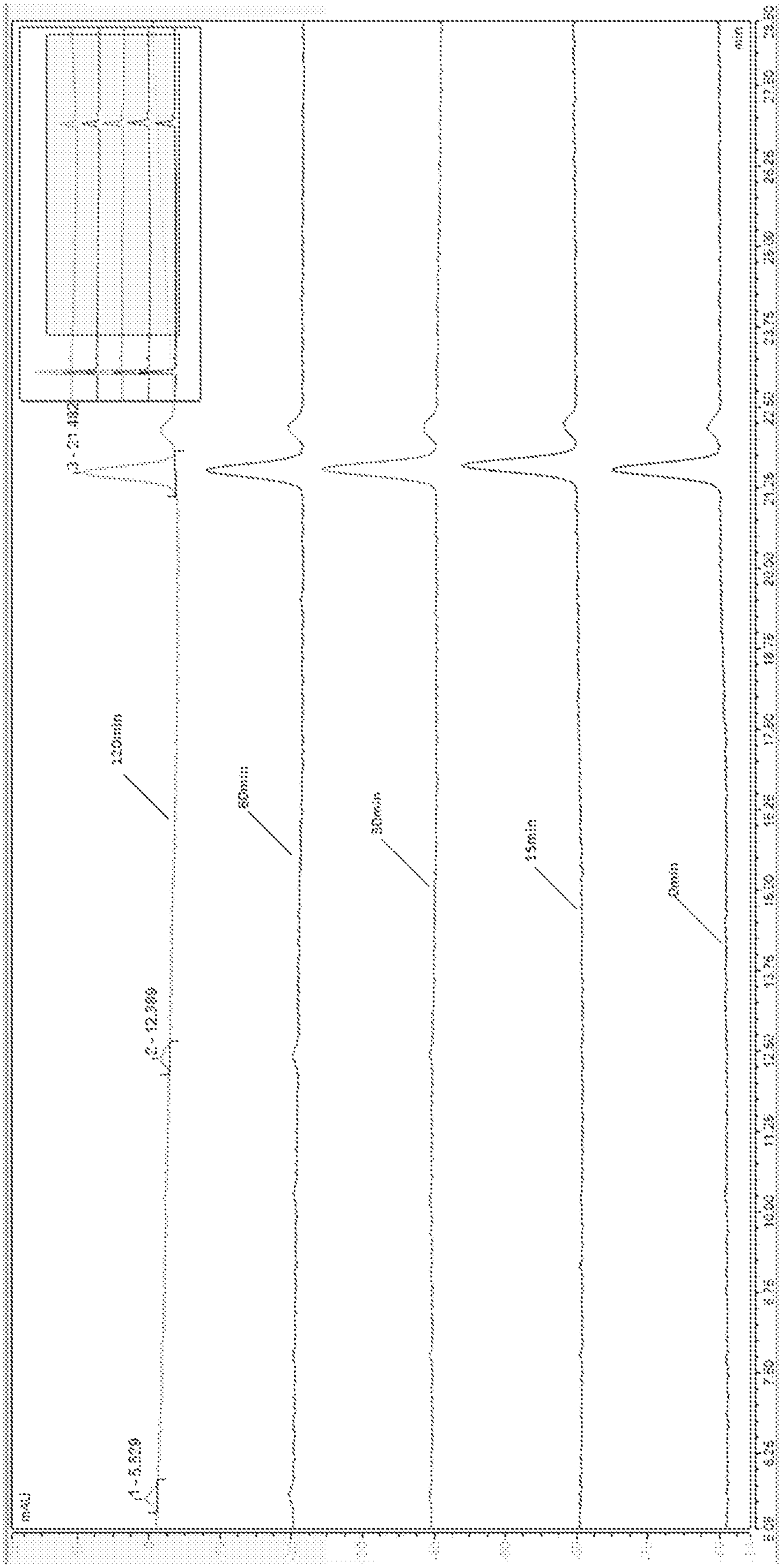
FIG. 13 is a liquid chromatogram of the degradation of the compound N11 of the present disclosure in human plasma.

8) The content changes of compound N11 in Comparative Example 1 and ketorolac generated by metabolism are shown in Table 12; plasma metabolic rates of compound N11 at different time points are shown in FIG. 12; a liquid chromatogram of the degradation of compound N11 in human plasma is shown in FIG. 13.

TABLE 12

| | 0 min | 15min | 30 min | 60 min | 120 min |
|---|---|---|---|---|---|
| Content of the compound % | 99.700 ± 2.928 | 99.813 ± 4.881 | 89.807 ± 2.538 | 83.490 ± 9.087 | 65.997 ± 3.446 |
| Content of ketorolac % | 0 | 0 | 0 | 2.270 ± 0.328 | 9.840 ± 1.977 |

Figure 14:
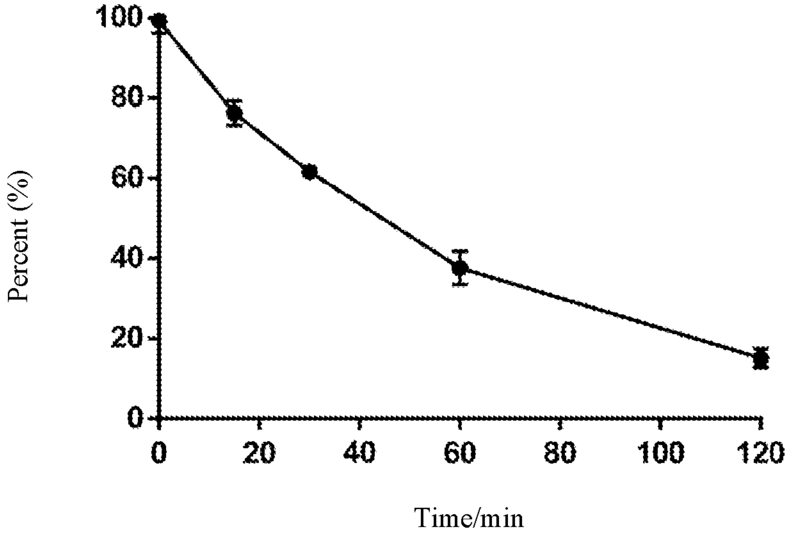
FIG. 14 is a line graph of the degradation rate of the compound PFA of the present disclosure in human plasma.
Figure 15:
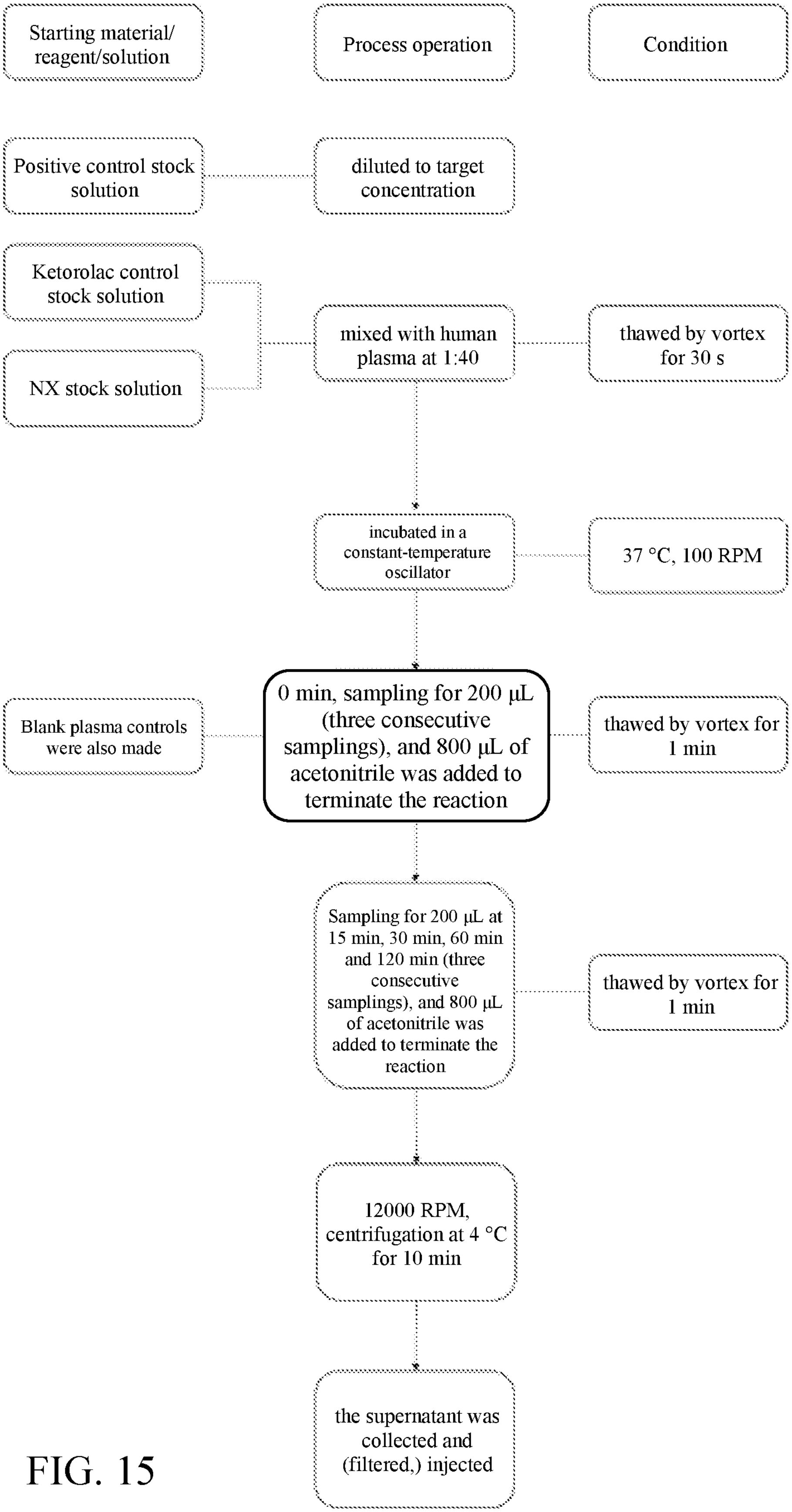
FIG. 15 is a flowchart of the enzymolysis kinetics experiment for the compound of the present disclosure.

9) The content changes of flurbiprofen axetil in Comparative Example 2 and flurbiprofen generated by metabolism are shown in Table 13; plasma metabolic rates of flurbiprofen axetil at different time points are shown in FIG. 14.

TABLE 13

| | 0 min | 15 min | 30 min | 60 min | 120 min |
|---|---|---|---|---|---|
| Content of the compound % | 99.285 ± 3.049 | 76.265 ± 3.146 | 61.665 ± 1.372 | 37.618 ± 4.180 | 15.152 ± 2.400 |
| Content of flurbiprofen % | 0 | 15.657 ± 0.432 | 27.593 ± 1.075 | 36.193 ± 4.749 | 53.317 ± 3.102 |

As can be seen from the test results, the compounds described above could be degraded in human plasma and metabolized to generate corresponding metabolites (ketorolac or flurbiprofen). Wherein, flurbiprofen axetil could be metabolized faster with an increase in the content of flurbiprofen as a metabolite, but only 50% of flurbiprofen produced. However, the metabolic rate of compound N11 was slow, the content of the compound was still kept to be nearly 70% after 120 min, and the generated amount of ketorolac was less than 10%; the remaining compounds N2, N8, N12, N15 and N16 all showed accelerated degradation and increased production of ketorolac.

Test Example 4

From the concentration versus time relationship, the hydrolysis process of the compounds follows first order reaction kinetics, and by plotting the natural logarithm of the concentrations of the remaining compounds versus time, a straight line could be obtained, a reaction rate constant k was obtained from a slope thereof, and the half-life period was calculated from $t_{1/2}$=0.693/k. The test results are shown in Table 12:

TABLE 12

| Name of the compounds | T½(min) |
|---|---|
| N2 | 38.56 |
| N8 | 16.93 |
| N12 | 14.77 |
| N15 | 16.93 |
| N16 | 31.55 |
| N11 | 347 |
| N26 | 176.83 |
| N27 | 73.88 |
| FPA | 40.82 |

As can be seen from the test results, the degradation rate of compound N11 was relatively slow, and the half-life period is relatively long ($T_{1/2}$=347 min); the half-life period of FPA was 40.82 min, similar to that of compound N2 ($T_{1/2}$=38.56 min); the metabolic rates of compound N8 ($T_{1/2}$=16.93 min), compound N12 ($T_{1/2}$=14.77 min) and compound N15 ($T_{1/2}$=16.93 min) were all relatively fast, and all of the compounds had similar half-life periods. In general, the compounds claimed in the present disclosure have half-life periods less than FPA, indicating that they are rapidly degraded in human plasma and produce the active metabolite ketorolac, thus exerting corresponding physiological effects.

Test Example 5

By-product toxicity test: according to the test of the toxicity of the metabolic byproducts by the metabolic pathways of the compounds in the human body, the metabolic byproducts and the toxicity of compounds N2-N22 in the human body are shown in the following table:

| Nos. | Metabolic by-products in human body | Toxicity |
|---|---|---|
| N2 | Acetaldehyde and isopropyl alcohol | relatively low |
| N3 | Propionaldehyde and acetic acid | relatively low |
| N4 | Acetaldehyde and propionic acid | relatively low |
| N5 | Isobutyraldehyde and acetic acid | Isobutyraldehyde is more toxic |
| N6 | Acetaldehyde and isobutyric acid | Isobutyric acid is more toxic |
| N7 | Acetaldehyde and pivalic acid | Pivalic acid is more toxic |
| N8 | Propionaldehyde and propionic acid | relatively low |
| N9 | Isobutyraldehyde and propionic acid | Isobutyraldehyde is more toxic |
| N10 | Acetaldehyde and cyclohexanol | relatively low |
| N12 | Acetaldehyde and acetic acid | relatively low |
| N13 | Acetaldehyde and methanol | Methanol is more toxic |
| N14 | Propionaldehyde and methanol | Methanol is more toxic |
| N15 | Propionaldehyde and ethanol | relatively low |
| N16 | Acetaldehyde and isopropyl alcohol | relatively low |
| N17 | Isobutyraldehyde and methanol | Isobutyraldehyde and methanol are more toxic |
| N18 | Isobutyraldehyde and ethanol | Isobutyraldehyde is more toxic |
| N19 | Isobutyraldehyde and isopropyl alcohol | Isobutyraldehyde is more toxic |
| N20 | Propionaldehyde and cyclohexanol | relatively low |
| N21 | Isobutyraldehyde and cyclohexanol | Isobutyraldehvde is more toxic |
| N22 | Acetaldehyde | relatively low |
| N26 | Acetaldehyde, carbon dioxide, and n-octanol | n-octanol is more toxic |
| N27 | Acetaldehyde and n-heptanoic acid | low |

According to the test data described above, the series of compounds have relatively low toxicity of byproducts after being metabolized in a human body, particularly, compounds N2, N3, N4, N8, N10, N12, N15, N16, N20, N21, N22, N26 and N27 have good clinical application prospects of drugs. Compounds N2, N8, N12, N15 and N16 and levorotatory enantiomers thereof, namely isomers with the carbon atom at position 1 being an S configuration, have low toxicity of byproducts after being metabolized in a human body and higher metabolic rates, are more suitable for being developed into injection formulations, and the route of administration can be selected from: subcutaneous injections, intramuscular injections, intravenous bolus injections, intravenous drip, etc.

In addition, compounds N10, N20, N21 and N22 and the levorotatory enantiomers thereof, namely the isomers with the carbon atom at position I being an S configuration, have relatively low toxicity of byproducts generated after being metabolized in a human body, have slow metabolic rates, and are more suitable for being developed into long-acting sustained-release formulations.

The embodiments of the present disclosure have been described above. However, the present disclosure is not limited the embodiments described above. Any modification, equivalent, improvement and the like made without departing from the spirit and principle of the present disclosure shall fall within the protection scope of the present disclosure.

The invention claimed is:

1. A compound of formula (I) and a racemate, a stereoisomer, a pharmaceutically acceptable salt or a solvate thereof, (I)

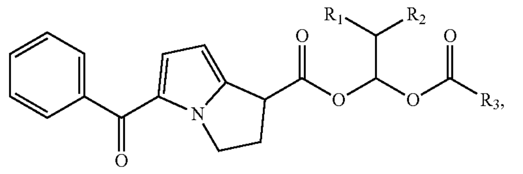

wherein $R_1$ is selected from hydrogen and $C_{1-8}$ alkyl, $R_2$ is selected from hydrogen and $C_{1-8}$ alkyl;

$R_3$ is selected from $C_{1-8}$ alkoxy.

2. The compound according to claim 1, wherein $R_1$ is selected from hydrogen, methyl, ethyl, isopropyl, isobutyl, and tert-butyl, $R_2$ is selected from hydrogen, methyl, ethyl, isopropyl, isobutyl, and tert-butyl, and $R_3$ is selected from methoxy, ethoxy, isopropoxy, tert-butoxy, and isobutoxy.

3. A preparation method for the compound of formula (I) according to claim 1, comprising reacting compound 1 with compound 2 to give the compound of formula (I):

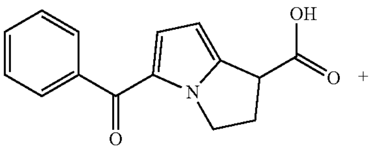

+

1

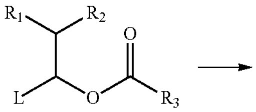

2

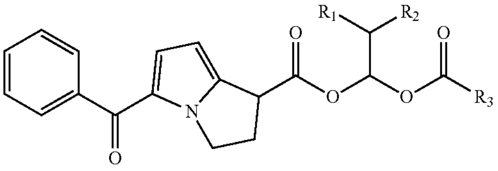

(I)

wherein $R_1$, $R_2$ and $R_3$ are all independently defined as in claim 1;

L is selected from a leaving group; and the compound 1 is selected from a racemic ketorolac, ketorolac having an R configuration and ketorolac having an S configuration, (±)-5-benzoyl-2,3-dihydro-1H-pyrrolizine-1-carboxylic acid, (R)-5-benzoyl-2,3-dihydro-1H-pyrrolizine-1-carboxylic acid, and(S)-5-benzoyl-2,3-dihydro-1H-pyrrolizine-1-carboxylic acid.

4. The preparation method according to claim 3, comprising carrying out the reaction in the presence of an organic solvent, wherein the organic solvent is selected from at least one of the following: acetone, dimethyl sulfoxide, N,N-dimethylformamide, ethers, polyethers of ethylene oxide, polyethers propylene oxide, aliphatic hydrocarbons, cycloaliphatic hydrocarbons, aromatic hydrocarbons, and esters.

5. A method for treating inflammation or analgesia, comprising administrating the compound of formula (I), the racemate, the stereoisomer, the pharmaceutically acceptable salt or the solvate thereof according to claim 1 to a subject in need thereof, wherein the inflammation or analgesia is caused by rheumatoid arthritis, lumbago, migraine, neuralgia, scapulohumeral periarthritis, osteoarthritis, neck-shoulder-wrist syndrome, surgery, trauma, tooth extraction, or acute upper respiratory tract inflammation.

6. A pharmaceutical composition comprising the compound of formula (I), the racemate, the stereoisomer, the pharmaceutically acceptable salt, or the solvate thereof according to claim 1.

7. The compound according to claim 1, wherein the compound of formula (I) is selected from:

N2

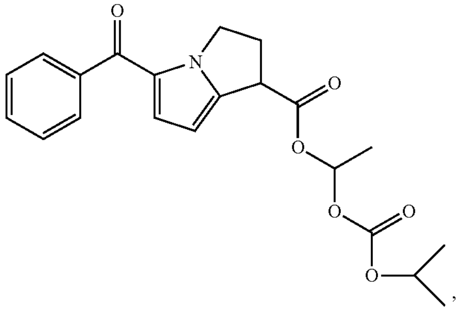

,

N12

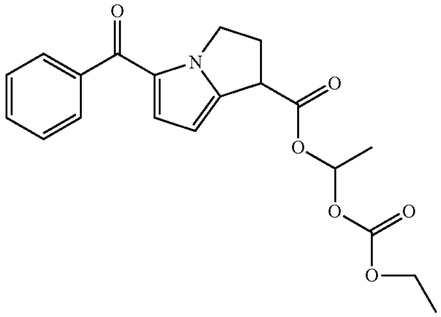

,

N13

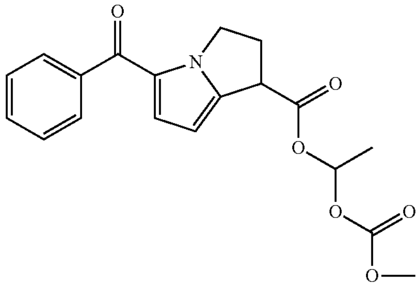

,

N14

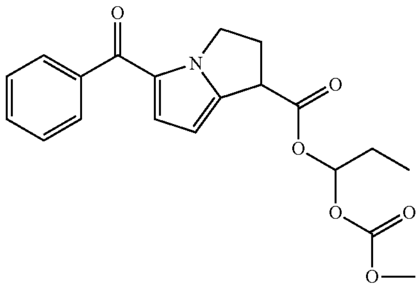

,

N15

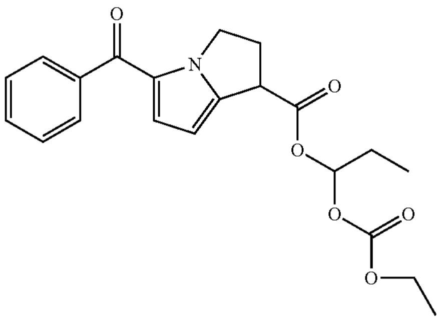

,

-continued
N16
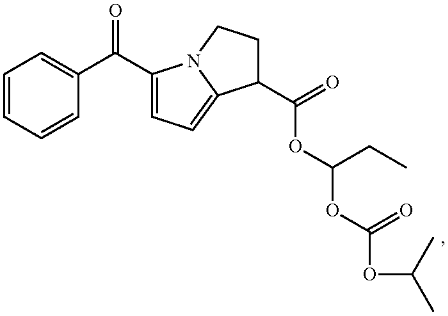
,
N17
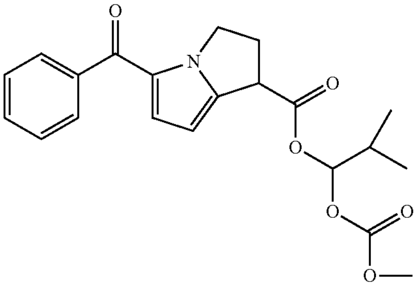
,
N18
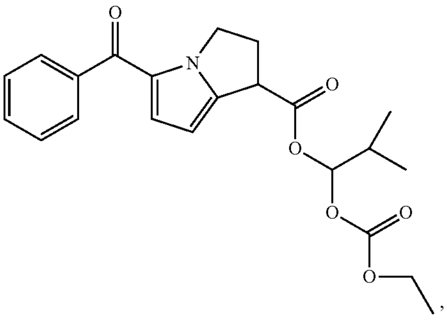
, and
N19
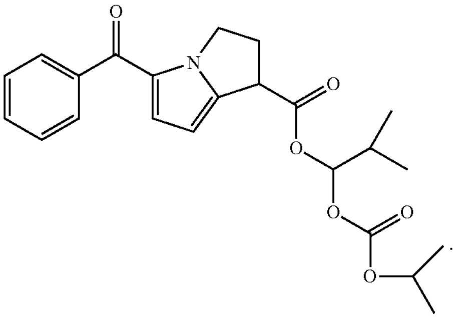
.
8. The compound according to claim 1, wherein the compound of formula (I) is selected from:
N2(S)
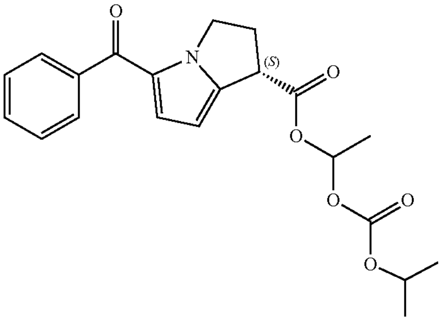
,
N12(S)
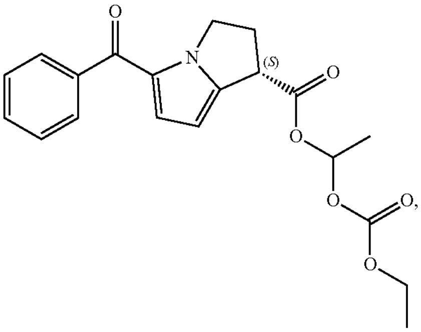
,
N15(S)
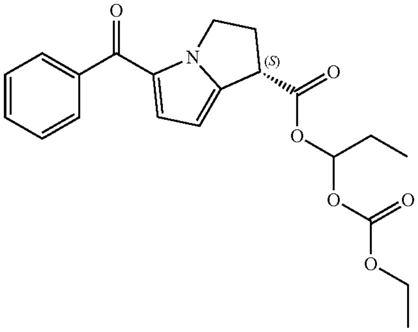
,
N16(S)
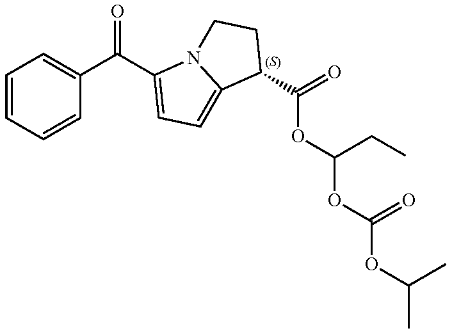
.
9. The preparation method according to claim 3, wherein L is selected from halogen and hydroxy; compound 2 is compound 3:
3
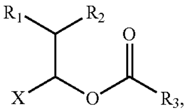
, wherein $R_1$, $R_2$ and $R_3$ are all independently defined as in claim 1; and X is selected from chlorine, bromine, and iodine.

10. The preparation method according to claim 4, wherein the ethers are selected from ethyl propyl ether, n-butyl ether, anisole, phenetole, cyclohexyl methyl ether, dimethyl ether, diethyl ether, dimethyl ethylene glycol, diphenyl ether, dipropyl ether, diisopropyl ether, di-n-butyl ether, diisobutyl ether, diisopentyl ether, dimethoxyethane, isopropyl ethyl ether, methyl tert-butyl ether, tetrahydrofuran, methyl tetrahydrofuran, dioxane, and dichlorodiethyl ether; and wherein the aliphatic hydrocarbons, the cycloaliphatic hydrocarbons, or the aromatic hydrocarbons are selected from pentane, hexane, heptane, octane, nonane, methylene chloride, dichloromethane, trichloromethane, carbon tetrachloride, fluorobenzene, chlorobenzene, dichlorobenzene; cyclohexane, methylcyclohexane, petroleum ether, octane, benzene, toluene, chlorobenzene, bromobenzene, and xylene; and wherein the esters are selected from methyl acetate, ethyl acetate, butyl acetate, isobutyl acetate and dimethyl carbonate, dibutyl carbonate, and ethylene carbonate.

11. The preparation method according to claim 3, further comprising carrying out the reaction in the presence of an acid binding agent that is an organic base or an inorganic base.

12. The preparation method according to claim 11, wherein the inorganic base is selected from hydrides, hydroxides, alkoxides, acetates, fluorides, phosphates, carbonates, bicarbonate of alkali metals, and bicarbonate of alkaline earth metals, and wherein the organic base is selected from tertiary amines, substituted or unsubstituted pyridines and substituted or unsubstituted triethylamine, trimethylamine, N,N-diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2,3- or 4-methylpyridine, 2-methyl-5-ethylpyridine, 2,6-dimethylpyridine, 2,4,6-trimethylpyridine, 4-dimethylaminopyridine, quinoline, methylquinoline, N,N,N,N-tetramethylethylenediamine, N,N-dimethyl-1,4-diazacyclohexane, N,N-diethyl-1,4-diazabicyclocyclohexane, 1,8-bis(dimethylamino)naphthalene, diazabicyclooctane (DABCO), diazabicyclononane (DBN), diazabicycloundecane (DBU), butylimidazole, and methylimidazole.

13. The preparation method according to claim 11, wherein the inorganic base is selected from sodium amide, sodium hydride, lithium diisopropylamide, sodium methoxide, potassium tert-butoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate, and cesium carbonate.

14. The preparation method according to claim 3, wherein the reaction is carried out in the presence of a catalyst.

15. The preparation method according to claim 14, wherein the catalyst is selected from tetrabutylammonium bromide (TBAB), tetrabutylammonium chloride (TBAC), tetrabutylammonium iodide (TBAI), potassium iodide, sodium iodide, and 18-crown-6.

16. The preparation method according to claim 3, wherein the reaction is carried out at a reaction temperature of 5-80° C. for a reaction time of 0.5-24 h.

* * * * *